United States Patent
Sheng

(10) Patent No.: US 11,946,100 B2
(45) Date of Patent: Apr. 2, 2024

(54) MICRODROPLET CONTAINER AND METHOD FOR MANUFACTURING THE SAME, METHOD FOR SPREADING MICRODROPLETS, MICRODROPLET-GENERATING KIT, TEMPERATURE-CONTROLLING DEVICE, OIL PHASE COMPOSITION FOR MICRODROPLET GENERATING AND METHOD FOR TREATING THE SAME

(71) Applicant: Sniper (Suzhou) Life Technology Co, Ltd, Jiangsu (CN)

(72) Inventor: Guang-Ji Sheng, Beijing (CN)

(73) Assignee: SNIPER (SUZHOU) LIFE TECHNOLOGY CO., LTD., Suzhou (CN)

( * ) Notice: Subject to any disclaimer, the term of this patent is extended or adjusted under 35 U.S.C. 154(b) by 922 days.

(21) Appl. No.: 16/964,607

(22) PCT Filed: Jan. 24, 2019

(86) PCT No.: PCT/CN2019/072969
§ 371 (c)(1),
(2) Date: Jul. 24, 2020

(87) PCT Pub. No.: WO2019/144905
PCT Pub. Date: Aug. 1, 2019

(65) Prior Publication Data
US 2021/0047680 A1 Feb. 18, 2021

(30) Foreign Application Priority Data
Jan. 24, 2018 (CN) .......................... 201810070377.2
Jul. 27, 2018 (CN) .......................... 201810843257.1

(51) Int. Cl.
C12Q 1/6851 (2018.01)
B01L 3/00 (2006.01)
C12Q 1/6806 (2018.01)
G01N 21/75 (2006.01)

(52) U.S. Cl.
CPC ...... *C12Q 1/6851* (2013.01); *B01L 3/502738* (2013.01); *C12Q 1/6806* (2013.01); *G01N 21/75* (2013.01)

(58) Field of Classification Search
CPC ................ C12Q 1/6851; C12Q 1/6806; B01L 3/502738; B01L 3/52; B01L 7/52; B01L 2200/147; B01L 2300/0829; B01L 2300/0858; B01L 2300/0864; B01L 2300/161; B01L 2300/1822; B01L 2400/021; B01L 2400/028; B01L 3/502784; G01N 21/75; G01N 21/64; H01L 23/345; H01L 23/3672; H01L 23/38; H01L 23/467; H01L 23/4985
See application file for complete search history.

(56) References Cited

U.S. PATENT DOCUMENTS

| | | | |
|---|---|---|---|
| 6,551,557 B1 | 4/2003 | Rose et al. | |
| 2007/0157628 A1* | 7/2007 | Onoue | H01L 23/38 62/3.2 |
| 2012/0304929 A1 | 12/2012 | Ivri | |
| 2014/0272982 A1 | 9/2014 | Yamana et al. | |
| 2015/0062824 A1* | 3/2015 | Hyun | H01L 23/34 361/716 |
| 2015/0375239 A1 | 12/2015 | Herre et al. | |
| 2017/0253915 A1 | 9/2017 | Du et al. | |
| 2017/0356036 A1 | 12/2017 | Davies et al. | |

FOREIGN PATENT DOCUMENTS

| | | |
|---|---|---|
| CN | 1858201 | 11/2006 |
| CN | 1986229 | 6/2007 |
| CN | 101974421 | 2/2011 |
| CN | 102232114 | 11/2011 |
| CN | 202195997 U | 4/2012 |
| CN | 103434272 A | 12/2013 |
| CN | 103717308 | 4/2014 |
| CN | 104107734 A | 10/2014 |
| CN | 104324769 | 2/2015 |
| CN | 104388307 A | 3/2015 |
| CN | 104450891 | 3/2015 |
| CN | 105498869 A | 4/2016 |

(Continued)

OTHER PUBLICATIONS

Lievens A. et al: "Measuring Digital PCR Quality: Performance Parameters and Their Optimization" vol. 11, No. 5, Jun. 5, 2016, p. 3-p. 16.
Scott O. Sundberg et al:"Spining Disk Platform for Microfluidic Digital Polymerease Chain Reaction" Analytical Chemistry, vol. 82, No. 4, Feb. 15, 2010, pp. 1546-1550.
Phenix-Lan Quan et al: "dPRC : A Technology Review" Sensors, vol. 18, No. 4, Apr. 20, 2018, pp. 1271.
Kevin A Heyries et al:"Megapixel digital PCR" Mature Methods, vol. 8, No. 8, Jul. 3, 2011, pp. 649-651.
International Search Report of PCT/CN2019/072926.
International Search Report of PCT/CN2019/072969.

(Continued)

*Primary Examiner* — Narayan K Bhat
(74) *Attorney, Agent, or Firm* — Cherskov Flaynik & Gurda, LLC

(57) ABSTRACT

The present application provides a microdroplet container and a method for manufacturing the same, a method for spreading microdroplets, a microdroplet-generating kit, a temperature-controlling device, an oil phase composition for microdroplet generating and a method for treating the same. The temperature controlling device includes a flexible circuit board a heating substrate, and multiple semiconductor electric couples. The semiconductor electric couples are disposed between the flexible circuit board and a first surface of the heating substrate, and are connected to each other.

17 Claims, 18 Drawing Sheets

(56) References Cited

FOREIGN PATENT DOCUMENTS

| | | |
|---|---|---|
| CN | 105854965 A | 8/2016 |
| CN | 205501281 | 8/2016 |
| CN | 105925572 A | 9/2016 |
| CN | 106520524 | 3/2017 |
| CN | 106596489 | 4/2017 |
| CN | 106662374 | 5/2017 |
| CN | 106754341 | 5/2017 |
| CN | 106755345 | 5/2017 |
| CN | 104450891 | 6/2017 |
| CN | 106854618 | 6/2017 |
| CN | 107349882 A | 11/2017 |
| CN | 107478629 A | 12/2017 |
| CN | 107513495 A | 12/2017 |
| CN | 107586700 | 1/2018 |
| CN | 107622185 | 1/2018 |
| CN | 207596826 | 7/2018 |
| CN | 108373971 A | 8/2018 |
| CN | 208131057 | 11/2018 |
| CN | 208378891 | 1/2019 |
| CN | 208494266 | 2/2019 |
| CN | 110066857 A | 7/2019 |
| DE | 102015011970 | 3/2017 |
| EP | 2848698 | 3/2015 |
| EP | 3236269 | 10/2017 |
| JP | 1997139525 A | 5/1997 |
| JP | 2003170425 | 6/2003 |
| JP | 2003170425 A | 6/2003 |
| JP | 2003174203 A | 6/2003 |
| JP | 2004279340 A | 10/2004 |
| JP | 2007257014 | 10/2007 |
| JP | 4323528 B2 | 9/2009 |
| JP | 2017013011 A | 1/2017 |
| JP | 2017063779 A | 4/2017 |
| KR | 20100128518 A | 12/2010 |
| WO | WO2002006450 A1 | 1/2002 |
| WO | WO2013049443 | 4/2013 |
| WO | WO2013072069 | 5/2013 |
| WO | WO2013130857 A1 | 9/2013 |
| WO | WO2014/025924 | 2/2014 |
| WO | WO2016/014976 | 1/2016 |
| WO | WO2016/133783 | 8/2016 |
| WO | WO2017007954 | 1/2017 |
| WO | WO2018094081 A | 5/2018 |

OTHER PUBLICATIONS

«Scientific Reports» Aug. 29, 2017 Nivedita Majumdar etc. Poission Plus Quantification for Digital PCR Systems. pp. 1-10.
Philip J Wilson et al. "Extending digital PRC analysis by modelling quantification cycle data", «BMC Bioinformatics», Oct. 12, 2016.
Mitra Mojtahedi et al. "Direct elicitation of template concentration from quantification cyale(Cq) distributions in digital PCR", «Nucleic Acids Res», Aug. 7, 2014.
Shufang Zhou et al. "A highly integrated real-time digital PCR device for accurate DNA quantitative analysis", «Biosens Bioelectron», Jan. 11, 2019, pp. 151-158.
Chen Chao, "New Technology and Precise Medical Science", «Shanghai Jiao Tong University Press», Dec. 31, 2017, pp. 150-151.
Sofronova J.K. et al. "Detection of Mutations in Mitochondrial DNA by Droplet Digital PCR" Biochemistry (Moscow), vol. 81, No. 10, Oct. 31, 2016(Oct. 31, 2016), pp. 1031-1037.
International Search Report of PCT/CN2019/072974.

\* cited by examiner

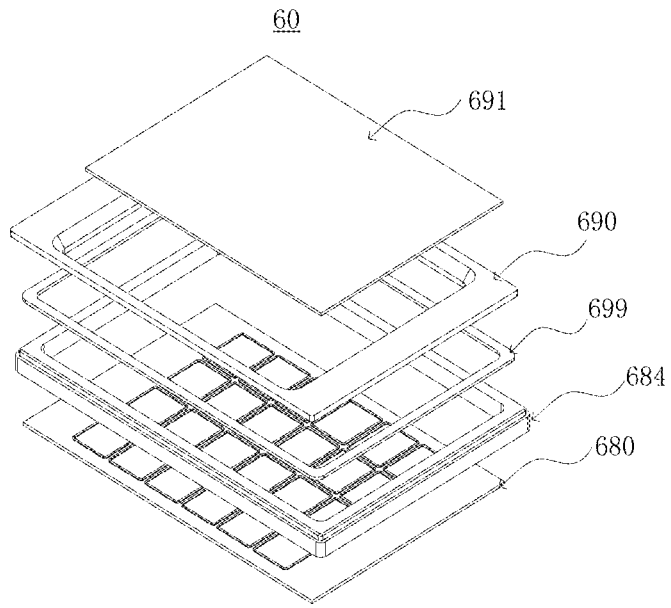

FIG. 48

```
providing a microdroplet container, the
microdroplet container having an opening, and
the microdroplet container containing a second
liquid
```
— S311

```
providing a first liquid, a density of the first
liquid being greater than a density of the
second liquid, and the first liquid being not
miscible with the second liquid; and stacking
the plurality of microdroplets generated from
the first liquid on a bottom plate of the
microdroplet container
```
— S312

```
temperature cycling the plurality of
microdroplets between high and low
temperatures until the plurality of
microdroplets are spread on the bottom plate
```
— S313

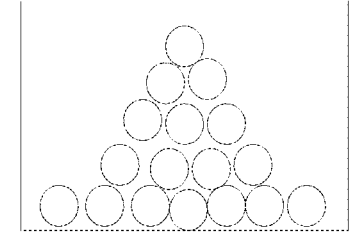

MICRODROPLET CONTAINER AND METHOD FOR MANUFACTURING THE SAME, METHOD FOR SPREADING MICRODROPLETS, MICRODROPLET-GENERATING KIT, TEMPERATURE-CONTROLLING DEVICE, OIL PHASE COMPOSITION FOR MICRODROPLET GENERATING AND METHOD FOR TREATING THE SAME

CROSS-REFERENCE TO RELATED APPLICATIONS

This application claims priority benefits from China Patent Application No. 201810070377.2, filed on Jan. 24, 2018, entitled "DIGITAL PCR QUANTITATIVE DETECTING METHOD", and China Patent Application No. 201810843257.1, filed on Jul. 27, 2018, entitled "MICRODROPLET CONTAINER AND METHOD FOR MANUFACTURING THE SAME". The entireties of these applications are incorporated by reference herein for all purposes. This application is a 35 U.S.C. § 371 national application of international patent application PCT/CN2019/072969 filed on Jan. 24, 2019, the content of which is also hereby incorporated by reference. This application is related to commonly-assigned applications, entitled "DIGITAL PCR DETECTION APPARATUS, DIGITAL PCR QUANTITATIVE DETECTION METHOD, MULTI-VOLUME DIGITAL PCR QUANTITATIVE ANALYSIS METHOD, DIGITAL PCR DETECTION METHOD, NUCLEIC ACID DETECTION MICROSPHERE, PREPARATION METHOD OF NUCLEIC ACID DETECTION MICROSPHERE, NUCLEIC ACID DETECTION MICROSPHERE KIT AND HIGH-THROUGHPUT NUCLEIC ACID DETECTION METHOD" (U.S. Ser. No. 16/964,183) and "MOTION CONTROLLING MECHANISM, LIQUID DISCHARGING NOZZLE, MICRODROPLET GENERATING DEVICE AND METHOD, LIQUID DRIVING MECHANISM AND METHOD, MICRODROPLET GENERATING METHOD, AND SURFACE PROCESSING METHOD OF LIQUID DISCHARGING NOZZLE" (U.S. Ser. No. US16/964,599), the contents of which are also hereby incorporated by reference.

TECHNICAL FIELD

The present application relates to the microdroplet technical field, and particularly relates to a microdroplet container and a method for manufacturing the same, a method for spreading microdroplets, a microdroplet-generating kit, a temperature-controlling device, an oil phase composition for microdroplet generating and a method for treating the same.

BACKGROUND

The digital PCR (dPCR) is a technique for absolute quantification of nucleic acid molecules. Compared with qPCR, the number of DNA molecules can be counted in the digital PCR which is the absolute quantification for the starting sample. In recent years, the digital PCR technology has rapidly developed. The conventional integrated microfluidic control chips, micro-well array chips and droplet microfluidic control chips based on the micro-nano manufacturing and microfluidic control technique are disposable consumables to be discarded after a single use to prevent cross-contamination. However, in the actual process, there are restrictions on the number of microdroplets, and the cost of the consumables is relatively high. The overall surface of the liquid in the conventional microdroplet container is curved, and in some cases, the liquid surface is a concave liquid surface. The plurality of microdroplets in the falling process are gathered at the middle of the microdroplet container and gathered together, interfering with the fluorescence image obtaining of the batch of microdroplets. In the generating process of the plurality of microdroplets, physical properties, such as viscosity, of a conventional oil phase composition change greatly in use of the composition, so that the volume uniformity of the generated microdroplets is poor. Moreover, the conventional temperature controlling device has small temperature increasing and decreasing speeds, requiring a long time to complete a nucleic acid amplification and affecting the detection efficiency of the digital PCR.

SUMMARY

In view of this, the present application provides a microdroplet container including a bottom surface, a first surrounding side surface surrounding the bottom surface, and a surrounding surface. The first surrounding side surface is connected to and surrounds the bottom surface to form a receiving space having an opening. The first surrounding side surface is perpendicular to the bottom surface. The surrounding surface surrounds the opening and is connected to the first surrounding side surface. The surrounding surface is parallel to the bottom surface. The receiving space is configured for accommodating a plurality of microdroplets and an oil phase composition. The surface of the liquid in the microdroplet container can be ensured to be a horizontal flat surface, by having the surrounding surface parallel to the bottom surface and by adding the oil phase composition to reach the surrounding surface. By having the surrounding surface, the surface of the liquid in the microdroplet container can be in the flat state, and the overall surface of the liquid in the microdroplet container is prevented from being curved. Therefore, the observation of the microdroplets adjacent to the edge of the container bottom plate will not be affected by the microdroplet container, facilitating camera imaging and increasing a detected number of the plurality of microdroplets.

In view of this, the present application provides a microdroplet container, including a first container bottom plate, a polygonal frame, and a container lid. The first container bottom plate includes a plurality of polygonal ridges. The polygonal frame surrounds and defines a first receiving space. The polygonal frame is connected to the first container bottom plate. The plurality of polygonal ridges are disposed in the first receiving space. The container lid is disposed on a surface of the polygonal frame, and the surface is away from the first container bottom plate. The container lid is detachably connected to the polygonal frame. The container lid and the polygonal frame surround and define an oil reservoir. The two sides of the polygonal ridges are respectively connected to the first container bottom plate and the container lid, and the container lid is detachably connected to the polygonal frame, so that the microdroplet container can be sealed. The container lid and the polygonal frame surround and define the oil reservoir. When the microdroplet container is sealed by the container lid, excess oil in the microdroplet container can be squeezed into the oil reservoir, so that the affecting of the oil above the microdroplets on the detection process can be avoided as much as possible, and the fluorescent background caused by the oil can be avoided. Moreover, by squeezing the excess oil in the microdroplet container into the oil reservoir, the amount of the oil remained in the microdroplet container around the microdroplets is reduced, so as to prevent the water-unsaturated oil absorbing water from the microdroplets, and to avoid the water diminishing of the microdroplets. In use, air may be mixed and bubbles may be generated in the oil liquid accommodated by the microdroplet container, which may affect the fluorescence signal detecting device taking images of the fluorescence variations of the plurality of microdroplets in real time. Therefore, by sealing the microdroplet container, when the microdroplet container is oblique at an angle of 3 degrees to 5 degrees, the liquid in the microdroplet container can be prevented from flowing out, and the bubbles in the microdroplet container can also be discharged to avoid the bubbles affecting the images in the imaging and detection.

In view of this, the present application provides an oil phase composition for microdroplet generating, including mineral oil and a surfactant. A volume percentage of the mineral oil in the oil phase composition is 88% to 98.5%. The surfactant includes a silicon-oxygen chain non-ionic surfactant containing a chain alkyl group. The oil phase composition for generating the microdroplets, including the mineral oil and the silicon-oxygen chain non-ionic surfactant containing the chain alkyl group, has a density smaller than 1 g/ml, allowing most types of first liquids to be detached from the outlet end of the liquid discharging nozzle and to form the microdroplets falling in the second liquid. The silicon-oxygen chain non-ionic surfactant containing the chain alkyl group can prevent a fusion between the plurality of microdroplets.

In view of this, the present application provides a method for spreading microdroplets, including: S311, providing a microdroplet container, the microdroplet container having an opening, and the microdroplet container containing a second liquid; S312, providing a first liquid, a density of the first liquid being greater than a density of the second liquid, and the first liquid being not miscible with the second liquid; and stacking the plurality of microdroplets generated from the first liquid on a bottom plate of the microdroplet container; S313: temperature cycling the plurality of microdroplets between high and low temperatures until the plurality of microdroplets are spread on the bottom plate. Through the method for spreading microdroplets, the spreading adopts the principle of thermal expansion and thermal contraction. As the temperature changes, the viscosity of the sample droplet decreases and the volume of the sample droplet decreases when the temperature increases. Moreover, the higher the temperature, the lower the viscosity, the softer the sample droplets, so that the plurality of microdroplets are spread on the bottom plate of the microdroplet container, being conducive to imaging and observation.

In view of this, the present application provides a temperature controlling device. The temperature controlling device includes a flexible circuit board, a heating substrate spaced from the flexible circuit board, and a plurality of semiconductor electric couples disposed between the flexible circuit board and the first surface. The heating substrate comprising a first surface and a second surface opposite to each other. The plurality of semiconductor electric couples being connected to each other in series, in parallel, or in combination thereof. The flexible circuit board has characteristics of high wiring density, light weight, small thickness, and good flexibility. The flexible circuit board counteracts the thermal stress with its own deformation during the heating and cooling processes, so that the service life of the temperature controlling device is prolonged. When the nucleic acids in the plurality of microdroplets are amplified in different temperature ranges, the temperature ranges can be rapidly switched within a few seconds via the flexible circuit board, the heating substrate, and the plurality of semiconductor electric couples. The temperature can be increased and decreased instantaneously via the temperature controlling device, thereby accelerating the temperature increasing and decreasing processes to achieve a high-low temperature cycling, reducing the detection time of the digital PCR detection apparatus, and increasing the detection efficiency.

BRIEF DESCRIPTION OF THE DRAWINGS

In order to clearly explain technical solutions of the present application or in prior art, the following drawings, which are to be referred in the description of the embodiments or prior art, are briefly described below. Obviously, the drawings in the following description only show some embodiments of the present application, and those skilled in the art can obtain other drawings according to the following drawings without any creative work.

FIG. 48 is an overall schematic structural view of assembling of a microdroplet container of the present application.

FIG. 49 is a flow chart of a method for spreading microdroplets of the present application.

FIG. 50 is a schematic view of microdroplets stacked on a container bottom plate of the present application.

DETAILED DESCRIPTION

The technical solutions according to the embodiments of the present application are described clearly and completely as follows with reference to the drawings of the embodiments of the present application. It is obvious that the described embodiments are only some but not entire of embodiments of the present application. Other embodiments obtained based on the embodiments of the present application by those skilled in the art without any creative work are all belonged to the protection scope of the present application.

For a clear understanding of the objects, technical solutions, and advantages of the present application, specific embodiments of the present application will now be described in detail with reference to the accompanying drawings. It is to be understood that the following description is merely exemplary embodiment of the present application, and is not intended to limit the scope of the present application.

Figure 1:
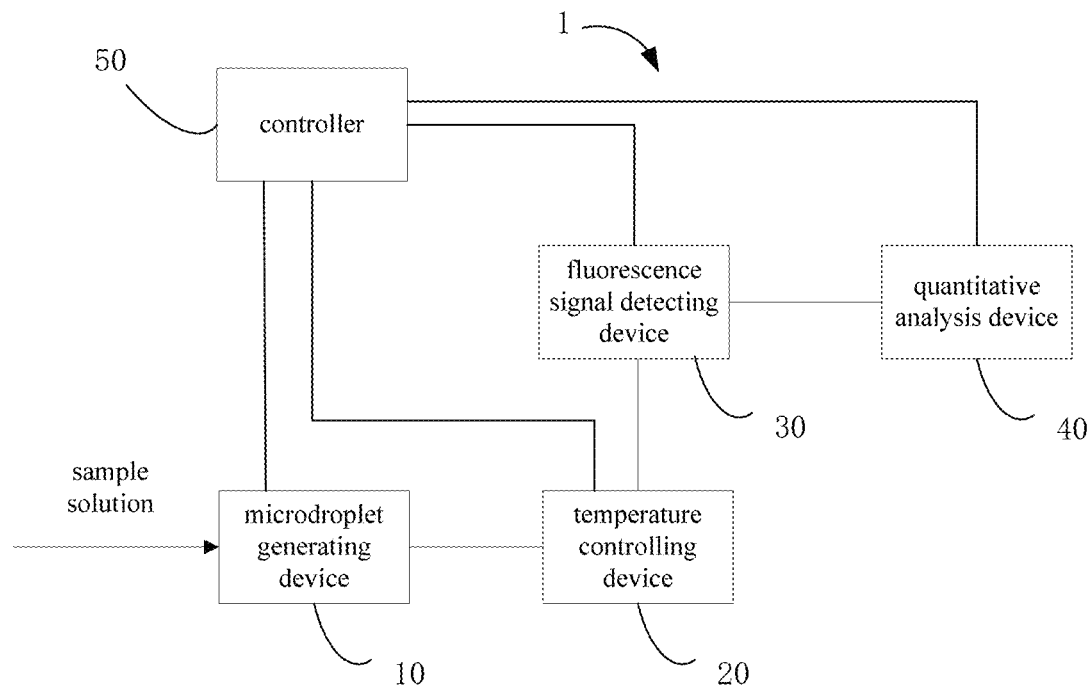
FIG. 1 is an overall schematic structural view of a digital PCR detection apparatus provided by the present application.

Referring to FIG. 1, an embodiment of a digital PCR detection apparatus 1 is provided in the present application. The digital PCR detection apparatus 1 includes a microdroplet generating device 10, a temperature controlling device 20, a fluorescence signal detecting device 30, a quantitative analysis device 40, and a controller 50. The microdroplet generating device 10 is configured to microdropletize a nucleic acid amplification reaction liquid into a plurality of microdroplets. The microdroplet generating device 10 is connected to the temperature controlling device 20 via a rail, so that the plurality of microdroplets can be transferred to the temperature controlling device 20 to undergo a temperature cycling to achieve a nucleic acid amplification. The fluorescence signal detecting device 30 is disposed opposite to the temperature controlling device 20 to photographically detect the plurality of microdroplets after the nucleic acid amplification. The quantitative analysis device 40 communicates with the fluorescence signal detecting device 30 via a data cable to realize transmission of fluorescence information of the plurality of microdroplets and perform a quantitative analysis. The controller 50 is respectively connected to the microdroplet generating device 10, the temperature controlling device 20, the fluorescence signal detecting device 30, and the quantitative analysis device 40, so as to control the microdroplet generating device 10, the temperature controlling device 20, the fluorescence signal detecting device 30, and the quantitative analysis device 40.

The digital PCR detection apparatus 1 can integrate the microdroplet generating device 10, the temperature controlling device 20, the fluorescence signal detecting device 30, and the quantitative analysis device 40, thereby allowing an operator to implement automatic operations. The digital PCR detection apparatus 1 has relatively high working efficiency.

In operation of the digital PCR detection apparatus 1, the microdroplet generating device 10 can form the nucleic acid amplification reaction liquid to be detected into the plurality of microdroplets. The temperature controlling device 20 can amplify the nucleic acids in the plurality of microdroplets. The fluorescence signal detecting device 30 takes images in real time, the images showing variations in fluorescence of the plurality of microdroplets. Fluorescence variation curves of the plurality of microdroplets can be obtained from the images showing variations in fluorescence of the plurality of microdroplets. Ct values of the plurality of microdroplets can be obtained according to the fluorescence variation curves. Moreover, a quantitative analysis can be performed to obtain an initial DNA concentration according to the relationship between the Ct value and an initial copy number. The Ct value refers to the number of the temperature cycles that each microdroplet has undergone when its fluorescence signal reaches a preset threshold.

The nucleic acid amplification reactions for the plurality of microdroplets are carried out in the temperature controlling device 20; and the signals, such as the fluorescence signals, ultraviolet absorption signals, turbidity signals, and so on, of reaction products in the plurality of microdroplets after the nucleic acid amplification reactions are collected by the fluorescence signal detecting device 30. The number of microdroplets in which amplifications of target sequences are achieved can be analyzed by comparing a composition difference between the amplified and non-amplified microdroplets, so that the quantitative analysis of the nucleic acid molecules can be finally achieved. The detection result, obtained by observing the images showing variations in fluorescence of the plurality of microdroplets in real time, is direct, so that the problems of false positive results and false negative results in the plurality of microdroplets can be solved.

The digital PCR detection apparatus 1 integrates the microdroplet generating device 10, the temperature controlling device 20, the fluorescence signal detecting device 30, and the quantitative analysis device 40, allowing the operator to implement automatic operations, so that not only the working efficiency is increased, but also the advantages of rapid reaction, good repeatability, high sensitivity, excellent specificity, and clear result are achieved.

Figure 2:
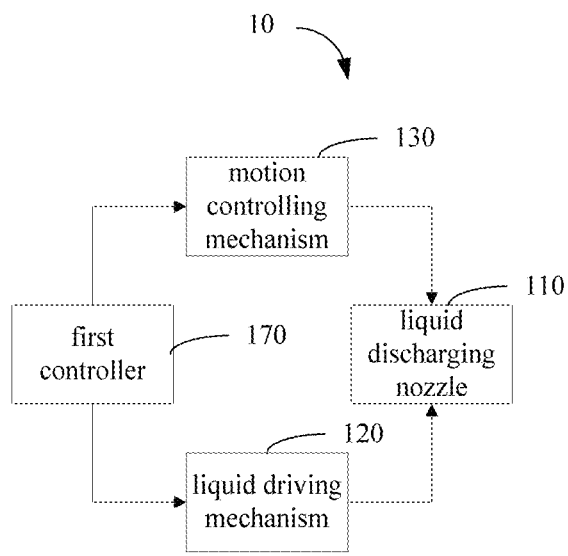
FIG. 2 shows a microdroplet generating device of the digital PCR detection apparatus, provided by the present application.

Referring to FIG. 2, the microdroplet generating device 10 in an embodiment includes a liquid discharging nozzle 110, a liquid driving mechanism 120, a motion controlling mechanism 130, and a first controller 170. The liquid discharging nozzle 110 has an inlet end and an outlet end, and is configured to store a first liquid. The microdroplet generating device 10 can be used in combination with a microdroplet container containing a second liquid therein. The outlet end of the liquid discharging nozzle 110 is inserted below a liquid surface of the second liquid.

The first liquid and the second liquid are immiscible with each other or have an interfacial reaction therebetween. The first liquid and the second liquid can be any two immiscible liquids. In an embodiment of the present application, the first liquid is an aqueous solution, and the second liquid is an oil liquid that is immiscible with water, such as a mineral oil (including n-tetradecane, etc.), a vegetable oil, a silicone oil, a perfluoroalkane oil, and so on; and the generated droplets are aqueous solution droplets. Alternatively, the first liquid is a mineral oil, for example, an organic phase such as tetradecane and n-hexane, and the second liquid is a perfluoroalkane oil that is immiscible with the mineral oil. The first liquid and the second liquid can be two immiscible aqueous phases. In another embodiment of the present application, the first liquid is an aqueous solution, and the second liquid is an aqueous liquid that is immiscible with water. For example, the first liquid is a dextran solution, the second liquid is a polyethylene glycol (PEG) aqueous solution, and the generated droplets are dextran solution droplets.

The first liquid and the second liquid can also be two liquids having an interfacial reaction therebetween. In an embodiment of the present application, the first liquid is a sodium alginate aqueous solution, the second liquid is a calcium oxide aqueous solution with a mass concentration of, for example, 1%. An interfacial reaction exists between the sodium alginate aqueous solution and the calcium oxide aqueous solution, and the generated droplets are calcium alginate gel microspheres. In the present application, a plurality of droplets having different compositions and volumes can be generated in sequence in an open vessel by replacing the liquid discharging nozzle or by changing the composition of the first liquid flowing from the liquid discharging nozzle, so that not only a large batch and high-throughput micro-volume screening can be achieved, but also a multi-step, ultramicro-amount biochemical reaction and detection can be achieved, having a broad prospect of application.

The fluid driving mechanism 120 is connected to the inlet end of the liquid discharging nozzle 110, configured to discharge discharging the first liquid stored in the liquid discharging nozzle 110 from the outlet end of the liquid discharging nozzle 110. The motion controlling mechanism 130 is configured to control the outlet end of the liquid discharging nozzle 110 to move relative to the second liquid in a preset trajectory, or at a preset speed, or with a preset acceleration, so that the first liquid discharged from the outlet end of the liquid discharging nozzle 110 can overcome the surface tension and overcome the adhesion force of the liquid discharging nozzle 110 on the first liquid to form the microdroplet. The first controller 170 is respectively connected to the fluid driving mechanism 120 and the motion controlling mechanism 130 to control the fluid driving mechanism 120 and the motion controlling mechanism 130 to operate cooperatively.

In view of the problem of the microdroplet unstable generation process existing in the conventional liquid discharging nozzle injecting/spraying method, a microdroplet generating method which can stably generate microdroplets is provided.

Figure 3:
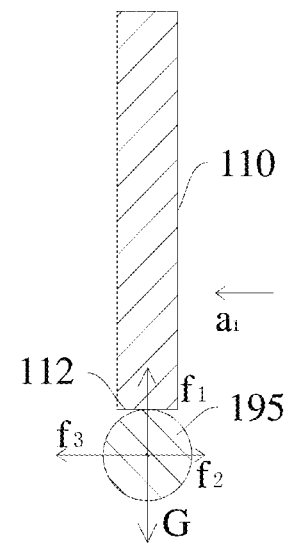
FIG. 3 is a schematic view showing forces applied on a droplet when an outlet end of a liquid discharging nozzle is moving, provided in an embodiment of the present application.

Referring to FIG. 3, in an embodiment of the present application, the motion controlling mechanism 130 can drive the outlet end 112 of the liquid discharging nozzle 110 to move with an instantaneous accelerated motion below the liquid surface of the second liquid, wherein an acceleration value is $a_1$. The first liquid discharged from the outlet end 112 of the liquid discharging nozzle 110 forms a droplet 195 attached to the outlet end 112 of the liquid discharging nozzle 110. The droplet 195 is detached from the outlet end 112 of the liquid discharging nozzle 110 and forms the microdroplet at the moment the outlet end 112 of the liquid discharging nozzle 110 is instantaneously accelerates. The forces exerted upon the microdroplet before the microdroplet is detached from the outlet end 112 of the liquid discharging nozzle 110 are respectively the gravity G, a buoyancy $f_1$ from the second liquid, a viscous resistance $f_2$ from the second liquid, and a maximum adhesion force $f_3$ between the outlet end 112 of the liquid discharging nozzle 110 and the droplet 195. A mass of the microdroplet before being detached from the outlet end 112 of the liquid discharging nozzle 110 is m. The acceleration value of the microdroplet is $a_2$. $m\vec{a}_2 = \vec{G} + \vec{f}_1 + \vec{f}_2 + \vec{f}_3$ is obtained according to Newton's second law of motion.

The maximum adhesion force $f_3$ between the outlet end 112 of the liquid discharging nozzle 110 and the droplet 195 is related to the surface free energy of the liquid discharging nozzle 110, the surface tension of the droplet 195, and the geometric dimension of the liquid discharging nozzle 110. When the outlet end 112 of the liquid discharging nozzle 110 instantaneously accelerates, a direction of the adhesion force applied on the droplet 195 by the outlet end 112 of the liquid discharging nozzle 110 is the same as a direction of the acceleration. The droplet 195 attached to the outlet end 112 of the liquid discharging nozzle 110 is simplified as a sphere. According to the Stokes formula, the viscous resistance $f_2$ exerted upon the droplet 195 moving in the second liquid satisfies $f_2 = 6\pi\eta\, rv$, wherein $\eta$ denotes a viscous coefficient of the second liquid, r denotes a radius of the droplet 195, and v denotes a moving speed of the droplet 195. The speed of the droplet 195 is zero before the outlet end 112 of the liquid discharging nozzle 110 instantaneously accelerates, and thus the viscous resistance $f_2$ exerted upon the droplet 195 by the second liquid at the moment the outlet end 112 of the liquid discharging nozzle 110 instantaneously accelerates is zero or extremely small. In the generation process of the microdroplet, a volume of the droplet 195 is generally in a range from the picoliter magnitude order to the microliter magnitude order, and the buoyancy $f_1$ from the second liquid has a direction opposite to that of the gravity G of the droplet 195; therefore, a vector sum of the buoyancy $f_1$ from the second liquid and the gravity G of the droplet 195 is approximately zero. The viscous resistance $f_2$ is zero or extremely small and the vector sum of the buoyancy $f_1$ and the gravity G is approximately zero, therefore $\vec{G} + \vec{f}_1 + \vec{f}_2 + \vec{f}_3 \approx \vec{f}_3$. According to Newton's second law of motion, when the outlet end 112 of the liquid discharging nozzle 110 instantaneously accelerates, the maximum acceleration value achievable by the droplet 195 in the second liquid is $a_2 \approx f_3/m$, wherein m is the mass of the droplet 195. When the acceleration value $a_2$ of the droplet 195 is smaller than the acceleration value $a_1$ of the outlet end 112 of the liquid discharging nozzle 110, the droplet 195 drops from the outlet end 112 of the liquid discharging nozzle 110 and forms the microdroplet. Thus, the condition for detaching the droplet 195 from the outlet end 112 of the liquid discharging nozzle 110 (i.e. for generating one microdroplet) is roughly $a_2 \approx (f_3/m) < a_1$.

The motion controlling mechanism 130 can accurately control a magnitude of the instantaneous acceleration of the outlet end 112 of the liquid discharging nozzle 110. Therefore, the droplet 195 can be effectively generated from the instantaneous accelerated motion of the outlet end 112 of the liquid discharging nozzle 110 by controlling the outlet end 112 of the liquid discharging nozzle 110 to have a relatively large value of every instantaneous acceleration.

In view of the above, a microdroplet generating method is further provided in the present application. The method includes steps of:

S201, providing the liquid discharging nozzle 110 having the outlet end 112, wherein the first liquid is stored in the liquid discharging nozzle 110; providing a microdroplet container containing the second liquid therein and having an opening, wherein the first liquid and the second liquid are any two immiscible liquids or any two liquids having the interfacial reaction therebetween;

S202, inserting the outlet end 112 of the liquid discharging nozzle 110 below the liquid surface of the second liquid through the opening of the microdroplet container; and S203, controlling the outlet end 112 of the liquid discharging nozzle 110 to move with the motion including the instantaneous accelerated motion below the liquid surface of the second liquid, while discharging the first liquid from the outlet end 112 of the liquid discharging nozzle 110, so that the first liquid discharged from the outlet end 112 of the liquid discharging nozzle 110 forms the droplet 195 attached to the outlet end 112 of the liquid discharging nozzle 110, and the droplet 195 is detached from the outlet end 112 of the liquid discharging nozzle 110 during the instantaneous accelerated motion of the outlet end 112 of the liquid discharging nozzle 110, thereby forming the microdroplet below the liquid surface of the second liquid.

In the above microdroplet generating method, for the reason that the outlet end 112 of the liquid discharging nozzle 110 makes a relatively large value of the instantaneous acceleration, the adhesion force between the droplet 195 attached to the outlet end 112 of the liquid discharging nozzle 110 and the outlet end 112 of the liquid discharging nozzle 110 is insufficient to let the droplet 195 synchronously accelerate with the outlet end 112 of the liquid discharging nozzle 110, so that the droplet 195 attached to the outlet end 112 of the liquid discharging nozzle 110 is detached from the liquid discharging nozzle 110, and formed into the microdroplet below the liquid surface of the second liquid. In the microdroplet generating method provided in the present application, the outlet end 112 of the liquid discharging nozzle 110 generates the microdroplet at the moment the outlet end 112 instantaneously accelerates below the liquid surface of the second liquid, which reduces the disturbance to the second liquid when the outlet end 112 of the liquid discharging nozzle 110 moves, and ensures the stability of the microdroplet generation.

Optionally, in step S203, the manner in which the first liquid is discharged from the outlet end 112 of the liquid discharging nozzle 110 can be a continuous discharge or a discontinuous discharge. The specific discharge manner can be designed according to the actual operating conditions. In this embodiment, in step S203, the first liquid is continuously discharged from the outlet end 112 of the liquid discharging nozzle 110, so that every instantaneous accelerated motion of the outlet end 112 of the liquid discharging nozzle 110 can be fully utilized to generate the microdroplet.

In an embodiment, in step S203, the first liquid is discharged from the outlet end 112 of the liquid discharging nozzle 110 at a constant flow rate; that is, the volumes of the first liquid discharged from the outlet end 112 of the liquid discharging nozzle 110 in equal time intervals are always equal to each other. The discharging of the first liquid at the constant flow rate from the outlet end 112 of the liquid discharging nozzle 110 is beneficial for realizing the controlling of the microdroplet generation through controlling the motion of the outlet end 112 of the liquid discharging nozzle 110.

In an embodiment of the present application, in the step S203, the outlet end 112 of the liquid discharging nozzle 110 makes a periodic motion including the instantaneous accelerated motion below the liquid surface of the second liquid. When the outlet end 112 of the liquid discharging nozzle 110 periodically moves below the liquid surface of the second liquid, the displacement, the velocity, and the acceleration of the outlet end 112 of the liquid discharging nozzle 110 are periodically changed. The microdroplets can be generated at equal time intervals from the periodic motion including the instantaneous accelerated motions in combination with the discharge of the first liquid from the outlet end 112 of the liquid discharging nozzle 110 at a constant flow rate. Alternatively, the first liquid is discharged from the outlet end 112 of the liquid discharging nozzle 110 at a varied flow rate, while the volume of the first liquid discharged from the outlet end 112 of the liquid discharging nozzle 110 is constant in every motion period of the outlet end 112 of the liquid discharging nozzle 110, so as to ensure that, before the outlet end 112 of the liquid discharging nozzle 110 instantly accelerates each time, the droplet 195 has the same volume, thereby generating microdroplets with an uniform volume.

The surface free energy of the liquid discharging nozzle 110, the geometric dimension of the liquid discharging nozzle 110, and the surface tension of the droplet 195, as factors which affect the maximum adhesion force $f_3$ between the outlet end 112 of the liquid discharging nozzle 110 and the droplet 195, are determined if the liquid discharging nozzle 110 and the first liquid are not changed. Therefore, the maximal value $f_3$ of the adhesion force between the outlet end 112 of the liquid discharging nozzle 110 and the droplet 195 is fixed if the liquid discharging nozzle 110 and the first liquid are not changed. The fluid driving mechanism 120 can drive the first liquid to be continuously discharged from the outlet end 112 of the liquid discharging nozzle 110 at a uniform flow rate. The motion controlling mechanism 130 can accurately control the moment at which the outlet end 112 of the liquid discharging nozzle 110 makes an accelerated motion with the instantaneous acceleration value $a_1$ and accurately control the magnitude of the instantaneous acceleration value $a_1$. Under the cooperation of the fluid driving mechanism 120 and the motion controlling mechanism 130, it is easy to drive the outlet end 112 of the liquid discharging nozzle 110 to instantaneously accelerate with the acceleration value $a_1$ at the moment the volume of the droplet 195 reaches the set value, so as to generate the microdroplets with the uniform volume. If the first liquid is evenly and continuously discharged from the outlet end 112 of the liquid discharging nozzle 110 under the control of the fluid driving mechanism 120, the microdroplets with the uniform volume can be generated by only driving the outlet end 112 of the liquid discharging nozzle 110 to make the instantaneous accelerated motions at the equal time intervals via the motion controlling mechanism 130.

The surface free energy of the liquid discharging nozzle 110 and the geometric dimension of the liquid discharging nozzle 110, as two factors which affect the maximum adhesion force $f_3$ between the outlet end 112 of the liquid discharging nozzle 110 and the droplet 195, are varied if multiple liquid discharging nozzles 110 are used to generate the microdroplets simultaneously or in sequence. However, the variation of the surface free energy of liquid discharging nozzles 110 and the geometric dimensions of the liquid discharging nozzles 110 can be controlled within a certain range via batch processing. The surface tension of the droplet 195, as another factor that affects the maximum adhesion force $f_3$ between the outlet end 112 of the liquid discharging nozzle 110 and the droplet 195, is also varied within a very small range. Therefore, the maximum value $f_3$ of the adhesion force between the outlet end 112 of the liquid discharging nozzle 110 and the droplet 195 fluctuates within a very small range. The fluid driving mechanism 120 can drive the first liquid to be continuously discharged from the outlet end 112 of the liquid discharging nozzle 110 at a uniform flow rate. The motion controlling mechanism 130 can accurately control the moment, at which the outlet end 112 of the liquid discharging nozzle 110 accelerates with the instantaneous acceleration value $a_1$, and accurately control the magnitude of the instantaneous acceleration value $a_1$. Under the cooperation of the fluid driving mechanism 120 and the motion controlling mechanism 130, it is easy to drive the outlet end 112 of the liquid discharging nozzle 110 to make the instantaneous accelerated motions with the acceleration value $a_1$ at the moments the volumes of the droplets 195 reach the set value, so as to generate the microdroplets with the uniform volume. If the first liquid is evenly and continuously discharged from the outlet end 112 of the liquid discharging nozzle 110 under the control of the fluid driving mechanism 120, the microdroplets with the uniform volume can be generated by only driving the outlet end 112 of the liquid discharging nozzle 110 to make the instantaneous accelerated motions at the equal time intervals via the motion controlling mechanism 130.

While the fluid driving mechanism 120 discharges the first liquid evenly from the outlet end 112 of the liquid discharging nozzle 110, the motion controlling mechanism 130 cooperatively drives the outlet end 112 to make the instantaneous accelerated motion with a relatively large acceleration value at the moment the volume of the droplet 195 reaches the set value. The microdroplet generating method provided in the present application can ensure not only a volume uniformity of the microdroplets generated by using the same liquid discharging nozzle 110, but also a volume uniformity of the microdroplets generated simultaneously or in sequence by using a plurality of the liquid discharging nozzles 110. The microdroplet generating method provided in this embodiment can increase the generating efficiency by using a plurality of the liquid discharging nozzles 110 to generate the microdroplets at the same time while ensuring the uniformity of the volumes of the microdroplets.

In an embodiment, under the control of the motion controlling mechanism 130, one period of motion of the outlet end 112 of the liquid discharging nozzle 110 includes multiple instantaneous accelerated motions having the same acceleration value; and the one period of motion of the outlet end 112 of the liquid discharging nozzle 110 is equally divided by the multiple instantaneous accelerated motions. Due to the multiple instantaneous accelerated motions included in one period of motion of the outlet end 112 of the liquid discharging nozzle 110, a plurality of microdroplets can be generated in the same period of motion of the outlet end 112 of the liquid discharging nozzle 110. Optionally, in the step S203, the moving trajectory of the outlet end 112 of the liquid discharging nozzle 110 below the liquid surface of the second liquid includes one or a combination of various trajectories such as a straight line segment, an arc-shaped line segment, or a polygon. As an implementation manner, when one period of motion of the outlet end 112 of the liquid discharging nozzle 110 includes two instantaneous accelerated motions, the moving trajectory of liquid discharging nozzle 110 is a straight line or an arc. When one period of motion of the outlet end 112 of the liquid discharging nozzle 110 includes more than two instantaneous accelerated motions, the moving trajectory of the outlet end 112 of the liquid discharging nozzle 110 in the second liquid is a regular polygon such as a regular triangle, a square, a regular pentagon, a regular hexagon, and so on.

Figure 4:
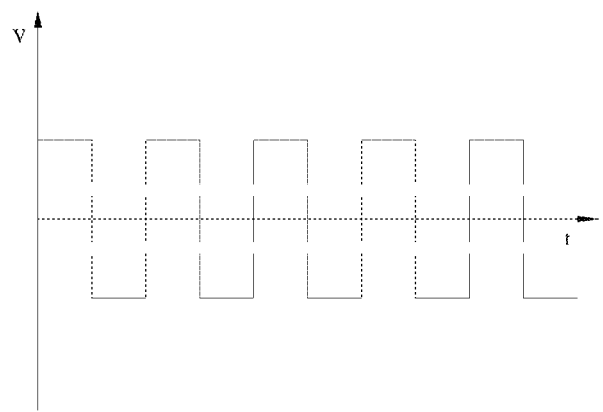
FIG. 4 is a schematic view of a velocity variation of an outlet end of a liquid discharging nozzle, provided by an embodiment of the present application.

As an implementation manner, in the step S203, during the periodic motion of the outlet end 112 of the liquid discharging nozzle 110 below the liquid surface of the second liquid, the speed of the outlet end 112 of the liquid discharging nozzle 110 varies in the form of a rectangular wave. Since the outlet end 112 of the liquid discharging nozzle 110 has its speed varied in the form of the rectangular wave, it enters into a constant speed phase immediately after the acceleration phase, which is favorable for the motion controlling mechanism 130 to accurately control the motion state of the outlet end 112 of the liquid discharging nozzle 110. Optionally, in the rectangular wave indicating the variation of the moving speed of the outlet end 112 of the liquid discharging nozzle 110, the time period of the high level of the wave and the time period of the low level of the wave can be the identical or different. Furthermore, in the step S203, during the periodic motion of the outlet end 112 of the liquid discharging nozzle 110 below the liquid surface of the second liquid, the speed of the outlet end 112 of the liquid discharging nozzle 110 varies in the form of a square wave. In the square wave indicating the variation of the moving speed of the outlet end 112 of the liquid discharging nozzle 110, the time period of the high level of the wave and the time period of the low level of the wave are identical. At the low level of the rectangular wave indicating the variation of the moving speed of the outlet end 112 of the liquid discharging nozzle 110, the speed of the outlet end 112 of the liquid discharging nozzle 110 is zero, or the velocity has a direction opposite to the direction of the velocity at the high level. Referring to FIG. 4, in an embodiment, the velocities of the outlet end 112 of the liquid discharging nozzle 110 in the first half and in the second half of the period of motion of the outlet end 112 of the liquid discharging nozzle 110 have the same magnitude but opposite directions. There are two instantaneous accelerated motions with opposite directions in one period of motion of the outlet end 112 of the liquid discharging nozzle 110.

In an embodiment, the moving trajectory of the outlet end 112 of the liquid discharging nozzle 110 below the liquid surface of the second liquid is a straight line segment. The outlet end 112 of the liquid discharging nozzle 110 makes one instantaneous accelerated motion at one endpoint of the straight line segment and makes another instantaneous accelerated motion in the opposite direction at the other endpoint of the straight line segment. The acceleration values of the two instantaneous accelerated motions are both $a_1$. In another embodiment, the moving trajectory of the outlet end 112 of the liquid discharging nozzle 110 below the liquid surface of the second liquid is an arc or a polygon. Furthermore, in the step S203, the outlet end 112 of the liquid discharging nozzle 110 periodically moves below the liquid surface of the second liquid with a frequency between 0.1 Hz to 200 Hz, which is easy to realize in practice.

Figure 5:
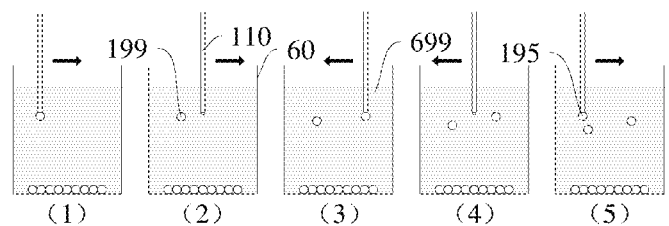
FIG. 5 is a schematic view of a generating process of microdroplets when the outlet end of the liquid discharging nozzle is moving, provided by an embodiment of the present application.

Referring to FIGS. 4 and 5, in a specific embodiment of the present application, the first liquid is discharged from the outlet end 112 of the liquid discharging nozzle 110 at a constant flow rate under the control of the liquid driving mechanism 120. The outlet end of the liquid discharging nozzle 110 periodically moves along a moving trajectory of a straight line and at a speed varying in the form of a square wave under the control of the motion controlling mechanism 130. The instantaneous acceleration of the outlet end 112 of the liquid discharging nozzle 110 reaches its maximum value at the moment the direction of the velocity of the outlet end 112 of the liquid discharging nozzle 110 changes. The droplet 195 attached to the outlet end 112 of the liquid discharging nozzle 110 is detached from the outlet end 112 of the liquid discharging nozzle 110 to form the microdroplet 199 at the moment the instantaneous acceleration of the outlet end 112 of the liquid discharging nozzle 110 reaches its maximum value. Since the first liquid is discharged from the outlet end 112 of the liquid discharging nozzle 110 at the constant flow rate, at the moment the droplet 195 is detached from the outlet end 112 of the liquid discharging nozzle 110, a new droplet 195 enters a generation state. When the outlet end 112 of the liquid discharging nozzle 110 accelerates again in the opposite direction, the newly generated droplet 195 drops from the outlet end 112 of the liquid discharging nozzle 110, forming a new microdroplet 199.

In this embodiment, two microdroplets 199 can be generated in one period of motion of the outlet end 112 of the liquid discharging nozzle 110, and the square wave is easy to be achieved in practice. In another embodiment, one microdroplet 199 is generated in one period of motion of the outlet end 112 of the liquid discharging nozzle 110. Optionally, in an embodiment, the outlet end 112 of the liquid discharging nozzle 110 moves along a straight line trajectory in any direction at a speed varying in a square wave form in the second liquid 699, for example, the outlet end moves at a speed varying in the square wave form along a straight line trajectory in a plane perpendicular to an extending direction of the liquid discharging nozzle 110, moves at a speed varying in the square wave form along a straight line trajectory in any plane angularly disposed relative to the extending direction of the liquid discharging nozzle 110, or moves at a speed varying in the square wave form along a straight line trajectory in the extending direction of the liquid discharging nozzle 110, etc. In other embodiments of the present application, when the moving trajectory of the outlet end 112 of the liquid discharging nozzle 110 is an arc or a polygon, the outlet end 112 of the liquid discharging nozzle 110 moves at a speed varying in the square wave form along an arc-shaped trajectory or a polygonal trajectory in any direction in the second liquid 699, for example, the outlet end moves at a speed varying in the square wave form along an arc-shaped trajectory or a polygonal trajectory in a plane perpendicular to the extending direction of the liquid discharging nozzle 110, or moves at a speed varying in the square wave form along an arc-shaped trajectory or a polygonal trajectory in any plane angularly disposed relative to the extending direction of the liquid discharging nozzle 110, or moves at a speed varying in the square wave form along an arc-shaped trajectory or a polygonal trajectory in the extending direction of the liquid discharging nozzle 110, etc.

Figure 6:
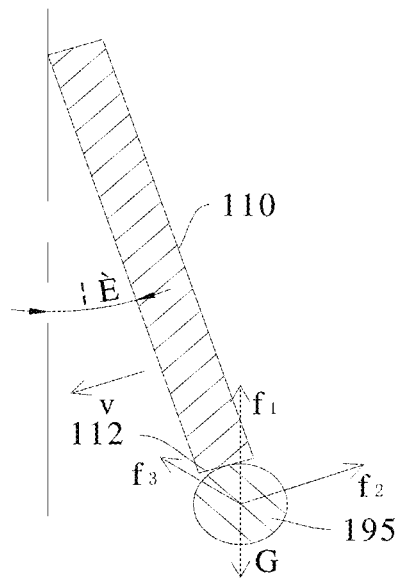
FIG. 6 is a schematic view of forces applied on a droplet when an outlet end of a liquid discharging nozzle is moving, provided by another embodiment of the present application.

In an embodiment of the present application, driven by the motion controlling mechanism 130, the outlet end 112 of the liquid discharging nozzle 110 moves at a periodically changed speed blow the liquid surface of the second liquid. The speed of the outlet end 112 of the liquid discharging nozzle 110 changes monotonously in both the first half period and the second half period of the speed variation. The monotonously changing means that the speed of the outlet end 112 of the liquid discharging nozzle 110 at a subsequent moment is always greater than or equal to (or, less than or equal to) the speed at a previous moment in the first half period or the second half period the speed variation. For example, during the first half period of the speed variation, the speed of the outlet end 112 of the liquid discharging nozzle 110 continuously increases, or the speed continuously increases in some time periods and remains unchanged in some other time periods. Correspondingly, during the second half period of the speed variation, the speed of the outlet end 112 of the liquid discharging nozzle 110 continuously decreases, or the speed continuously decreases in some time periods and remains unchanged in some other time periods. The first liquid discharged from the outlet end 112 of the liquid discharging nozzle 110 is formed into a droplet 195 attached to the outlet end 112 of the liquid discharging nozzle 110. The droplet 195 is detached from the outlet end 112 of the liquid discharging nozzle 110, and the microdroplet 199 is formed at the moment the moving speed of the outlet end 112 of the liquid discharging nozzle 110 reaches a set value. Referring to FIG. 6, the forces exerted upon the microdroplet 199, before the microdroplet 199 is detached from the outlet end 112 of the liquid discharging nozzle 110, are respectively the gravity G, a buoyancy $f_1$ from the second liquid 699, a viscous resistance force $f_2$ from the second liquid 699, and a maximum adhesion force $f_3$ between the outlet end 112 of the liquid discharging nozzle 110 and the droplet 195. The microdroplet 199 has a mass m, a speed v, and an acceleration $a_2$ before the microdroplet 199 is detached from the outlet end 112 of the liquid discharging nozzle 110. During moving in the second liquid 699, the droplet 195 is under a combined action of the viscous force $f_2$, the gravity G, the buoyancy $f_1$, and the adhesion force $f_3$, namely $m\vec{a}_2 = \vec{f}_1 + \vec{G} + \vec{f}_2 + \vec{f}_3$. The condition for detaching the droplet 195 from the outlet end 112 of the liquid discharging nozzle 110 (i.e., for generating one microdroplet 199) is $|\vec{f}_3| < |\vec{f}_1 + \vec{G} + \vec{f}_2 - m\vec{a}_2|$.

The maximum value $f_3$ of the adhesion force between the outlet end 112 of the liquid discharging nozzle 110 and the droplet 195 is related to the surface free energy of the liquid discharging nozzle 110, the surface tension of the droplet 195, and the geometric dimension of the liquid discharging nozzle 110. The droplet 195 attached to the outlet end 112 of the liquid discharging nozzle 110 is simplified as a sphere. According to the Stokes formula, the viscous resistance force $f_2$ applied on the droplet 195 moving in the second liquid 699 satisfies $f_2 = 6\pi\eta rv$, wherein $\eta$ denotes a viscous coefficient of the second liquid 699, r denotes a radius of the droplet 195, and v denotes a velocity of the droplet 195. In the process of generating the microdroplet 199, a volume of droplet 195 is generally in a range from picoliter magnitude order to microliter magnitude order, and the viscosity coefficient of the second liquid 699 is commonly relatively large. Therefore, generally, $|\vec{f}_2| \gg |\vec{G}|$, $|\vec{f}_2| \gg |\vec{f}_1|$ and $|\vec{f}_2| \gg |m\vec{a}_2|$. Therefore, when the outlet end 112 of the liquid discharging nozzle 110 periodically moves at a changing velocity below the liquid surface of second liquid 699, the condition for detaching the droplet 195 from the outlet end 112 of the liquid discharging nozzle 110 (i.e., for generating one microdroplet 199) is approximately $|\vec{f}_3| < |\vec{f}_2|$.

Based on this, the present application provides a microdroplet generating method, including the following steps:

S211, providing the liquid discharging nozzle 110 having the outlet end 112, wherein the first liquid is stored in the liquid discharging nozzle 110; providing a microdroplet container 60 containing the second liquid 699 therein, the microdroplet container 60 having an opening; wherein the first liquid and the second liquid 699 are any two immiscible liquids or any two liquids having an interfacial reaction therebetween;

S212, inserting the outlet end 112 of the liquid discharging nozzle 110 below the liquid surface of the second liquid 699 through the opening of the microdroplet container 60;

S213, controlling the outlet end 112 of the liquid discharging nozzle 110 to move at a periodically changed speed below the liquid surface of the second liquid 699, and in the first half period and the second half period of the speed variation, the speed of the outlet end 112 of the liquid discharging nozzle 110 changes monotonously, while the first liquid is discharged at a constant flow rate from the outlet end 112 of the liquid discharging nozzle 110, and the first liquid discharged from the outlet end 112 of the liquid discharging nozzle 110 is formed into the droplet 195 attached to the outlet end 112 of the liquid discharging nozzle 110, then the droplet 195 is detached from the outlet end 112 of the discharging nozzle 110 during the moving of the outlet end 112 of the liquid discharging nozzle 110, thereby forming the microdroplet 199 below the liquid surface of the second liquid 699.

In the microdroplet generating method above, the outlet end 112 of the liquid discharging nozzle 110 makes a motion with a periodically changed speed blow the liquid surface of the second liquid 699. The speed of the outlet end 112 of the liquid discharging nozzle 110 change monotonously in both the first half period and the second half period of the speed variation. During the movement, the viscous force $f_2$ exerted upon the droplet 195 by the second liquid 699 also shows a periodic change in accordance with the periodically changed speed of the outlet end 112 of liquid discharging nozzle 110. When the maximum adhesion force $f_3$ between the outlet end 112 of the liquid discharging nozzle 110 and the droplet 195 is smaller than the viscous force $f_2$ exerted on the droplet 195 by the second liquid 699, the droplet 195 cannot move synchronously with the outlet end 112 of the liquid discharging nozzle 110, so that the droplet 195 attached to the outlet end 112 of the discharging nozzle 110 is detached from the outlet end 112 of the liquid discharging nozzle 110 to form the microdroplet 199 below the liquid surface of the second liquid 699. In the microdroplet generating method provided in the present application, the outlet end 112 of the liquid discharging nozzle 110 makes a periodic motion with a varying velocity below the liquid surface of the second liquid 699 to generate the microdroplet 199, which reduces the disturbance to the second liquid when the outlet end 112 of the liquid discharging nozzle 110 moves, and ensures the stability of the generation of the microdroplet 199.

In this embodiment, in step S213, the first liquid is continuously discharged from the outlet end 112 of the liquid discharging nozzle 110. Further, in step S213, the first liquid is discharged from the outlet end 112 of the liquid discharging nozzle 110 at a constant flow rate, meaning that the volumes of the first liquid discharged from the outlet end 112 of the liquid discharging nozzle 110 in equal time intervals are always equal to each other. The discharging of the first liquid at the constant flow rate from the outlet end 112 of the liquid discharging nozzle 110 is beneficial for realizing the controlling of the generation of the microdroplets 199 to have the uniform volume through controlling the periodic motion of the outlet end 112 of the liquid discharging nozzle 110.

Among the factors that affect the viscous resistance force $f_2$ applied on the droplet 195 moving in the second liquid 699, the moving speed v of the droplet 195 can be controlled more easily. The droplet 195 synchronously moves with the outlet end 112 of the liquid discharging nozzle 110 till the droplet 195 is detached from the outlet end 112 of the liquid discharging nozzle 110 to form the microdroplet 199. Therefore, the moving speed v of the droplet 195 can be accurately controlled by controlling the moving speed of the outlet end 112 of the liquid discharging nozzle 110. The first liquid is controlled to be discharged at the uniform flow rate from the outlet end 112 of the liquid discharging nozzle 110, thus the radius r of the droplet 195 also exhibits a periodic change in a set time interval. Among the factors that affect the viscous resistance force $f_2$ applied on the droplet 195 when the droplet 195 moves in the second liquid 699, the viscosity coefficient q of the second liquid 699 will vary within a certain scope in use, but the varying scope of the viscosity coefficient q of the second liquid 699 is very small.

The surface free energy of the liquid discharging nozzle 110, the geometric dimension of the liquid discharging nozzle 110, and the surface tension of the droplet 195, as the factors affecting the maximum adhesion force $f_3$ between the outlet end 112 of the liquid discharging nozzle 110 and the droplet 195, are determined if the liquid discharging nozzle 110 and the first liquid are not changed. Therefore, the maximum value $f_3$ of the adhesion force between the outlet end 112 of the liquid discharging nozzle 110 and the droplet 195 is fixed if the liquid discharging nozzle 110 and the first liquid are not changed. The surface free energy of the liquid discharging nozzle 110 and the geometric dimension of the liquid discharging nozzle 110, as two factors affecting the maximum adhesion force $f_3$ between the outlet end 112 of the liquid discharging nozzle 110 and the droplet 195, are varied if multiple liquid discharging nozzles 110 are used to generate the microdroplets 199 simultaneously or in sequence. However, the variation of the surface free energies of liquid discharging nozzles 110 and the geometric dimensions of the liquid discharging nozzles 110 can be controlled within a certain range via batch processing. The surface tension of the droplet 195, as another factor affecting the maximum adhesion force $f_3$ between the outlet end 112 of the liquid discharging nozzle 110 and the droplet 195, also varies within a very small range. Therefore, the maximum adhesion force $f_3$ between the outlet end 112 of the liquid discharging nozzle 110 and the droplet 195 fluctuates within a very small range.

Therefore, it only needs to control the viscous resistance force $f_2$ applied on the droplet 195 moving in the second liquid 699 to be greater than the range of the maximum adhesion force value $f_3$ between the outlet end 112 of the liquid discharging nozzle 110 and the droplet 195. In the generation process of the microdroplets 199 of the same batch, the droplets 195 should have same radius r. Once the experimental parameters are determined, the radius r of the droplet 195 is also determined accordingly. The outlet end 112 of the liquid discharging nozzle 110 moves at the varying speed below the liquid surface of the second liquid 699. When the moving speed of the outlet end 112 of the liquid discharging nozzle 110 below the liquid surface of the second liquid 699 satisfies $v > f_3/6\pi\eta r$, the droplet 195 is detached from the outlet end 112 of the liquid discharging nozzle 110 to form the microdroplet 199.

The outlet end 112 of the liquid discharging nozzle 110 moves at the periodically changed speed below the liquid surface of the second liquid 699. By controlling the first liquid to be discharged from the outlet end 112 of the liquid discharging nozzle 110 at the uniform flow rate, the volume of the droplet 195 attached to the outlet end 112 of the liquid discharging nozzle 110 also uniformly increases. At the moment the microdroplet 199 is detached from the outlet end 112 of the liquid discharging nozzle 110, the radius of the microdroplet 199 is called the critical radius, and the speed of the microdroplet 199 is called the critical speed. The motion period of the outlet end 112 of the liquid discharging nozzle 110 and the flow rate, at which the first liquid is discharged from the outlet end 112 of the liquid discharge nozzle 110, are adjusted to allow the droplets 195 attached to the outlet end 112 of the liquid discharging nozzle 110 reach the critical radius and the critical speed after equal time intervals (in multiple motion periods of the outlet end 112 of the liquid discharging nozzle 110), thus forming the new microdroplets 199. Since the first liquid is discharged from the outlet end 112 of the liquid discharging nozzle 110 at the uniform flow rate, the volume values of the generated microdroplets 199 are identical.

As an implementation manner, in step S213, the speed of the outlet end 112 of the liquid discharging nozzle 110 is center symmetrical relative to the midpoint which is the middle time point of the period of the speed variation. Further, in step S213, the acceleration, the velocity, and the moving trajectory of the outlet end 112 of the liquid discharging nozzle 110 below the liquid surface of the second liquid 699 are periodically changed. Furthermore, in step S213, the speed of the outlet end 112 of the liquid discharging nozzle 110 below the liquid surface of the second liquid 699 varies in a form of a cosine curve.

Optionally, in step S213, the moving trajectory of the outlet end 112 of the liquid discharging nozzle 110 below the liquid surface of the second liquid 699 includes one of or a combination of various trajectories such as a straight line segment, an arc-shaped line segment, or a polygon. In step S213, the frequency of the periodic motion of the outlet end 112 of the liquid discharging nozzle 110 below the liquid surface of the second liquid 699 is between 0.1 Hz and 200 Hz, which can easily be realized in practice.

Figure 7:
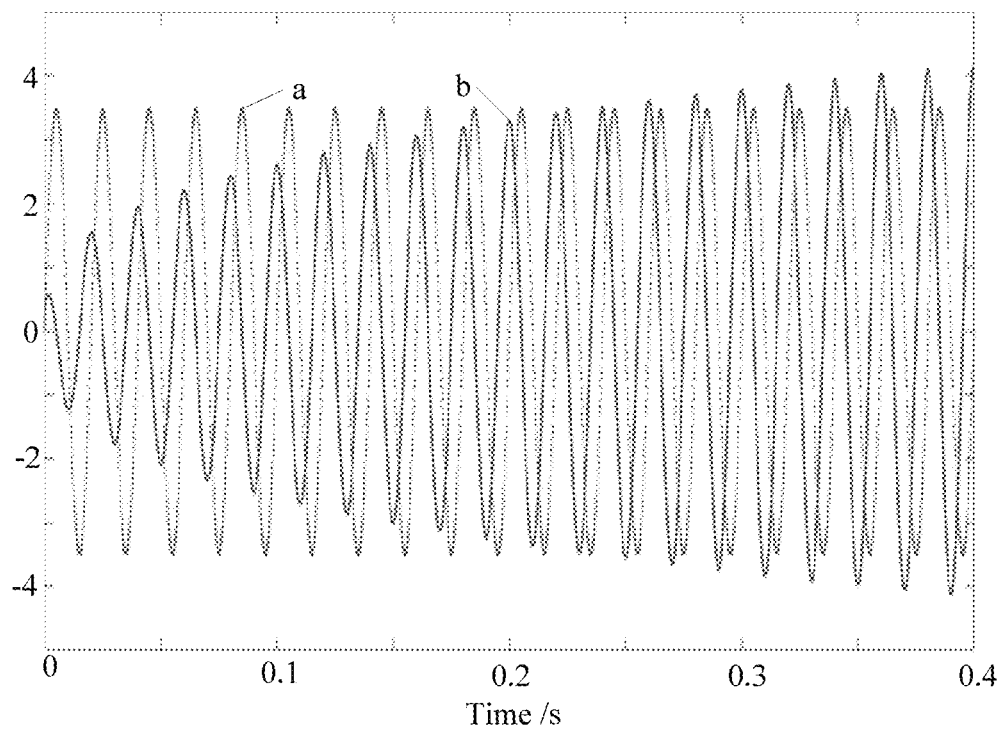
FIG. 7 is a schematic view of an ideal change of viscosity resistance force applied on a droplet moving with an outlet end of a liquid discharging nozzle, provided by an embodiment of the present application.

Taking the periodic motion of the outlet end 112 of the liquid discharging nozzle 110 below the liquid surface of the second liquid 699 as an example, the periodic motion has an arc trajectory with a speed changing in the cosine form, and the outlet end 112 of the liquid discharging nozzle 110 actually makes a swing motion with a displacement that can be represented by a sine curve as the curve a shown in FIG. 7. Driven by the liquid driving mechanism, the first liquid is discharged from the outlet end 112 of the liquid discharging nozzle 110 at a uniform flow rate. Assuming that the droplet 195 is not detached from the outlet end 112 of the liquid discharging nozzle 110, the viscosity resistance force $f_2$, changing with time and applied on the droplet 195 moving in the second liquid 699, is represented by the curve b in FIG. 7 obtained through calculation. At an initial stage of the discharge of the first liquid from the outlet end 112 of the liquid discharging nozzle 110 at the uniform flow rate, the radius r of the droplet 195 significantly increases with the volume increase of the droplet 195. As the radius r of the droplet 195 continues to increase, the uniform volume increase of the droplet 195 will only result in a slow increase of the radius r of the droplet 195. Therefore, the maximum viscous resistance force $f_2$ applied on the droplet 195 moving in the second liquid 699 increases rapidly at first and then the increase gradually slows down during the first few swing periods of the outlet end 112 of the liquid discharging nozzle 110. As shown in FIG. 7, the viscous resistance force $f_2$ applied on the droplet 195 moving in the second liquid 699 also shows a periodic feature similar to the periodic motion of the outlet end 112 of the liquid discharging nozzle 110; that is, the viscous resistance force $f_2$ applied on the droplet 195 moving in the second liquid 699 varies with the speed of the outlet end 112 of the liquid discharging nozzle 110. In the actual working condition, the droplet 195 is detached from the outlet end 112 of the liquid discharging nozzle 110 at the moment the viscosity resistance force $f_2$ applied on the droplet 195 moving in the second liquid 699 increases to the value greater than the maximum adhesion force $f_3$ between the outlet end 112 of the liquid discharging nozzle 110 and the droplet 195, forming the microdroplet 199.

Figure 8:
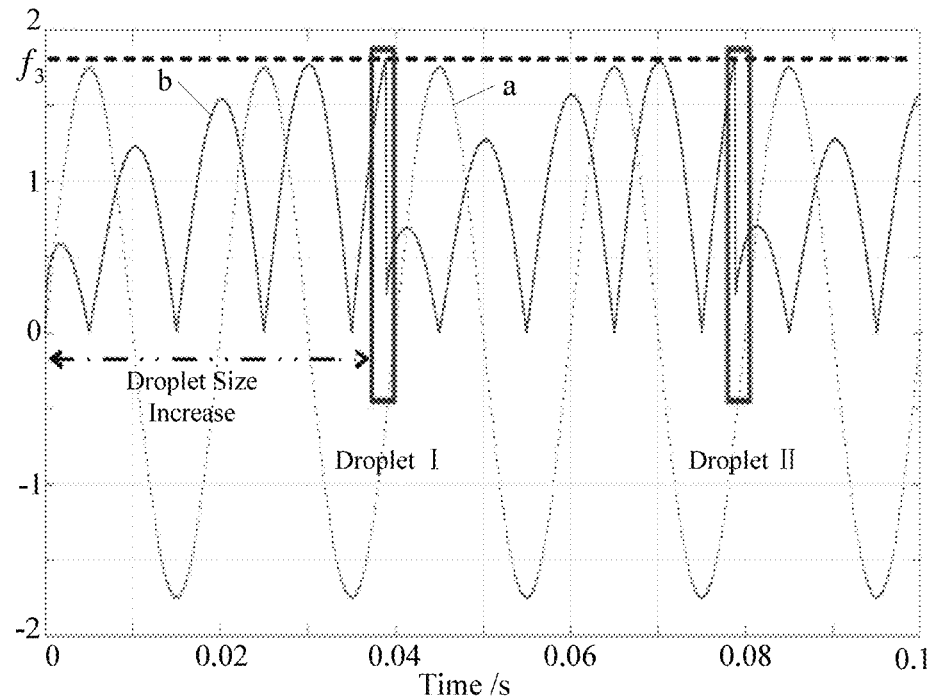
FIG. 8 is a schematic view of a process of generating one microdroplet in every two moving cycles of an outlet end of a liquid discharging nozzle, provided by an embodiment of the present application.

In an embodiment of the present application, referring to FIG. 8, the outlet end 112 of the liquid discharging nozzle 110 is controlled to swing along a circular arc trajectory with a displacement changing in a sine form. In a case that the liquid discharging nozzle 110 and the first liquid are not changed, the maximum value $f_3$ of the adhesion force between the outlet end 112 of the liquid discharging nozzle 110 and the droplet 195 is fixed. The viscous resistance force $f_2$ applied on the droplet 195 moving in the second liquid 699 continuously increases with the increase of the radius r of the droplet 195 attached to the outlet end 112 of the liquid discharging nozzle 110. At the moment the viscous resistance force $f_2$ applied on the droplet 195 moving in the second liquid 699 is greater than the maximum adhesion force $f_3$ between the outlet end 112 of the liquid discharging nozzle 110 and the droplet 195, the droplet 195 is detached from the outlet end 112 of the liquid discharging nozzle 110 and forms the microdroplet 199 which is the droplet I in FIG. 8. Then the next generation cycle of the microdroplet 199 begins.

In this embodiment, the maximum adhesion force $f_3$ between the outlet end 112 of the liquid discharging nozzle 110 and the droplet 195 is $f_3=1.8\times10^{-4}$ N, and the swing frequency of the outlet end 112 of the liquid discharging nozzle 110 is 50 Hz. The first microdroplet 199 (the droplet I in FIG. 8) is generated at the end of the second period of the swing motion of the outlet end 112 of the liquid discharging nozzle 110 whose displacement changes in a sine form. In the initial stage of the generation of the second microdroplet 199, as the radius r of the droplet 195 attached to the outlet end 112 of the liquid discharging nozzle 110 increases fast, the viscous resistance force $f_2$ applied on the droplet 195 moving in the second liquid 699 does not immediately decrease but increases slightly, even though the moving speed of the outlet end 112 of the liquid discharging nozzle 110 decreases at this stage. After that, the radius r of the droplet 195 slowly increases, and the viscous resistance force $f_2$ applied on the droplet 195 moving in the second liquid 699 mainly changes with the moving speed of the outlet end 112 of the liquid discharging nozzle 110.

The first liquid is controlled to be discharged from the outlet end 112 of the liquid discharging nozzle 110 at the uniform flow rate, so that a new droplet 195 (the droplet II in FIG. 8) having the volume equal to that of the previous microdroplet 199 is generated again at the outlet end 112 of the liquid discharging nozzle 110 at the moment two motion periods passed right after the generation of the previous microdroplet 199. Moreover, the moving speed of the outlet end 112 of the liquid discharging nozzle 110 at this moment is also the same as that two motion periods ago. The new droplet 195 having the same volume as the previous microdroplet 199 is detached from the outlet end 112 of the liquid discharging nozzle 110. The uniformity of the volume of the generated microdroplets 199 is guaranteed cooperatively by the uniform discharging flow rate of the first liquid and the swing motion of the outlet end 112 of the liquid discharging nozzle 110 having the displacement changing in the sine form.

Figure 9:
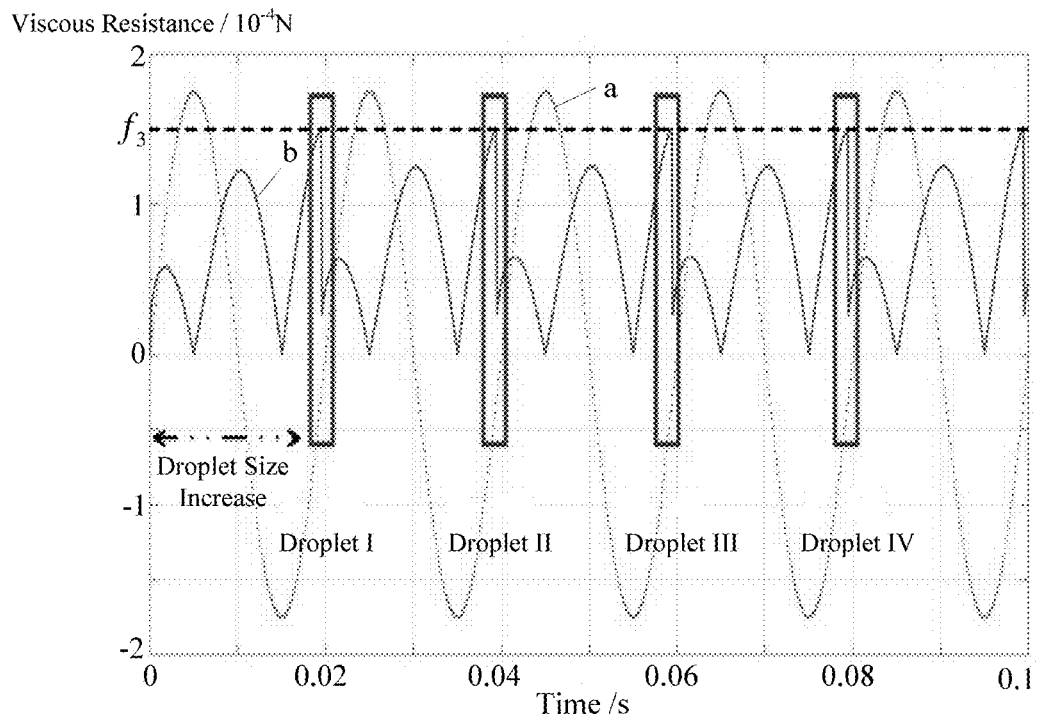
FIG. 9 is a schematic view of a process of generating one microdroplet in every one cycle of an outlet end of a liquid discharging nozzle, provided by an embodiment of the present application.

In an embodiment of the present application, referring to FIG. 9, the outlet end 112 of the liquid discharging nozzle 110 is controlled to swing along a circular arc trajectory with a displacement changing in a sine form. In a case that the liquid discharging nozzle 110 and the first liquid are not changed, the maximum adhesion force $f_3$ of the between the outlet end 112 of the liquid discharging nozzle 110 and the droplet 195 is fixed. The viscous resistance force $f_2$ applied on the droplet 195 moving in the second liquid 699 continuously increases with the increase of the radius r of the droplet 195 attached to the outlet end 112 of the liquid discharging nozzle 110. At the moment the viscous resistance force $f_2$ applied on the droplet 195 moving in the second liquid 699 is greater than the maximum adhesion force $f_3$ between the outlet end 112 of the liquid discharging nozzle 110 and the droplet 195, the droplet 195 is detached from the outlet end 112 of the liquid discharging nozzle 110 and forms the microdroplet 199. Then the next generation cycle of the microdroplet 199 begins.

In this embodiment, the maximum adhesion force $f_3$ between the outlet end 112 of the liquid discharging nozzle 110 and the droplet 195 is $f_3=1.5\times10^{-4}$ N, and the swing frequency of the outlet end 112 of the liquid discharging nozzle 110 is 50 Hz. The first microdroplet 199, the droplet I in FIG. 9, is generated at the end of the first period of the swing motion of the outlet end 112 of the liquid discharging nozzle 110 whose displacement changes in a sine form. In the initial stage of the generation of the second microdroplet 199, as the radius r of the droplet 195 attached to the outlet end 112 of the liquid discharging nozzle 110 increases fast, the viscous resistance force $f_2$ applied on the droplet 195 moving in the second liquid 699 does not immediately decrease but increases slightly, even though the moving speed of the outlet end 112 of the liquid discharging nozzle 110 decreases at this stage. After that, the radius r of the droplet 195 slowly increases, and the viscous resistance force $f_2$ applied on the droplet 195 moving in the second liquid 699 mainly changes with the moving speed of the outlet end 112 of the liquid discharging nozzle 110.

The first liquid is controlled to be discharged from the outlet end 112 of the liquid discharging nozzle 110 at the uniform flow rate, so that a new droplet 195 having the volume equal to that of the previous microdroplet 199 is generated again at the outlet end 112 of the liquid discharging nozzle 110 at the moment one motion period passed right after the generation of the previous microdroplet 199. Moreover, the moving speed of the outlet end 112 of the liquid discharging nozzle 110 at this moment is also the same as that one motion period ago. The new droplet 195, the droplet II in FIG. 9, having the same volume as that of the previous microdroplet 199 and is detached from the outlet end 112 of the liquid discharging nozzle 110. By cycling like this, the droplet III, droplet IV, and so on are generated. The uniformity of the volume of the generated microdroplets 199 is guaranteed cooperatively by the uniform discharging flow rate of the first liquid and the swing motion of the outlet end 112 of the liquid discharging nozzle 110 having the displacement changing in the sine form.

Figure 10:
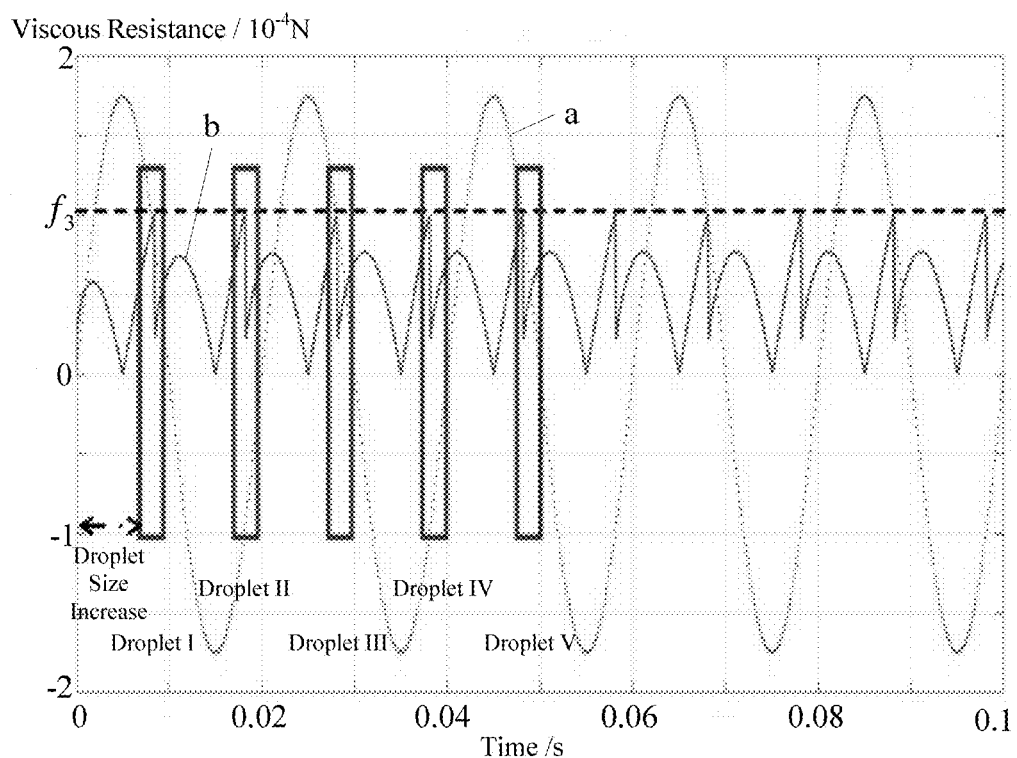
FIG. 10 is a schematic view of a process of generating two microdroplets in every one cycle of an outlet end of a liquid discharging nozzle, provided by an embodiment of the present application.
Figure 11:
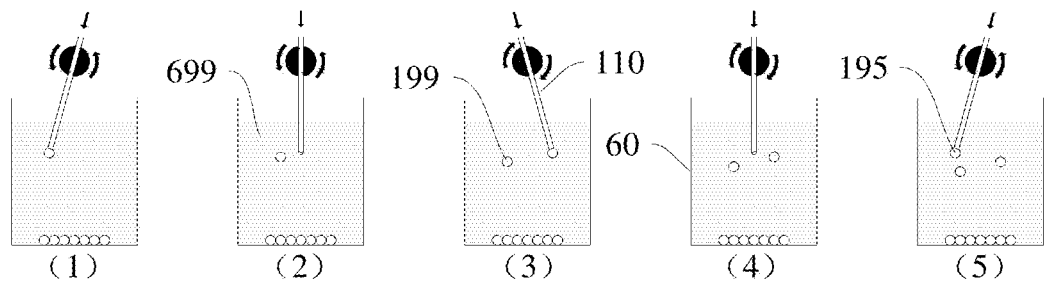
FIG. 11 is a schematic view of generating processes of microdroplets when an outlet end of a liquid discharging nozzle is swinging, provided by an embodiment of the present application.

In an embodiment of the present application, referring to FIG. 10 and FIG. 11, the outlet end 112 of the liquid discharging nozzle 110 is controlled to swing along a circular arc trajectory with a displacement changing in a sine form. In a case that the liquid discharging nozzle 110 and the first liquid are not changed, the maximum adhesion force $f_3$ between the outlet end 112 of the liquid discharging nozzle 110 and the droplet 195 is fixed. The viscous resistance force $f_2$ applied on the droplet 195 moving in the second liquid 699 continuously increases with the increase of the radius r of the droplet 195 attached to the outlet end 112 of the liquid discharging nozzle 110. At the moment the viscous resistance force $f_2$ applied on the droplet 195 moving in the second liquid 699 is greater than the maximum adhesion force $f_3$ between the outlet end 112 of the liquid discharging nozzle 110 and the droplet 195, the droplet 195 is detached from the outlet end 112 of the liquid discharging nozzle 110 and forms the microdroplet 199 (the droplet I in FIG. 10). Then the next generation cycle of the microdroplet 199 begins.

In this embodiment, the maximum adhesion force $f_3$ between the outlet end 112 of the liquid discharging nozzle 110 and the droplet 195 is $f_3=1.0\times10^{-4}$ N, and the swing frequency of the outlet end 112 of the liquid discharging nozzle 110 is 50 Hz. The first microdroplet 199 (the droplet I in FIG. 10) is generated at the accelerating stage of the first half period of the swing motion of the outlet end 112 of the liquid discharging nozzle 110 whose displacement changes in a sine form. In the initial stage of the generation of the second microdroplet 199, as the radius r of the droplet 195 attached to the outlet end 112 of the liquid discharging nozzle 110 increases fast, the viscous resistance force $f_2$ applied on the droplet 195 moving in the second liquid 699 does not immediately decrease but increases slightly, even though the moving speed of the outlet end 112 of the liquid discharging nozzle 110 decreases at this stage. After that, the radius r of the droplet 195 slowly increases, and the viscous resistance force $f_2$ applied on the droplet 195 moving in the second liquid 699 mainly changes with the moving speed of the outlet end 112 of the liquid discharging nozzle 110.

The first liquid is controlled to be discharged from the outlet end 112 of the liquid discharging nozzle 110 at the uniform flow rate. The second microdroplet 199, the droplet II in FIG. 10, is generated at the accelerating stage of the second half period of the swing motion of the outlet end 112 of the liquid discharging nozzle 110 having the displacement changing in the sine form. After that is the stable generation stage of the microdroplet 199. A new droplet 195 having the volume equal to that of the second microdroplet 199 is generated again at the outlet end 112 of the liquid discharging nozzle 110 at the moment half a motion period passed right after the generation of the second microdroplet 199. Moreover, the moving speed of the outlet end 112 of the liquid discharging nozzle 110 at this moment is also the same as that half a motion period ago. The new droplet 195 having the same volume as that of the second microdroplet 199 is detached from the outlet end 112 of the liquid discharging nozzle 110. By cycling like this, the droplet III, droplet IV, droplet V, and so on in FIG. 10 are generated. The uniformity of the volume of the generated microdroplets 199 is guaranteed cooperatively by the uniform discharging flow rate of the first liquid and the swing motion of the outlet end 112 of the liquid discharging nozzle 110 having the displacement changing in the sine form.

As described above, the condition for detaching the droplet 195 from the outlet end 112 of the liquid discharging nozzle 110 (i.e. for generating one microdroplet 199) is roughly $|\vec{f}_3|<|\vec{f}_2|$. On the condition that the first liquid is discharged at the uniform flow rate from the outlet end 112 of the liquid discharging nozzle 110, the condition for generating the uniform-sized microdroplets 199 is that: the microdroplets 199 are detached from the outlet end 112 of the liquid discharging nozzle 110 at the equal time intervals.

Figure 12:
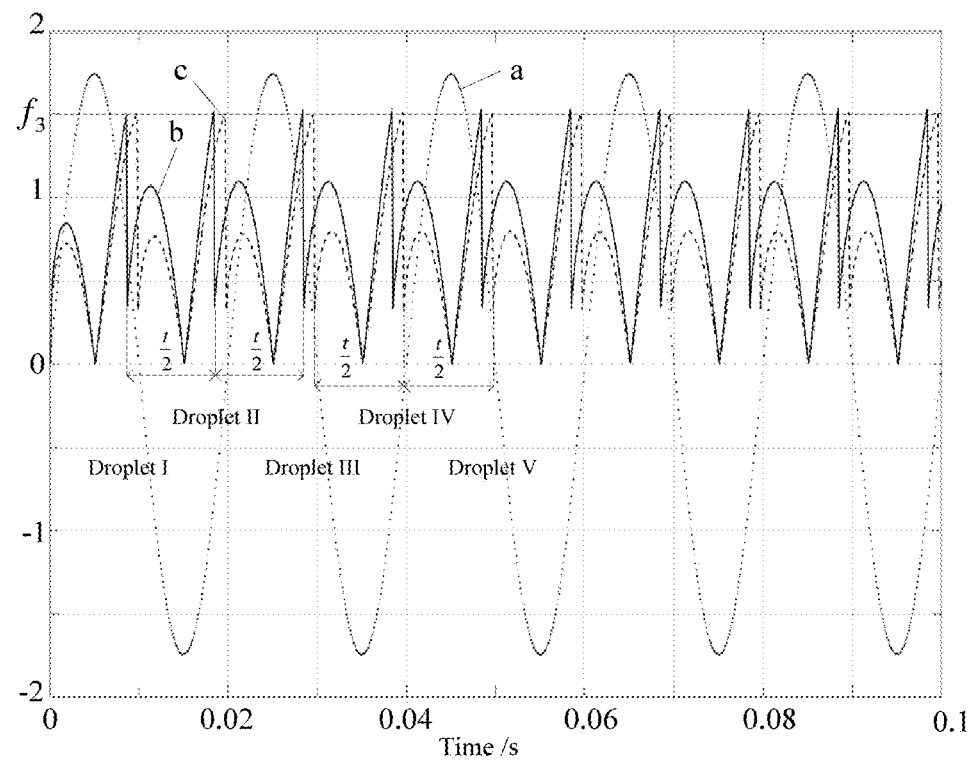
FIG. 12 is a schematic view of generating processes of microdroplets in second liquids with changed viscosities, provided by an embodiment of the present application.

The factors affecting the maximum adhesion force $f_3$ between the outlet end 112 of the liquid discharging nozzle 110 and the droplet 195 includes the surface free energy of the liquid discharging nozzle 110, the geometric dimension of the liquid discharging nozzle 110, and the surface tension of the first liquid. Therefore, the maximum the adhesion force $f_3$ between the outlet end 112 of the liquid discharging nozzle 110 and the droplet 195 is fixed in the case that the liquid discharging nozzle 110 and the first liquid are not changed. The factors affecting the viscous resistance force $f_2$ exerted upon the droplet 195 moving in the second liquid 699 includes the viscous coefficient η of the second liquid 699, the radius r of the droplet 195, and the moving speed v of the droplet 195. The radius r of the droplet 195 is decided by the time interval between the generating of the microdroplets 199. The droplet 195 moves synchronously with the outlet end 112 of the liquid discharging nozzle 110 before it is detached from the outlet end 112 of the liquid discharging nozzle 110. The moving speed of the outlet end 112 of the liquid discharging nozzle 110 can be accurately controlled by the motion controlling mechanism 130. The viscosity coefficient η of the second liquid 699 will change within a certain range during the generation of the droplet 195, but this variation range of the viscosity coefficient η of the second liquid 699 is very small. Referring to FIG. 12, the curve a represents the displacement change of the outlet end 112 of the liquid discharging nozzle 110, and the curve b and the curve c are the generation process curves of the microdroplets 199 when the viscosity coefficient q of the second liquid 699 changes within the small range. The moment, at which the microdroplet 199 is generated, is changed only within a fairy small range, and the time interval between the generating of the microdroplets 199 will not change, if the viscosity coefficient η of the second liquid 699 changes within a very small range. As shown in FIG. 12, the time intervals between the generations of the microdroplets 199 represented by the curve b and the curve c each is half a period t/2, ensuring the uniformity of the volume of the generated microdroplets 199.

Figure 13:
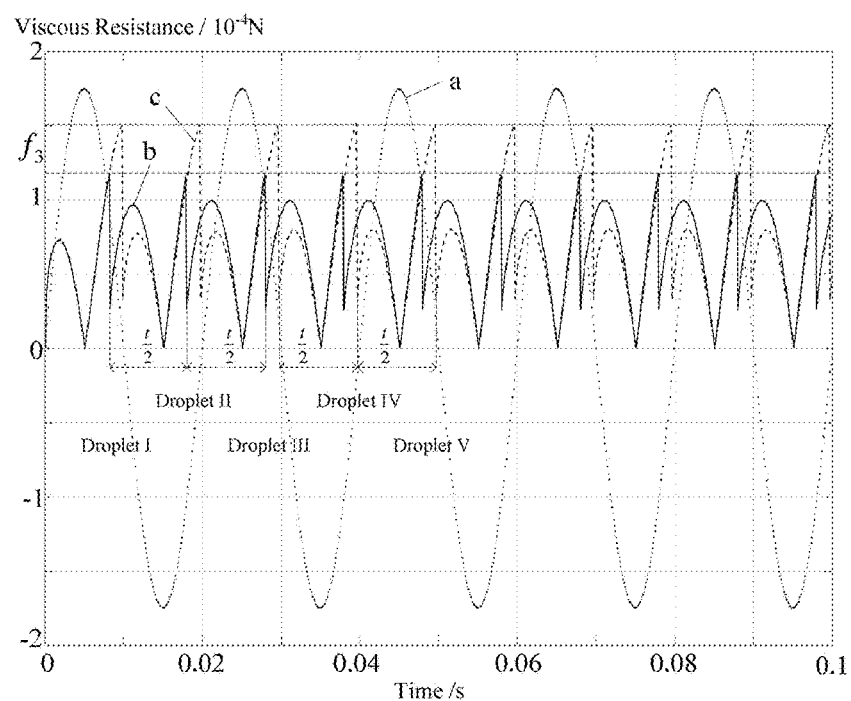
FIG. 13 is a schematic view of generating processes of microdroplets from changed liquid discharging nozzles, provided by an embodiment of the present application.

Referring to FIG. 13, on the condition that the liquid discharging nozzle 110 is replaced, or the surface tension of the first liquid changes due to change of temperature, it is difficult to accurately control the maximum adhesion force $f_3$ between the outlet end 112 of the liquid discharging nozzle 110 and the droplet 195. Therefore, the volume of the generated microdroplet 199 being not sensitive to the change of $f_3$ within a certain range is of great significance for generating the uniform-sized microdroplets 199. In FIG. 13, the curve a represents the displacement change of the outlet end 112 of the liquid discharging nozzle 110, and the curve b and the curve c are the generation process curves of the microdroplets 199 in a case that the liquid discharging nozzles 110 is replaced. By replacing the liquid discharging nozzle 110, the maximum adhesion force $f_3$ between the outlet end 112 of the liquid discharging nozzle 110 and the droplet 195 fluctuates within a certain range, which induces that the outlet ends 112 of the liquid discharging nozzles 110 have different speeds when the droplets 195 are detached. Whereas, when the generations of the microdroplets 199 enter the stable state, the speed of the outlet end 112 of the liquid discharging nozzle 110 becomes a fixed value when the droplets 195 are detached in each swing period. As shown in FIG. 13, the time intervals between the generations of the microdroplets 199 represented by the curve b and the curve c each are half a period t/2. Therefore, the fixed time interval between the generations of the microdroplets 199 can be ensured. Moreover, the flow rate of the first liquid discharged from the outlet end 112 of the liquid discharging nozzle 110 is fixed. Therefore, the generated microdroplets 199 have the uniform volume. The volume and the generation rate of the uniform-volume microdroplets 199 can be simultaneously controlled by adjusting both the flow rate of the first liquid discharging from the outlet end 112 of the liquid discharging nozzle 110 and the swing frequency of the outlet end 112 of the liquid discharging nozzle 110 in the second liquid 699.

In the above embodiment, there is a tolerance at a certain degree for the changes of the maximum adhesion force $f_3$ and the viscous resistance force $f_2$ when the outlet end 112 of the liquid discharging nozzle 110 periodically moves with a displacement changing in a sine form. That is to say, the microdroplets 199 with the uniform volume can still be generated when the maximum adhesion force $f_3$ and the viscous resistance force $f_2$ change within a certain range. When the outlet end 112 of the liquid discharging nozzle 110 periodically moves with the displacement changing in a sine form, on the condition that the uniform volume of the microdroplets 199 is guaranteed, the tolerance range for the maximum adhesion force $f_3$ is called a "platform stage". The platform stage is of great significance for the processing of the liquid discharging nozzle 110 and the controlling of the temperature of generating the microdroplets 199. The existence of the platform stage allows the requirement for the processing accuracy of the liquid discharging nozzle 110 to be reduced to a certain extent. That is to say, the microdroplets 199 with the uniform volume can still be generated even if there is a difference in the surface free energy between the liquid discharging nozzles 110 of the same batch. Similarly, the existence of the platform stage also allows the requirement for the controlling of the temperature of generating the microdroplets 199 to be reduced to a certain extent.

The cost of consumables and the cost of controlling the generation of the microdroplets 199 can be further reduced as the existence of the platform stage allows the requirement for the processing accuracy of the liquid discharging nozzle 110 or for the controlling of the temperature of generating the microdroplets 199 to be reduced to a certain extent. In the above-described embodiment, two microdroplets 199 are generated in every motion period of the outlet end 112 of the liquid discharging nozzle 110. It will be readily understood that, as long as the outlet end 112 of the liquid discharging nozzle 110 periodically moves with the displacement changing in the sine form, the platform stage and the tolerance at a certain degree for the changes of the maximum adhesion force $f_3$ and the viscous resistance force $f_2$ also exist, on the condition that one microdroplet 199 is generated in every motion period or in every two motion periods of the outlet end 112 of the liquid discharging nozzle 110.

For the reason that the microdroplet 199 is barely affected by the gravity and the inertial force, the outlet end 112 of the liquid discharging nozzle 110 can periodically move with the displacement changing in the sine form in an arbitrary direction in the second liquid 699 during the generation of the microdroplets. The moving trajectory of the outlet end 112 of the liquid discharging nozzle 110 can be an arc, a straight line, or any trajectory with another shape.

Figure 14:
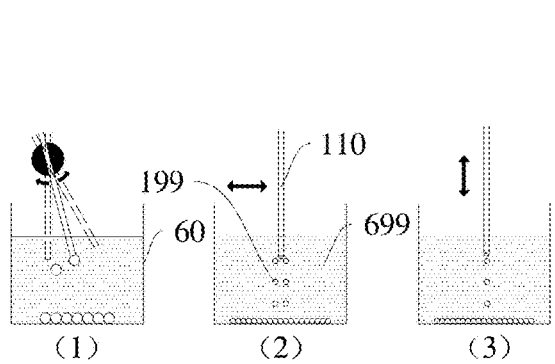
FIG. 14 is a schematic view of generating processes of microdroplets in different moving trajectories of an outlet end of a liquid discharging nozzle, provided by an embodiment of the present application.

Referring to (1) in FIG. 14, in an embodiment of the present application, the liquid discharging nozzle 110 is inclinedly inserted into the second liquid 699, and the outlet end 112 of the liquid discharging nozzle 110 swings below the liquid surface of the second liquid 699 to generate the microdroplets 199. As an implementation manner, referring to (2) in FIG. 14, the outlet end 112 of the liquid discharging nozzle 110 periodically moves along a trajectory of a horizontal straight line with a displacement changing in the sine form in the second liquid 699 to generate the microdroplets 199. As another implementation manner, referring to (3) in FIG. 14, the outlet end 112 of the liquid discharging nozzle 110 periodically moves along a trajectory of a vertical straight line with a displacement changing in the sine form in the second liquid 699 to generate the microdroplets 199.

Figure 15:
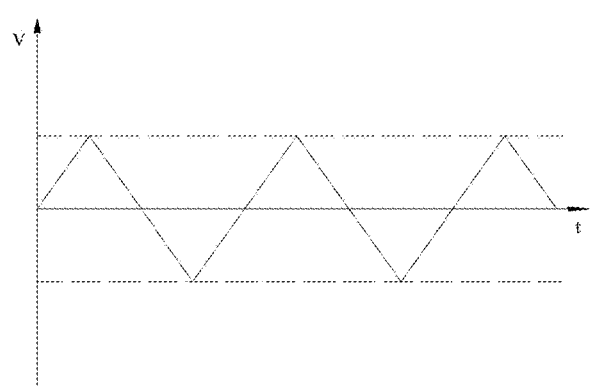
FIG. 15 is a schematic view of a velocity variation of an outlet end of a liquid discharging nozzle, provided by another embodiment of the present application.

Referring to FIG. 15, in step S213 of another embodiment of the present application, the outlet end 112 of the liquid discharging nozzle 110 moves with a uniform acceleration in both the first half period and the second half period of one speed variation period. Further, in step S213, The magnitudes of the accelerations of the outlet end 112 of the liquid discharging nozzle 110 in the first half period and the second half period are identical. The first liquid is controlled to be discharged at the uniform flow rate from the outlet end 112 of the liquid discharging nozzle 110. The viscous resistance force $f_2$ applied on the droplet 195 attached to the moving outlet end 112 of the liquid discharging nozzle 110 continuously increases with the continuous discharge of the first liquid. When the viscous resistance force $f_2$ is greater than the maximum adhesion force $f_3$ between the liquid discharging nozzle 110 and the droplet 195, the droplet 195 is detached from the liquid discharging nozzle 110 to form the microdroplet 199. Then, the generation process of the next microdroplet 199 begins. The volume uniformity of the generated microdroplets 199 is ensured by controlling the frequency and speed of motion of the outlet end 112 of the liquid discharging nozzle 110 to match with the flow rate of the first liquid.

Physical properties, such as viscosity, etc., of a conventional oil phase composition change greatly in use of the composition, so that the volume uniformity of the generated microdroplets is poor. To solve the poor-uniformity problem in the volume size of the microdroplets generated in the conventional oil phase composition used in the liquid discharging nozzle injecting/jetting method, an oil phase composition and a method for treating the oil phase composition are provided to ensure the uniformity of the volume size of the microdroplets. The present application provides an oil phase composition, namely the above-mentioned second liquid 699, for generating the microdroplets, the composition including the following components:

mineral oil, the volume percentage of the mineral oil in the oil phase composition is 88% to 98.5%; a surfactant including a silicon-oxygen chain non-ionic surfactant containing a chain alkyl group.

The oil phase composition has a density smaller than 1 g/ml, allowing most types of first liquids to be detached from the outlet end 112 of the liquid discharging nozzle 110 and form the microdroplets 199 falling in the second liquid 699. The silicon-oxygen chain non-ionic surfactant containing the chain alkyl group can prevent a fusion between the plurality of microdroplets 199.

In an embodiment of the present application, the volume percentage of the silicon-oxygen chain non-ionic surfactant containing the chain alkyl group in the oil phase composition is 1.5% to 12%. Optionally, the silicon-oxygen chain non-ionic surfactant containing the chain alkyl group includes one or both of ABIL®EM90 and ABIL®EM180. In an embodiment, the surfactant further includes a chain alkane ester. The mass-to-volume ratio of the chain alkane ester to the oil phase composition is 0.015 g/mL to 0.05 g/mL. Further, the chain alkane ester includes one or more of dipolyhydroxystearate (PEG-30), glycerol stearate, polyethylene glycol (30) dipolyhydroxystearate (Arlacel®P135), etc. Specifically, the chain alkane ester is polyethylene glycol (30) dipolyhydroxystearate (Arlacel®P135). In the present embodiment, the volume percentage of the silicon-oxygen chain non-ionic surfactant containing the chain alkyl group in the oil phase composition is 1.5% to 5.0%. In an embodiment, the silicon-oxygen chain non-ionic surfactant containing the chain alkyl group is ABIL®EM90.

Gas has a certain degree of solubility in the mineral oil, and the solubility is related to the temperatures of the gas and the mineral oil. For example, at room temperature, air dissolves but invisible in the mineral oil. The gas dissolution in the mineral oil will affect the physical properties of the mineral oil such as viscosity, bulk modulus, thermal conduction, boundary lubrication, etc., forming foam or cavitation. If the gas is saturated in the mineral oil, visible bubbles will be generated and suspended in the mineral oil, and the mineral oil will become blurry, which is called entrainment of gas. The bubbles slowly rise to the surface of the mineral oil. The gas bubbles will affect the continuity of the oil phase, thereby reducing the ability of the oil phase to prevent other phases from contacting. For example, during the PCR reaction, the temperature will be increased to 95° C., reducing the solubility of the gas in the mineral oil, so that the gas in the mineral oil will be oversaturated, and gas bubbles will be generated. The bubbles will rise to the surface of the mineral oil and eventually burst. But in this process, bubbles will affect the collection of fluorescent signals. Moreover, if the bubble in generation interacts with the microdroplet 199, it will affect the stability of the microdroplet 199 and induce the fusion between the microdroplets 199.

The present application also provides a method for treating the oil phase composition, configured for treating the oil phase composition described in any of the above embodiments. The method for treating the oil phase composition includes heating the oil phase composition while placing the oil phase composition in a negative pressure and ultrasonic vibrating environment. In the negative pressure environment, the air and other gases dissolved in the oil phase composition are separated out to minimize the amount of the air and other gases dissolved in the oil phase composition. The ultrasound can promote the separation of the gas from the oil phase composition. After the microdroplet 199 having an aqueous phase is generated, water may be dissolved in the oil phase composition in the subsequent manipulation of the microdroplet 199, which will cause a change in size of the microdroplet 199. The size change of the microdroplet 199 will affect the alignment of the microdroplets 199, which will further affect the real-time detection of the microdroplets 199. Optionally, the method for treating the oil phase composition further includes a step of making the oil phase composition saturated with water. Specifically, the step of making the oil phase composition saturated with water includes adding distilled water to the oil phase composition before heating the oil phase composition. After the heating process of the oil phase composition is completed, the oil phase composition is naturally cooled at 25° C. to 35° C. The oil phase composition is added with distilled water and heated, so that the oil phase composition is saturated with water. The insoluble water is removed at room temperature. The oil phase composition is already in a water-saturated state before the microdroplet 199 is generated, so that the amount of water entering the oil phase composition from the water-phase microdroplet 199 is minimized. Further optionally, the cooled oil phase composition is protected with nitrogen gas. Nitrogen gas has a very low solubility in the oil phase composition based on mineral oil. The use of nitrogen gas as a protective gas can prevent the air or other gases in the environment from being dissolved in the oil phase composition during storage of the oil phase composition and degrading the quality of the oil phase composition. As an implementation manner, when there is remaining space in the vessel storing the oil phase composition, the remaining space is filled with nitrogen gas.

Embodiment 1: Experimentally explore the uniformity of the volume of the microdroplets 199 generated in the oil phase compositions (the second liquid 699) having different components. The microdroplets 199 are formed in the oil phase composition (the second liquid 699) by using the method of moving the outlet end 112 of the liquid discharging nozzle 110 with the periodic instantaneous accelerated motion in the oil phase composition (the second liquid 699) to detach the first liquid in the liquid discharging nozzle 110 from the outlet end 112 of the liquid discharging nozzle 110. In the Embodiment 1, the first liquid is a water phase, and the components of the oil phase composition (the second liquid 699) are as follows:

|  | Mineral oil, v/v | ABIL ®EM90, v/v |
|---|---|---|
| Example 1 | 98.5 | 1.5 |
| Example 2 | 97.0 | 3.0 |
| Example 3 | 94.0 | 6.0 |
| Example 4 | 88.0 | 12.0 |
| Example 5 | 85.0 | 15.0 |
| Example 6 | 84.0 | 16.0 |

Figure 16:
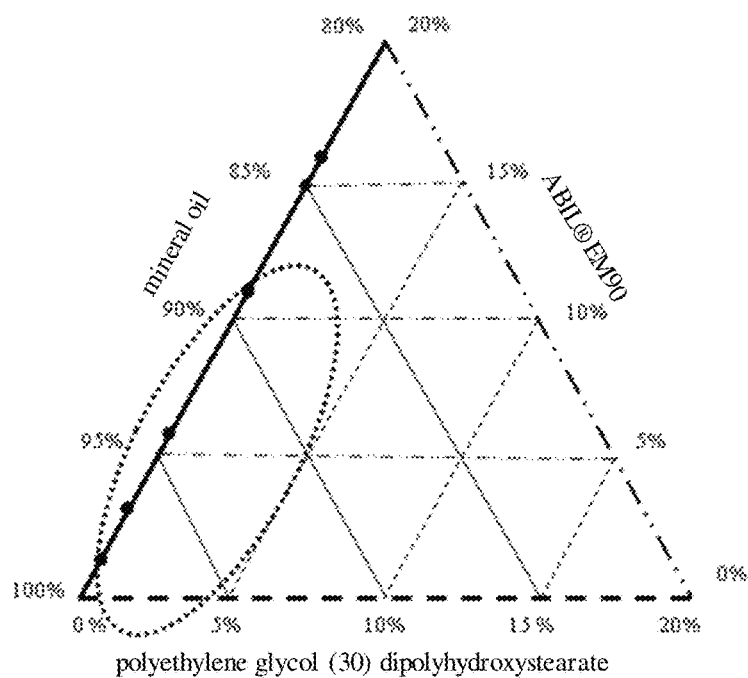
FIG. 16 is a diagram showing distributions of experimental results in Embodiment 1 provided by an embodiment of the present application.
Figure 17:
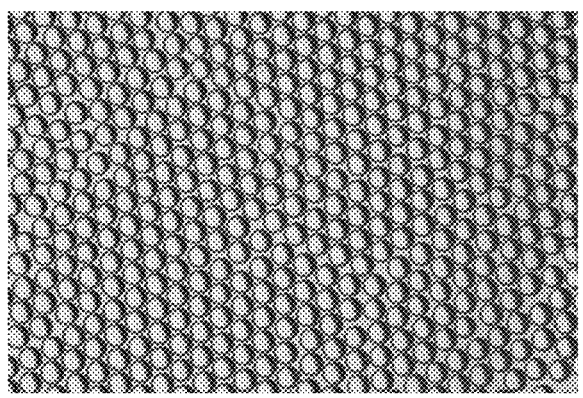
FIG. 17 is an enlarged view of microdroplets with high uniformity generated in Embodiment 1 provided by an embodiment of the present application.
Figure 18:
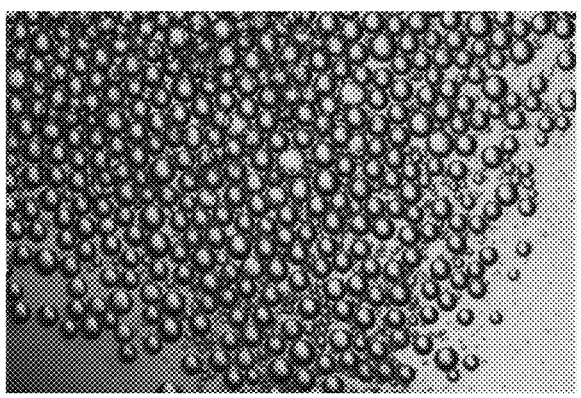
FIG. 18 is an enlarged view of microdroplets with low uniformity generated in Embodiment 1 provided by an embodiment of the present application.

As revealed in the experimental results shown in FIG. 16 and FIG. 17, the volume uniformity of the microdroplets 199 in the dotted circle of FIG. 16 is relatively good, respectively corresponding to the oil phase compositions (the second liquids 699) of Example 1, Example 2, Example 3, and Example 4. As shown in FIG. 18, when the volume percentage of ABIL®EM90 in the oil phase composition (the second liquid 699) increases to 15% and 16%, the volume uniformity of the generated microdroplets 199 is relatively poor. It is easy to conclude that the generated microdroplets 199 have better volume uniformity when the volume percentage of ABIL®EM90 in the oil phase composition (the second liquid 699) is 1.5% to 12%.

Embodiment 2: Experimentally explore the thermal stability of the microdroplets 199 generated in the oil phase compositions (the second liquid 699) having different components. The microdroplets 199 are formed by the same method as that of Examples 1 to 6. Multiple sets of oil phase compositions (the second liquid 699) containing microdroplets 199 are respectively subjected to 50 times of cycling between high and low temperatures. The cycling between high and low temperatures includes: rising the temperature to 95° C. at the speed of 6° C./s and maintaining the temperature for 10 s, then decreasing the temperature to 65° C. at the speed of 6° C./s and maintaining the temperature for 10 s. In the Embodiment 2, the components of the oil phase compositions (the second liquid 699) are as follows:

|  | Mineral oil, v/v | ABIL ®EM90, v/v | P135, m/v |
| --- | --- | --- | --- |
| Example 7 | 98.5 | 0 | 1.5 |
| Example 8 | 97 | 1.5 | 1.5 |
| Example 9 | 95.5 | 3 | 1.5 |
| Example 10 | 92.5 | 6 | 1.5 |
| Example 11 | 86.5 | 12 | 1.5 |
| Example 12 | 97 | 0 | 3 |
| Example 13 | 95.5 | 1.5 | 3 |
| Example 14 | 94 | 3 | 3 |
| Example 15 | 91 | 6 | 3 |
| Example 16 | 85 | 12 | 3 |
| Example 17 | 94 | 0 | 6 |
| Example 18 | 92.5 | 1.5 | 6 |
| Example 19 | 91 | 3 | 6 |
| Example 20 | 88 | 6 | 6 |
| Example 21 | 82 | 12 | 6 |
| Example 22 | 88 | 0 | 12 |

Figure 19:
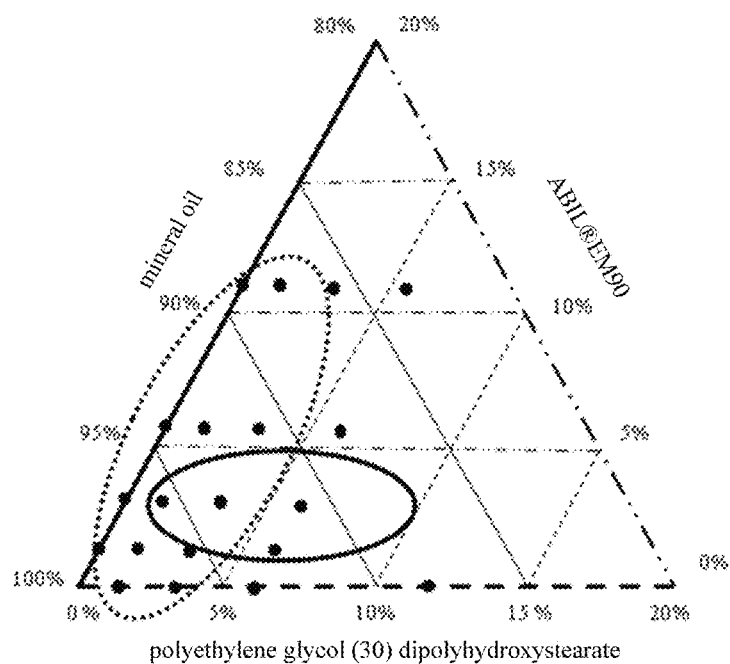
FIG. 19 is a diagram showing distributions of experimental results in Embodiment 2 provided by an embodiment of the present application.
Figure 20:
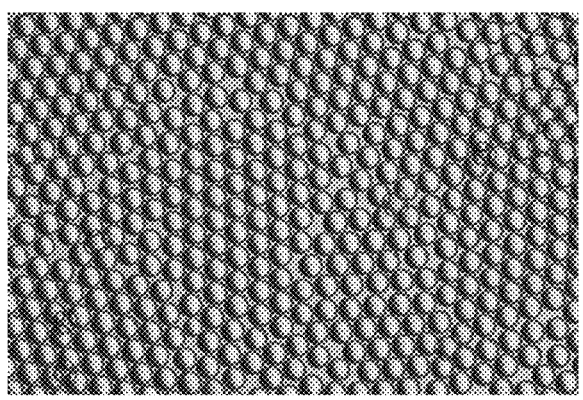
FIG. 20 is an enlarged view of microdroplets with high uniformity generated in Embodiment 2 provided by an embodiment of the present application.
Figure 21:
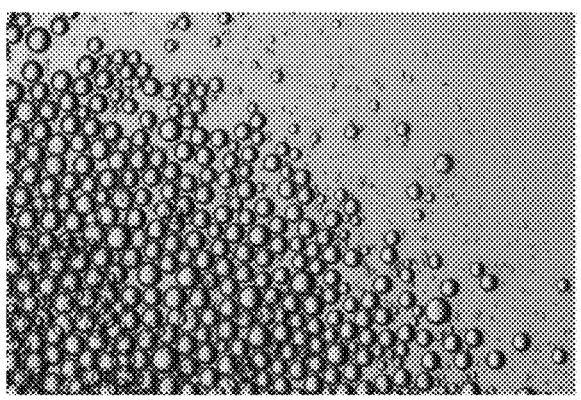
FIG. 21 is an enlarged view of microdroplets with low uniformity generated in Embodiment 2 provided by an embodiment of the present application.
Figure 22:
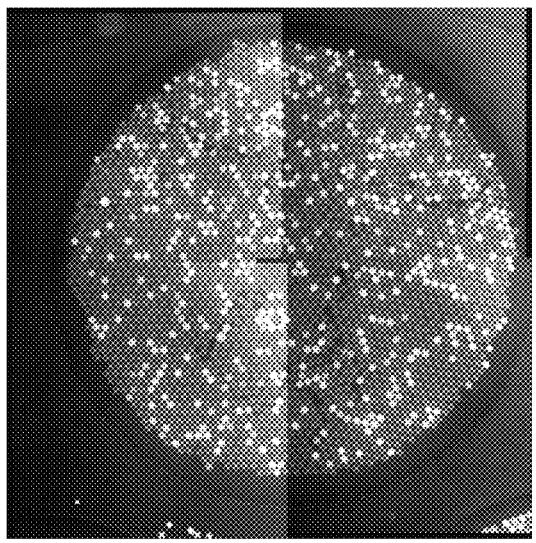
FIG. 22 is an enlarged view of microdroplets with high thermal stability generated in Embodiment 2 provided by an embodiment of the present application.
Figure 23:
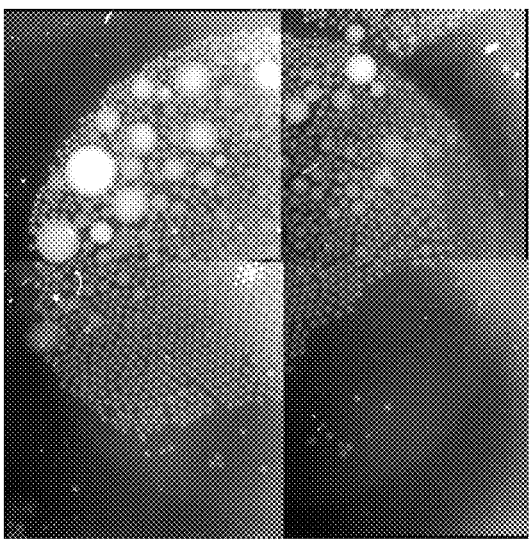
FIG. 23 is an enlarged view of microdroplets with low thermal stability generated in Embodiment 2 provided by an embodiment of the present application.

As revealed in the experimental results shown in FIG. 19 and FIG. 20, the volume uniformity of the microdroplets 199 in the dotted circle in FIG. 19 is relatively good. When the volume percentage of ABIL®EM90 in the oil phase composition (the second liquid 699) is 1.5% to 12%, and the content of P135 is less than 5%, as shown in FIG. 19 and FIG. 20, the volume uniformity of the generated microdroplets 199 is relatively good. However, the generated microdroplets 199 exhibit different volume sizes when the content of P135 is greater than 5% as shown in FIG. 19 and FIG. 21. The thermal stability of the microdroplets 199 in the solid circle in FIG. 19 is relatively good. As shown in FIG. 22, the thermal stability of the microdroplets 199 is better when the content of P135 is between 1.5% and 5.0% and the volume percentage of ABIL®EM90 is 1.5% to 5.0% in the oil phase composition (the second liquid 699). As shown in FIG. 23, when the volume percentage of ABIL®EM90 in the oil phase composition (the second liquid 699) exceeds 5.0%, the thermal stability of microdroplets 199 is relatively poor.

It can be concluded from the experimental results of 22 examples in the above two embodiments that the microdroplets 199 formed from the first liquid in the oil phase composition (the second liquid 699) have relatively good volume uniformity and thermal stability when the oil phase composition (the second liquid 699) is based on mineral oil, the volume percentage of ABIL®EM90 is 1.5% to 5.0%, and the content of P135 is 1.5% to 5.0%.

Embodiment 3: Experimentally explore a potential substitute of ABIL®EM90. ABIL®EM90 and ABIL®EM180 are both silicon-oxygen chain non-ionic surfactants containing chain alkyl groups. The experimental conditions are the same as that of the Embodiment 1, and ABIL®EM90 is completely or partially replaced by ABIL®EM180. The components of the oil phase composition (the second liquid 699) in the Embodiment 3 are as follows:

|  | Mineral oil, v/v | ABIL ®EM90, v/v | ABIL ®EM180, v/v |
| --- | --- | --- | --- |
| Example 23 | 97.0 | 0 | 3.0 |
| Example 24 | 97.0 | 1.5 | 1.5 |
| Example 25 | 94.0 | 0 | 6.0 |
| Example 26 | 94.0 | 3.0 | 3.0 |
| Example 27 | 85.0 | 0 | 15.0 |
| Example 28 | 85.0 | 7.5 | 7.5 |

Figure 24:
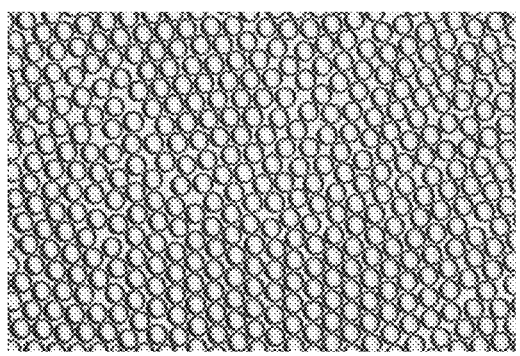
FIG. 24 is an enlarged view of microdroplets generated in Embodiment 3 provided by an embodiment of the present application.

As shown in FIG. 24, the generated microdroplets 199 have relatively good volume uniformity when the oil phase compositions (the second liquids 699) having different components in Example 23 to Example 28 in the above table are used in the generation experiments of the microdroplets 199.

Embodiment 4: Experimentally explore a potential substitute of P135. Polyethylene glycol (30) dipolyhydroxystearate (Arlacel®P135), dipolyhydroxystearate (PEG-30) and glycerol stearate are all chain alkane esters. The experimental conditions are the same as that of the Embodiment 2, and P135 is completely or partially replaced by dipolyhydroxystearate (PEG-30) and glycerol stearate. The components of the oil phase composition (the second liquid 699) in the Embodiment 4 are as follows:

|  | Mineral oil, v/v | ABIL ®EM90, v/v | ABIL ®EM180, v/v | P135, m/v | PEG-30, v/v | Glycerol stearate, v/v |
| --- | --- | --- | --- | --- | --- | --- |
| Example 29 | 94.0 | 1.5 | 1.5 | 0 | 3.0 | 0 |
| Example 30 | 94.0 | 1.5 | 1.5 | 0 | 0 | 3.0 |
| Example 31 | 94.0 | 1.5 | 1.5 | 0 | 1.5 | 1.5 |
| Example 32 | 94.0 | 1.5 | 1.5 | 1.0 | 1.0 | 1.0 |

Figure 25:
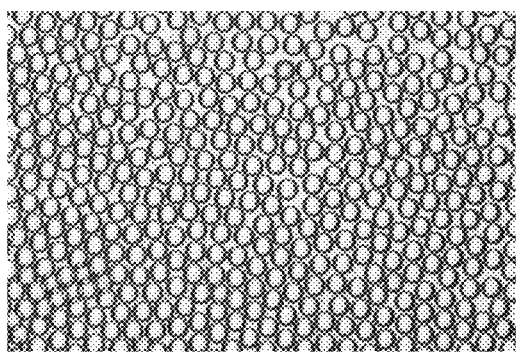
FIG. 25 is an enlarged view of microdroplets with high uniformity generated in Embodiment 4 provided by an embodiment of the present application.
Figure 26:
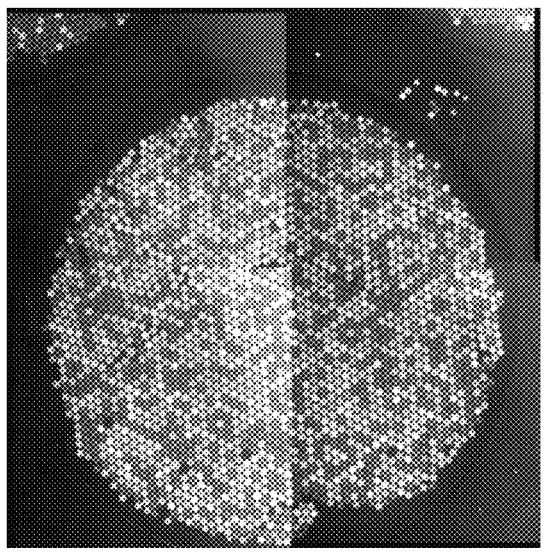
FIG. 26 is an enlarged view of microdroplets with high thermal stability generated in Embodiment 4 provided by an embodiment of the present application.

As shown in FIG. 25 and FIG. 26, the generated microdroplets 199 have relatively good volume uniformity and thermal stability when the oil phase compositions (the second liquids 699) having different components in Example 29 to Example 32 in the above table are used in the generation experiments and thermal stability experiments of the microdroplets 199.

In a specific application environment, the generating device and the generating method of the microdroplet 199 provided in the present application are applied in the polymerase chain reaction (PCR).

In an embodiment, the microdroplet 199 is a nucleic acid amplification reaction liquid to be detected. The microdroplet generating device 10 microdropletizes the nucleic acid amplification reaction liquid to be detected into a plurality of microdroplets so as to be detected via the digital PCR detection apparatus 1. By transforming the nucleic acid amplification reaction liquid to be detected into the plurality of microdroplets 199 via the microdroplet generating device 10 of the integrated digital PCR detection apparatus 1, detecting fragments in the sample to be detected can be separated from plentiful complex backgrounds and placed into the microdroplet container 60 for the detection. A plurality of microdroplets 199 with a uniform size can be generated via the microdroplet generating device 10. Each microdroplet 199 has a size at a micrometer scale and can be regarded as an independent reactor functioning as a test tube commonly used in a biochemical reaction. It is convenient to observe and detect the plurality of microdroplets 199 placed in the microdroplet container 60. Moreover, a plurality of microdroplets 199 having different volumes can also be generated via the microdroplet generating device 10 to be subjected to a medical and clinical test. The plurality of microdroplets are small in volume and large in quantity, thereby possessing many advantages over the conventional test tubes. A large number of microdroplets 199 can be generated via the microdroplet generating device 10, so that the digital PCR detection apparatus 1 has advantages of high throughput, low cost of consumable materials, and low background noise, thereby having a broad industrialization prospect.

Conventional temperature controlling device has low temperature increasing and decreasing rates. It needs tens of seconds to several minutes to complete each temperature increasing or decreasing. The time period for tens of cycles of PCR cycling is about 1 to 2 hours, so that the time period for completing a nucleic acid amplification is prolonged, and the efficiency of nucleic acid amplification is low. Moreover, the conventional temperature controlling device has a short service life. To address the problems of low temperature increasing and decreasing rates in the conventional temperature controlling device, a temperature controlling device having high temperature increasing and decreasing rates and a long service life is provided.

Figure 27:
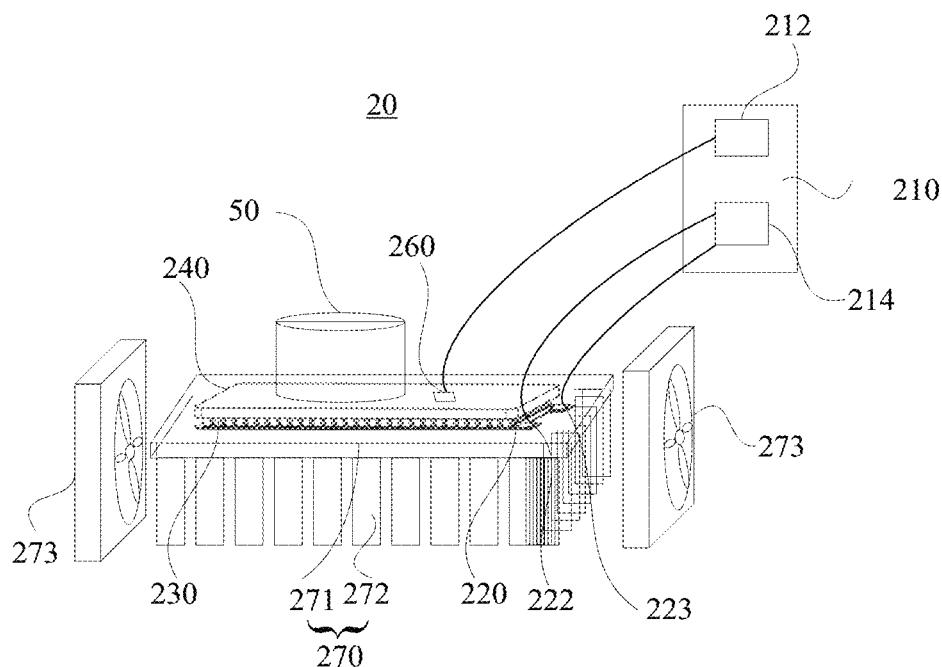
FIG. 27 is a schematic structural view of a temperature controlling device of the present application.
Figure 28:
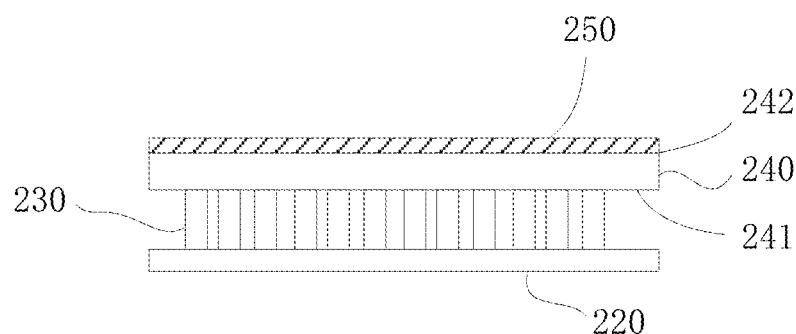
FIG. 28 is a schematic cross-sectional structural view of a temperature controlling device of the present application.

Referring to FIGS. 27 and 28, a temperature controlling device 20 is provided in the present application. The temperature controlling device 20 includes a flexible circuit board 220, a heating substrate 240 spaced from the flexible circuit board 220, and a plurality of semiconductor electric couples 230. The heating substrate 240 includes a first surface 241 and a second surface 242 opposite to each other. The plurality of semiconductor electric couples 230 are disposed between the flexible circuit board 220 and the first surface 241. The plurality of semiconductor electric couples 230 are connected to each other in series, in parallel, or in combination of the series and parallel connections.

The temperature controlling device 20 is generally used in a high-low temperature cycling environment whose temperature needs to be increased and decreased rapidly and thus having a high standard requirement to the temperature controlling device 20. The flexible circuit board 220 is used in the temperature controlling device 20 to meet the application requirement of the temperature controlling device 20. The flexible circuit board 220 has characteristics of high wiring density, light weight, small thickness, and good flexibility. The flexible circuit board 220 counteracts the thermal stress with its own deformation during the heating and cooling processes. Since the thermal stress generated in the heating and cooling processes can be reduced by the flexible circuit board 220, the service life of the temperature controlling device 20 is prolonged. Moreover, the problem of non-uniform temperature distribution is solved by using the flexible circuit board 220. When the nucleic acids in the plurality of microdroplets are amplified in different temperature ranges, the temperature ranges can be rapidly switched within a few seconds via the flexible circuit board 220, the heating substrate 240, and the plurality of semiconductor electric couples 230. The temperature can be increased and decreased instantaneously via the temperature controlling device 20, thereby accelerating the temperature increasing and decreasing processes to achieve a high-low temperature cycling, reducing the detection time of the digital PCR detection apparatus 1, and increasing the detection efficiency.

The flexible circuit board 220 (namely the flexible printed circuit, FPC) can be a flexible printed circuit board with high reliability and excellent performance, having a polyimide film or a polyester film as a substrate. The flexible circuit board has characteristics of high wiring density, light weight, small thickness, and good flexibility. Since the flexible circuit board is light in weight and thin in thickness, the product size can be effectively decreased. The semiconductor cooler (namely the thermoelectric cooler, TEC) is based on the Peltier effect of a semiconductor. The Peltier effect refers to a phenomenon that, when a direct current flows through an electric couple composed by two semiconductor materials, one end of the couple absorbs heat and the other end of the couple releases heat. By replacing one substrate of the conventional semiconductor cooler with the flexible circuit board 220, the semiconductor cooler can have a relatively good thermal conductivity. An object generates a stress in response to a temperature change if the object cannot expand or contract completely or freely due to external constraints and constraints between internal portions. The stress caused by the temperature change is the thermal stress. The thermal stress equilibrates with zero external load and is the self-equilibrium stress caused by the constraint on the thermal deformation. The compression occurs at the higher temperature, and the tension occurs at the lower temperature. A mechanical property and a service life of a component can be improved by reasonably distributing the stress under certain conditions, thereby turning the harm into a benefit.

In an embodiment, the heating substrate 240 can be a superconducting aluminum substrate circuit.

The aluminum substrate is a metal-based copper clad laminate. Generally, a single sided board is formed by three layers, which are a circuit layer (copper foil), an insulating layer, and a metal substrate layer. The superconducting aluminum substrate circuit has a circuit board made of aluminum alloy and capable of conducting heat rapidly. The aluminum substrate can minimize the thermal resistance, thereby having an excellent thermal conductivity. In addition, the aluminum substrate has an excellent mechanical property as compared to a thick film ceramic circuit.

Figure 29:
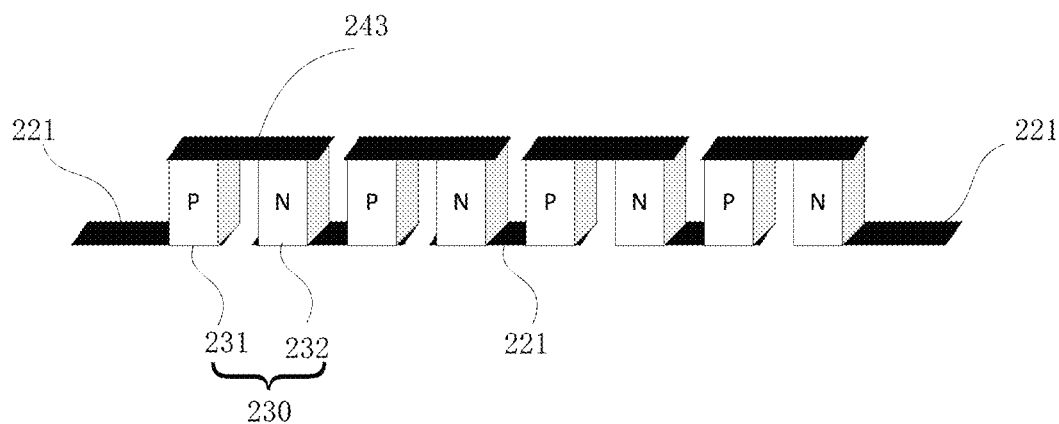
FIG. 29 is a schematic structural view of a connection between semiconductor electric couples and electrodes of the present application.

As shown in FIG. 29, in an embodiment, the semiconductor electric couple 230 includes a P-type couple component 231 and a N-type couple component 232 spaced from the P-type couple component 231.

The P-type couple component 231 and N-type couple component 232 are welded between the flexible circuit board 220 and the substrate 240. The semiconductor electric couple 230 includes a pair of couple components which are the P-type couple component 231 and the N-type couple component 232. The plurality of semiconductor electric couples 230 are connected to each other via electrodes, and are sandwiched between the flexible circuit board 220 and the first surface 241, forming a "hot" side and a "cold" side when a current flows therethrough. Cooling or heating, and the cooling (or heating) rate are determined by a direction and a magnitude of the current flowing through the semiconductor electric couples 230. Considering that the thermoelectric effect produced by one semiconductor electric couple 230 is weak, hundreds of semiconductor electric couples 230 are connected in series in practical application to enhance the produced thermoelectric effect.

In an embodiment, the first surface 241 is provided with a plurality of first electrode plates 243 spaced from each other. One first electrode plate 243 corresponds to one semiconductor electric couple 230. The P-type couple component 231 and the N-type couple component 232 of the semiconductor electric couple 230 are connected in series via the first electrode plate 243.

In an embodiment, the flexible circuit board 220 includes a plurality of second electrode plates 221 spaced from each other and connected in series. Two adjacent semiconductor electric couples 230 are connected in series via one second electrode plate 221.

When a current is flowing through the semiconductor electric couple 230 composed of the P-type couple component 231 and the N-type couple component 232, the heat is transported from one end to the other end to produce a heat transport between the two ends, thereby obtaining a temperature difference and forming a hot end and a cold end. However, the P-type couple component 231 and the N-type couple component 232 have their own electrical resistances. When the electric current flows therethrough, the P-type couple component 231 and the N-type couple component 232 generate heat, which affects the heat transport. In addition, the heat can be further reversely transported between the flexible circuit board 220 and the heating substrate 240 via air and the P-type couple component 231 and the N-type couple component 232 themselves. When a certain temperature difference is reached between the hot end and the cold end, and these two types of heat transports are equivalent in amount, an equilibrium is achieved, and the forward heat transport and the reverse heat transport are offset with each other. In this case, the temperatures of the hot end and cold end will not further change. To further decrease the temperature of the cold end, the temperature of the hot end can be further decreased by methods such as heat dissipation.

In an embodiment, the temperature controlling device 20 further includes a thermal conduction enhancing layer 250 disposed on the second surface 242.

The thermal conduction enhancing layer 250 has excellent strength, flexibility, electrical conductivity, thermal conductivity, and optical property. The thermal conduction enhancing layer 250 can directly contact the microdroplet container 60 to uniformly heat the plurality of microdroplets, so that the nucleic acid amplification can be achieved by controlling the temperature. The thermal conduction enhancing layer 250 can be a graphite thermal conducting layer or a silicone grease thermal conducting layer, which facilitates the thermal conduction and improves the temperature uniformity of the second surface 242 of the heating substrate 24, thereby ensuring the temperature uniformity of the surface in proximity to the microdroplet container 60. The plurality of microdroplets are thereby heated uniformly to have the nucleic acid amplification, so that the detection efficiency is increased and time is saved.

In an embodiment, a material of the thermal conduction enhancing layer 250 includes graphene. Graphene is a planar film, has an excellent thermal conductivity, and can uniformly conduct heat in the transverse direction. In an embodiment, the temperature controlling device 20 further includes a second controller 210 electrically connected to the flexible circuit board 220 to control a magnitude of the electric current.

In an embodiment, the temperature controlling device 20 further includes a temperature sensor 260 disposed on the second surface 242 and electrically connected to the second controller 210 to detect the temperature of the second surface 242 and transmit the temperature to the second controller 210. The temperature sensor 260 is disposed on the second surface 242 of the thermal conduction enhancing layer 250 to detect the temperature of the second surface 242 in real time and feed the temperature information to the second controller 210, so that the control of the heating temperature of the plurality of microdroplets can be achieved. The temperature sensor 260 is configured to measure the temperature of the microdroplet container 60 by detecting a variation of an electrical resistance of a metal, so as to monitor the temperature variation of the plurality of microdroplets during the nucleic acid amplification in real time, and to feed the temperature information to the second controller 210. A controlling circuit is thereby controlled to regulate the temperature. The nucleic acid amplification can be well performed due to the temperature control.

In an embodiment, the second controller 210 includes a temperature controlling unit 212 and a controlling circuit 214. The temperature controlling unit 212 is connected to the temperature sensor 260 to detect the temperature of the second surface 242 in real time. The controlling circuit 214 is connected to the flexible circuit board 220 to regulate the temperature variation of the semiconductor electric couples 230. The temperature controlling unit 212 and the controlling circuit 214 are arranged on the same circuit board. The temperature controlling unit 212 is connected with the controlling circuit 214 in a manner to perform a logical operation under an internal algorithm. A Packet Identifier closed-loop control algorithm, i.e., a PID closed-loop control algorithm can be used. The temperature detected by the temperature controlling unit 212, as a temperature feedback from the nucleic acid amplification, is an input to the internal algorithm. The calculated result from the controlling circuit 214 is an output of the internal algorithm. Thus, a closed-loop is formed. The temperature feedback is a temperature value transformed from the electrical signal collected from a platinum resistor by a sampling circuit. The temperature value is transmitted to an input port of the controlling circuit. The temperature sensor 260 is connected to the temperature controlling unit 212 via a standard platinum resistor three-wire system.

In an embodiment, the flexible circuit board 220 is provided with a first electrode 222 and a second electrode 223. The plurality of second electrode plates 221 connected in series are further connected to the first electrode 222 and the second electrode 223 in series. The first electrode 222 and the second electrode 223 are respectively connected to the controlling circuit. The controlling circuit 214 is connected to the flexible circuit board 220 via two wires respectively connected to the first electrode 222 and the second electrode 223.

In an embodiment, the temperature controlling device 20 further includes a heat dissipating device 270 including a substrate 271 and heat dissipating sheets 272 connected to the substrate 271. The flexible circuit board 220 is disposed on a surface of the substrate 271. The heat dissipating sheets 272 disposed on a surface of the substrate 271 increase the heat-exchange area without decreasing the area of the substrate 271, increase a time period for a cold wind applied on the surface of the substrate 271, and form multiple heat dissipating channels which further facilitate the heat exchange, thereby carrying more heat from the surface of the substrate 271 and thus achieving a better heat dissipating effect.

In an embodiment, the temperature controlling device 20 further includes a fan 273 disposed around the heat dissipating sheets 272. The fan 273 can assist the heat dissipating device 270 to dissipate heat. A number of fans 273 can be disposed around the heat dissipating sheets 272 to achieve a better heat dissipating effect and allow the temperature controlling device 20 to increase or decrease the temperature more rapidly.

In an embodiment, an alternating electric current is conducted to the temperature controlling device 20, and the magnitude of the current is regulated by the second controller 210. The second controller 210 controls the temperature controlling device 20 to perform the cooling function or the heating function, and controls the cooling and heating rates. At the same time, the heating temperature of the microdroplet container is detected in real time by the temperature sensor 260. The temperature information is fed back to the temperature controlling unit 212. The temperature controlling unit 212 feeds the temperature variation information back to the controlling circuit 214 to control the temperature of the plurality of microdroplets. The nucleic acid amplification can be performed on the plurality of microdroplets via the temperature controlling device 20. Three temperature points of the denaturation, annealing, and extension are set on the basis of the PCR principle. The three-temperature-point method is used in a standard reaction process. More specifically, double-stranded DNAs are denatured at 90° C. to 95° C.; and then the temperature is rapidly decreased to 40° C. to 60° C., at which primers are annealed and bound to target sequences; and then the temperature is rapidly increased to 70° C. to 75° C., at which primer strands extend along templates under the action of Taq DNA polymerase. The nucleic acid amplification can be performed in an appropriate temperature range. While the nucleic acids are amplified, a bottom plate of the microdroplet container 60 closely contacts the temperature controlling device 20 with no gap therebetween to increase the accuracy of the digital PCR detection apparatus 1.

When the nucleic acid amplification of the plurality of microdroplets are performed at different temperature ranges, the temperature ranges can be rapidly switched within a few seconds. The temperature can be increased and decreased instantaneously via the temperature controlling device 20, thereby shortening the temperature increasing and decreasing processes to achieve the high-low temperature cycling, reducing the detection time of the digital PCR detection apparatus 1, and increasing the detection efficiency.

In an embodiment, the amplifying the nucleic acids through the temperature controlling device 20 includes:

firstly, placing the microdroplet container 60 on the thermal conduction enhancing layer 250 of the temperature controlling device 20;

secondly, increasing the temperature of the plurality of microdroplets to 95° C. by heating and then keep heating for 10 min, wherein the heating the plurality of microdroplets to 95° C. and then keep heating for 10 min is to thermally activate enzymes in the plurality of microdroplets;

thirdly, denaturing the plurality of microdroplets for 30 s after the thermal activation of the enzymes in the plurality of microdroplets;

fourthly, decreasing the temperature of the plurality of microdroplets to 55° C. after the denaturation, and annealing and extending for 45 s; the above steps are cycled for 45 times;

finally, after the 45 cycles, the temperature is decreased to 4° C. to store the plurality of microdroplets for a long time.

Figure 30:
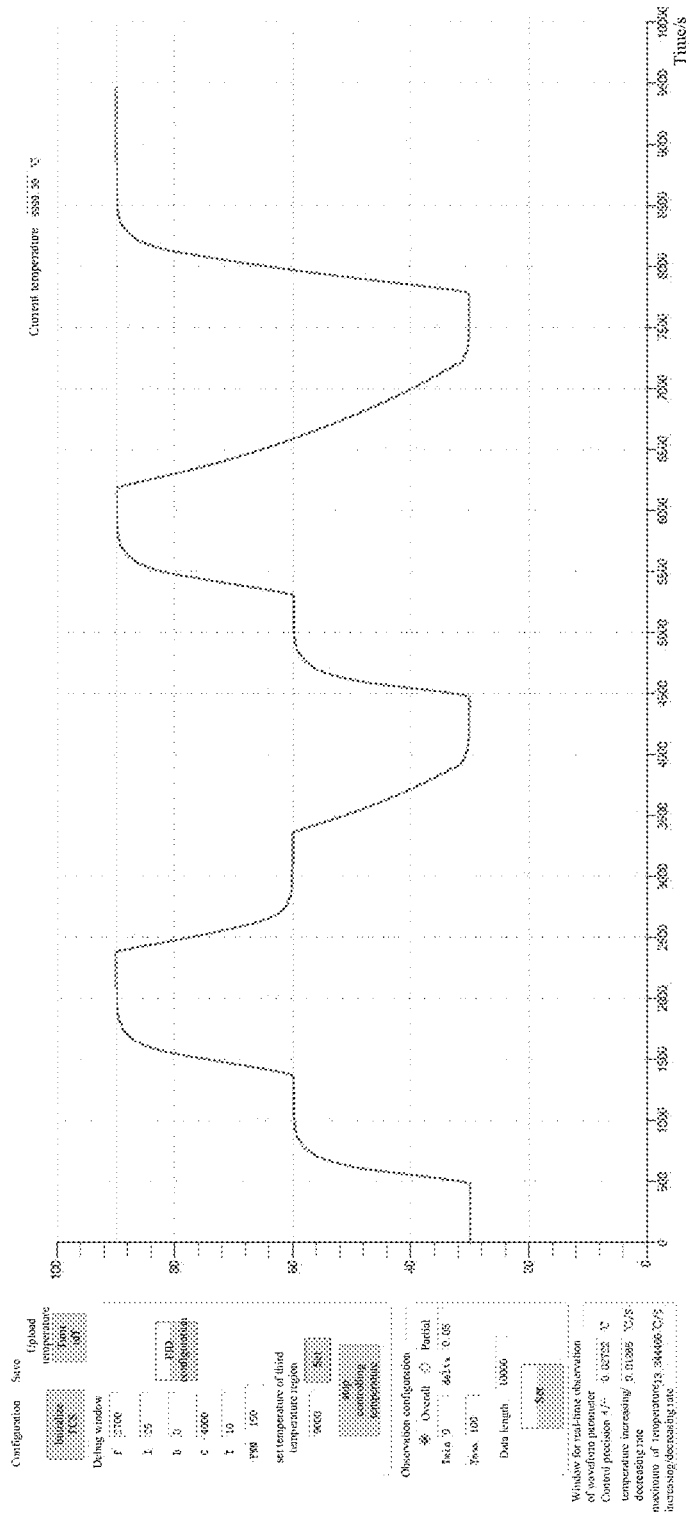
FIG. 30 is a graph showing an instantaneous state performance of a temperature controlling device of the present application.

Referring to FIG. 30, generally, there are two main indexes for testing the temperature controlling performance of the temperature controlling device 20. The temperature increasing and decreasing situations of the temperature controlling device 20 in an instantaneous state and in a stable state are observed. By monitoring the heating process of the plurality of microdroplets, it is found that when increasing or decreasing the temperature of the plurality of microdroplets via the temperature controlling device 20, a maximum temperature increasing or decreasing rate can reach 13.34448° C./s, and the control accuracy is 0.02722° C. Moreover, sometimes the fastest rate for increasing the temperature to the stable state by the temperature controlling device 20 can reach 18.953894° C./s. Therefore, the temperature controlling device 20 has a good instantaneous response, and the instantaneous increase and instantaneous decrease of the temperature can be achieved via the temperature controlling device 20, so as to save the time and increase the detection efficiency.

Figure 31:
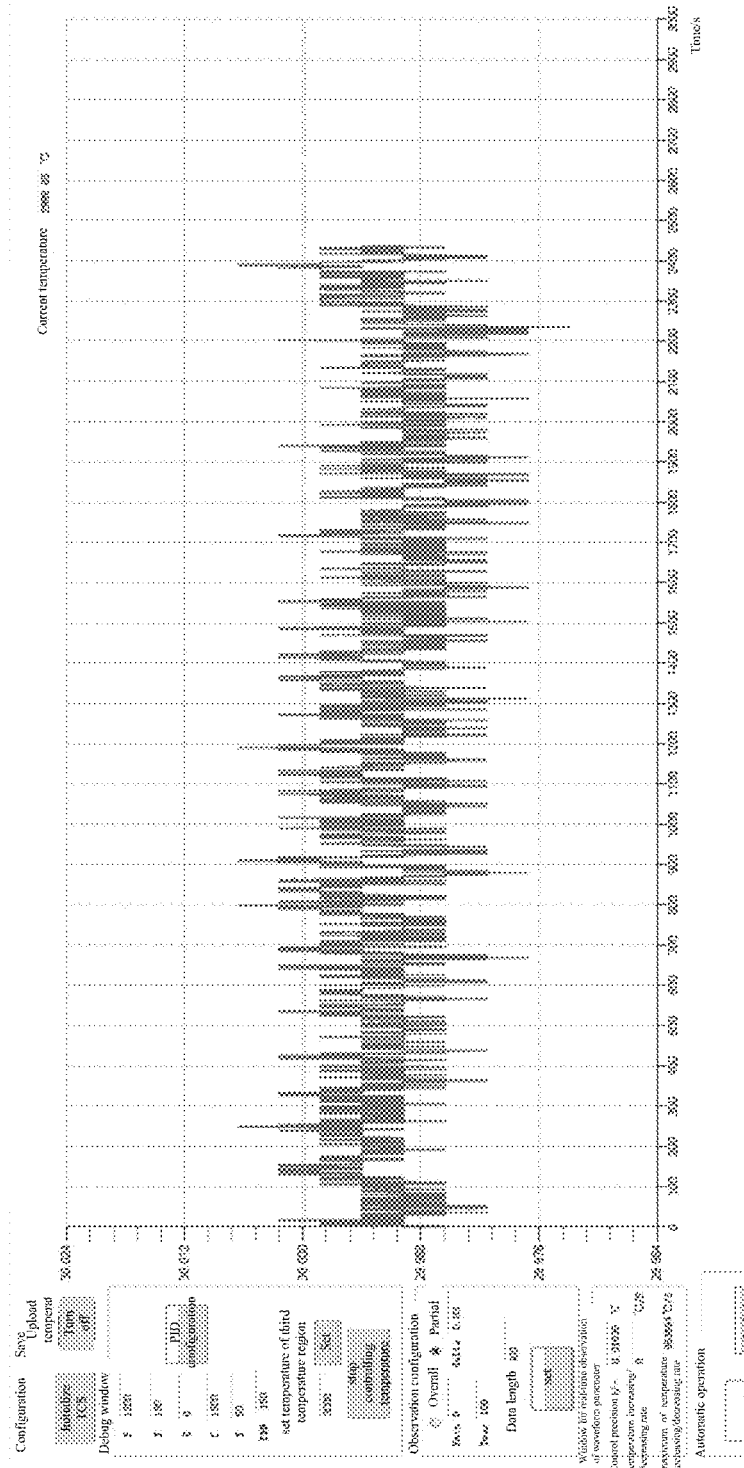
FIG. 31 is a graph showing a steady state performance of a temperature controlling device of the present application.
Figure 32:
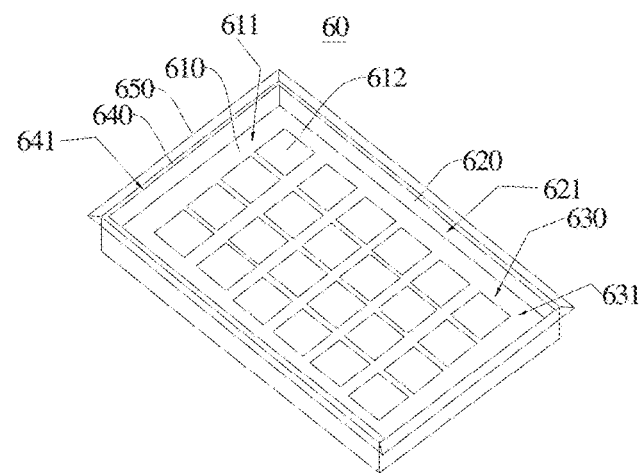
FIG. 32 is a schematic structural view of a microdroplet container of the present application.
Figures 33, 34:
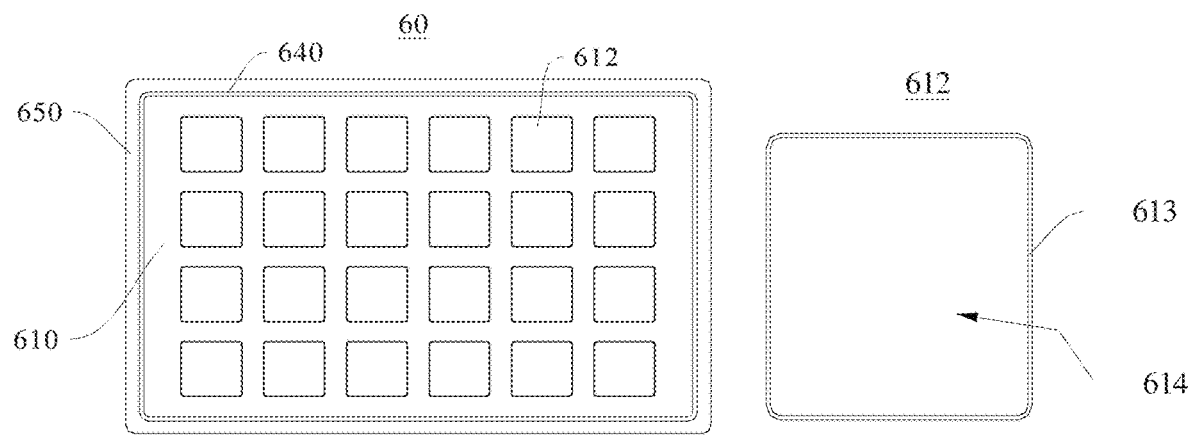
FIG. 33 is a schematic structural top view of a microdroplet container of the present application.
FIG. 34 is a schematic structural view of a reacting unit of a microdroplet container of the present application.
Figure 35:
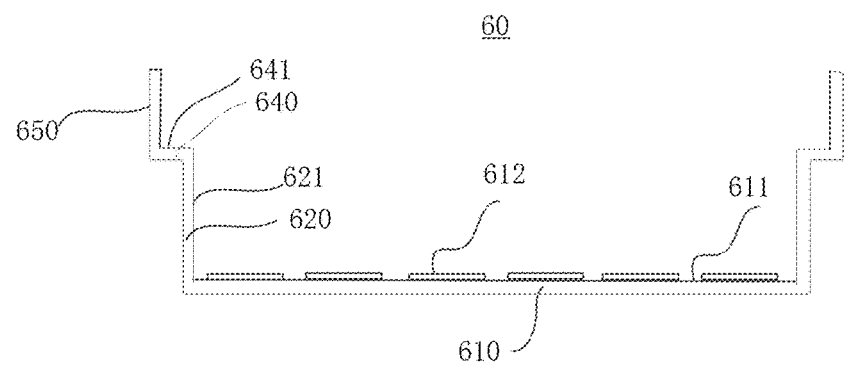
FIG. 35 is a schematic structural cross-sectional view of a microdroplet container of the present application.
Figure 36:
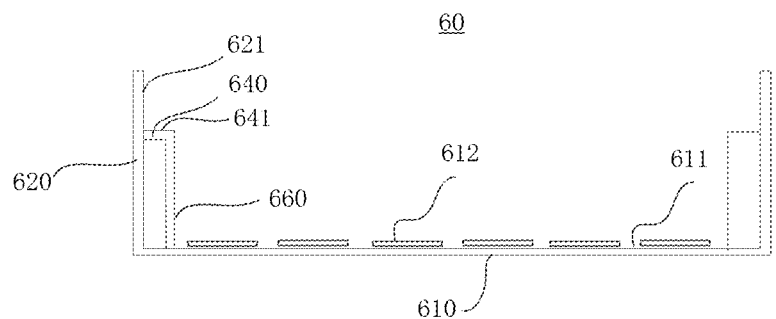
FIG. 36 is a schematic structural cross-sectional view of a microdroplet container of the present application.
Figure 37:
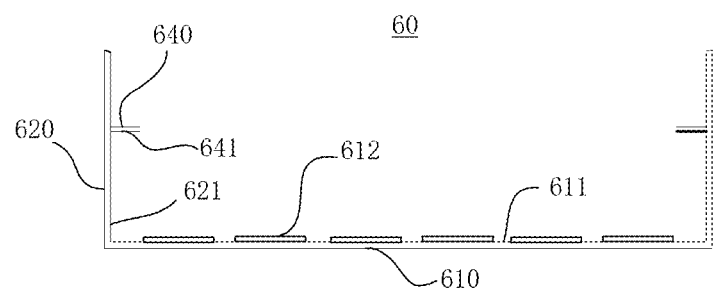
FIG. 37 is a schematic structural cross-sectional view of a microdroplet container of the present application.

Referring to FIG. 31, when the temperature controlling device 20 is in the stable state, the temperature has a fluctuation after it reaches the stable state. When the temperature controlling device 20 is in the stable state, the temperature variation is relatively stable and the temperature fluctuation is relatively small. Therefore, not only a temperature increase-decrease cycling can be rapidly achieved by the temperature controlling device 20, but also the temperature can fluctuate in a relatively small range in the stable state, so that the time of the digital PCR detection of the solution sample is saved and the working efficiency is increased. Such temperature increasing and decreasing rates reduce the time for completing the nucleic acid amplification, increase the efficiency of the nucleic acid amplification, and increase the accuracy of the digital PCR detection system.

The microdroplet generating device 10 microdropletizes the nucleic acid amplification reaction liquid to be detected into the plurality of microdroplets. Then, the plurality of microdroplets are heated by the temperature controlling device 20, during which the images showing variations in fluorescence of the plurality of microdroplets are photographically detected in real time by the fluorescence signal detecting device 30. The Ct values of the plurality of microdroplets are obtained by analyzing the images showing variations in fluorescence of the plurality of microdroplets by using the quantitative analysis device 40. An initial concentration of nucleic acids is analyzed quantitatively according to the relationship between the Ct value and the initial copy number.

The microdroplet generating device 10 forms the nucleic acid amplification reaction liquid to be detected into the plurality of microdroplets. Then, the temperature controlling device 20 amplifies the nucleic acids in the plurality of microdroplets, while the fluorescence signal detecting device 30 takes images showing variations in fluorescence of the plurality of microdroplets in real time. Fluorescence variation curves of the plurality of microdroplets are obtained from the images showing variations in fluorescence of the plurality of microdroplets. Ct values of the plurality of microdroplets can be obtained according to the fluorescence variation curves. In addition, a quantitative analysis can be performed to obtain an initial concentration of DNA according to the relationship between the Ct value and the initial copy number. The Ct value refers to the number of the temperature cycles that each microdroplet has undergone when its fluorescence signal reaches a preset threshold.

The microdroplets having a uniform size are generated by the microdroplet generating device 10. The nucleic acid amplification reactions for the plurality of microdroplets are carried out in the temperature controlling device 20; and the signals, such as the fluorescence signals, ultraviolet absorption signals, turbidity signals, and so on, of reaction products are collected by the fluorescence signal detecting device 30. The number of microdroplets in which amplifications of target sequences are achieved is analyzed by comparing a composition difference between the amplified and non-amplified microdroplets, so that the quantitative analysis of the nucleic acid molecules can be finally achieved. The detection result, obtained by observing the images showing variations in fluorescence of the plurality of microdroplets in real time, is direct, so that the problems of false positive results and false negative results in the plurality of microdroplets can be solved.

In an embodiment, the fluorescence signal detecting device 30 includes an exciting light source, a fluorescence detecting assembly, and a third controller. The exciting light source is disposed above a detection area of the microdroplet container 60, and irradiates the detection area of the microdroplet container 60 with an oblique angle to form an oblique light path. The fluorescence detecting assembly is disposed right above the detection area of the microdroplet container 60 to acquire a fluorescence image of the plurality of microdroplets. The third controller is respectively connected to the exciting light source and the fluorescence detecting assembly to control the exciting light source and the fluorescence detecting assembly. The fluorescence signal detecting device can perform a multiple-fluorescence-channel imaging and a bright field and dark field imaging for the microdroplets. The multiple-fluorescence-channel imaging is configured to detect the reaction signals of the microdroplets, and the bright field and dark field imaging is configured to detect the dimensional information of the generated microdroplets and to monitor the status of the microdroplets during the reaction.

The generation of the fluorescence image of the plurality of microdroplets is mainly completed in the camera of the fluorescence signal detecting device. The fluorescence imaging for the plurality of microdroplets can be achieved by the fluorescence signal detecting device 30. A number of fluorescence images showing the plurality of microdroplets can be photographed at one time. An image processing technique can be used to automatically identify the fluorescence of the microdroplets from the image to obtain the fluorescence information of the microdroplets. The microdroplet container 60 is irradiated at the oblique angle from the above of the microdroplet container 60. The fluorescence signal detecting device 30 is used to periodically scan the plurality of microdroplets in two dimensions and to take the image in real time. The oblique light path can effectively reduce the scattering background of the exciting lights and increase the sensitivity of the fluorescence detection. The plurality of microdroplets in the microdroplet container 60 are excited to generate fluorescence. The fluorescence is entered into the camera which captures the fluorescence image of the plurality of microdroplets.

The conventional microdroplet containers have the problems of high cost of consumables, small containing number of the microdroplets, and concave surface, which affects the imaging and detection, of the liquid in the microdroplet container. In view of these problems, a microdroplet container having low cost of consumables, being capable of accommodating a large number of microdroplets, and conducive to imaging and detection is provided.

Referring to FIG. 32 to FIG. 37, an embodiment of the present application provides a microdroplet container 60 including a bottom surface 611, a first surrounding side surface 621 surrounding the bottom surface 611 and a surrounding surface 641. The first surrounding side surface 621 is connected to and surrounds the bottom surface 611 to form a receiving space 630 having an opening 631. The first surrounding side surface 621 is perpendicular to the bottom surface 611. The surrounding surface 641 surrounds the opening 631 and is connected to the first surrounding side surface 621. The surrounding surface 641 is parallel to the bottom surface 611. The surrounding surface 641 being parallel to the bottom surface 611 is to ensure that the surface of the liquid in the microdroplet container 60 is a horizontal flat surface. By having the surrounding surface 641, the surface of the liquid in the microdroplet container 60 can be in the flat state, and the overall surface of the liquid in the microdroplet container 60 is prevented from being curved. Therefore, the observation of the microdroplets adjacent to the edge of the container bottom plate will not be affected by the microdroplet container 60, facilitating camera imaging and improving detection efficiency of the plurality of microdroplets.

In an embodiment, the microdroplet container 60 further includes a container bottom plate 610, a first surrounding side plate 620 surrounding the container bottom plate 610, and a surrounding member 640. The surface of the container bottom plate 610 is the bottom surface 611. The inner surface of the first surrounding side plate 620 is the first surrounding side surface 621. The first surrounding side plate 620 is fixedly connected to the container bottom plate 610, and defines the receiving space 630 together with the container bottom plate 610. The surface of the surrounding member 640 is the surrounding surface 641. The surrounding member 640 is fixedly connected to an end of the first surrounding side plate 620, the end is away from the container bottom plate 610. The surrounding member 640 is parallel to the container bottom plate 610.

The second liquid (the oil phase composition) is firstly placed in the microdroplet container 60 before the microdroplet generating device 10 generates the plurality of microdroplets. When the liquid surface of the second liquid is at the same level of the horizontal surface of the surrounding surface 641, the adding of the second liquid is stopped. At this time, the liquid surface of the second liquid and the surface of the surrounding surface 641 are at the same horizontal plane, which can ensure that the liquid surface of the second liquid in the microdroplet container 60 is flat, and conveniently ensure that the top surface of the oil phase above the bottom surface of the container is a horizontal flat surface. This facilitates the imaging, and increases the utilization rate of the microdroplet container 60, which can be used to accommodate more and a larger number of microdroplets.

In an embodiment, an inner periphery of the surrounding member 640 is connected to an end of the first surrounding side plate 620, the end is away from the container bottom plate 610. The microdroplet container 60 further includes a second surrounding side plate 650. The second surrounding side plate 650 surrounds the surrounding member 640 and is fixedly connected to the surrounding member 640. A radius of the second surrounding side plate 650 is larger than an inner radius of the surrounding member 640.

The receiving space 630 can be defined by the surrounding member 640, the first surrounding side plate 620, the container bottom plate 610, and the second surrounding side plate 650, respectively in cooperation with the surrounding surface 641, the first surrounding side surface 621, and the bottom surface 611. The receiving space 630 is configured to accommodate the second liquid (the oil phase composition). The liquid surface of the second liquid and the surface of the surrounding surface 641 are at the same horizontal plane, which can ensure that the liquid surface of the second liquid in the microdroplet container 60 is flat, and conveniently ensure that the top surface of the oil phase above the bottom surface of the container is a horizontal flat surface. This avoids the problem that the overall surface of the liquid in the conventional microdroplet container is curved, and avoids the problem that the liquid surface is a concave liquid surface. Therefore, it is more convenient for the imaging by the fluorescence signal detecting device 30 in the fluorescence detection of the plurality of microdroplets. The microdroplet container 60 can be used to accommodate more and a larger number of microdroplets, which increases the utilization rate of the microdroplet container 60.

In an embodiment, an outer periphery of the surrounding member 640 is connected to an end of the first surrounding side plate 620, the end is away from the container bottom plate 610.

In an embodiment, the outer periphery of the first surrounding side plate 620 is fixedly connected to the first surrounding side surface 621. By connecting the surrounding member 640 and the first surrounding side plate 620, a horizontal platform can be formed in the microdroplet container 60. After the second liquid is added into the microdroplet container 60, the liquid surface of the second liquid and the surface of the surrounding surface 641 can be at the same horizontal plane, which can ensure that the liquid surface of the second liquid in the microdroplet container 60 is flat, and conveniently ensure that the top surface of the oil phase above the bottom surface of the container is a horizontal flat surface. This avoids the problem that the overall surface of the liquid in the conventional microdroplet container is curved, and avoids the problem that the liquid surface is a concave liquid surface. Therefore, it is more convenient for the imaging by the fluorescence signal detecting device 30 in the fluorescence detection of the plurality of microdroplets. The microdroplet container 60 can be used to accommodate more and a larger number of microdroplets, which increases the utilization rate of the microdroplet container 60.

In an embodiment, the microdroplet container 60 further includes a third surrounding side plate 660. One end of the third surrounding side plate 660 is fixedly connected to the bottom surface 611. The other end of the third surrounding side plate 660 is fixedly connected to the inner periphery of the first surrounding side plate 620. The third surrounding side plate 660 and the container bottom plate 610 together surround and define the receiving space 630.

In an embodiment, the third surrounding side plate 660 is perpendicular to the container bottom plate 610. Through arranging the third surrounding side plate 660 in the microdroplet container 60, the liquid surface of the second liquid and the surface of the surrounding surface 641 can be at the same horizontal plane, so that the liquid surface in the microdroplet container 60 is a flat surface, avoiding the concave liquid surface in the conventional art, facilitating the imaging, and improving the utilization rate of the microdroplet container 60.

In an embodiment, the microdroplet container 60 further includes a plurality of surrounding ridges 613 disposed on the bottom surface 611 and spaced from each other. Each surrounding ridge 613 and the bottom surface 611 surround and define a microdroplet reservoir 614. The microdroplet reservoir 614 is configured to store the generated plurality of microdroplets. The multiple microdroplets are spread on the bottom surface 611 by a method for spreading the microdroplets to form a single layer of microdroplets for imaging and observation. Moreover, the space between the plurality of microdroplet reservoirs 614 can be determined according to the distance between the parallel syringes of the microdroplet generating device 10, so that a plurality of microdroplets can be formed in the plurality of microdroplet reservoirs 614 at the same time. The capacity of the microdroplet container 60 is improved, and it can also be used to detect different kinds of nucleic acids.

In an embodiment, a height of the plurality of surrounding ridges 613 is 0.1 mm to 1 mm. By setting the height of the surrounding ridges 613, the shadow caused by the excitation light irradiated from the side can be eliminated, so that the camera can acquire fluorescence information of all microdroplets, and the sensitivity of the fluorescence detecting device is improved.

In an embodiment, the inner surface of the microdroplet reservoir 614 is provided with an oleophobic layer. By performing an oleophobic treatment to the surface of the container bottom plate 610, the adhesion between the bottom plate 610 and the microdroplets is reduced, the surface tension is reduced, the frictional force is reduced, and the microdroplets are easy to slip, so that the microdroplets can automatically spread to prevent the accumulation of the plurality of microdroplets. Moreover, the plurality of microdroplets can spread more quickly, which is beneficial to the spreading of the plurality of microdroplets on the bottom plate 610 of the microdroplet container. When the surface tension of the container bottom plate is smaller than the surface tension of the second liquid (the oil) 699, the resistance force between the microdroplets and the bottom plate becomes smaller, and the microdroplets can automatically diffuse toward the bottom of the microdroplet reacting unit to achieve the flat spreading.

An oleophobic film is also called the oleophobic layer, which is a composite coating material and is a functional material coating often having an oleophobic function. The oleophobic layer is a coating on the surface formed by using a spray-coating technique with nano-silica ($SiO_2$) as a raw material. The oleophobic layer has good light transmittance, hydrophobicity, and oleophobicity. When the plurality of microdroplets are in contact with the reacting unit, the contact angle of the microdroplets can reach 90 degrees, and the microdroplets can automatically settle without leaving traces, so that the plurality of microdroplets can be spread on the microdroplet container bottom plate 610.

In an embodiment, a microdroplet generating kit includes the microdroplet container 60 described in the above embodiments, a sealing cover 670, and oil phase composition. The oil phase composition is disposed in the receiving space 630. The sealing cover 670 is disposed on the opening 631 to seal the receiving space 630.

In an embodiment, each reacting unit 612 includes one surrounding ridge 613. The microdroplet reservoir 614 is surrounded and formed by the surrounding ridge 613 and the bottom surface 611. The container bottom plate 610 is provided with a plurality of reacting units 612, and each reacting unit 612 can accommodate a plurality of microdroplets, so that the microdroplet container 60 can accommodate a large number of microdroplets, which can far exceed 20,000 in an actual detection. The number of the microdroplets is not limited.

In an embodiment, the plurality of the reacting units 612 are rectangular in shape. The microdroplet container 60 has a square or rectangular shape. Since most of the film or digital photosensitive elements (CCD or CMOS) are square in shape, the square shaped microdroplet container 60 can improve the space utilization of the microdroplet container, and the formed fluorescence images are easy to be spliced to achieve a real-time tracking.

In an embodiment, the plurality of reacting units 612 are arranged at equal intervals on the container bottom plate 610. The space between the reacting units 612 is the same as the distance between the parallel syringes of the microdroplet generating device 10, so that a plurality of microdroplets can be formed in the plurality of reacting units 612 at the same time, increasing the microdroplet generating speed and saving time. Moreover, a plurality of microdroplets with different volumes can be generated in the plurality of reacting units 612 through the microdroplet generating device 10.

In an embodiment, the height of the plurality of surrounding ridges 613 is 0.1 mm to 1 mm. By setting the height of the surrounding ridge 613, the shadow caused by the excitation light irradiated from the side can be eliminated, so that the camera can acquire fluorescence information of all microdroplets, and the sensitivity of the fluorescence detection device is improved.

In the conventional digital PCR detection system, each independent reacting unit usually contains one microdroplet; moreover, the number of the droplets in the actual detection will not reach 20,000, and there is still a limit to the number of the microdroplets. Theses problems can be solved by using the microdroplet container 60, which does not have a limit to the number of the microdroplets.

Therefore, the plurality of reaction units 612 on the container bottom plate 610 can accommodate a large number of microdroplets, increasing the storage capacity of the microdroplet container 60, realizing the detection of more than 20,000 microdroplets, and being capable of detecting different types of nucleic acids. Through the peripheral frame of the reacting unit, the scattering the plurality of microdroplets into the adjacent reacting unit 612 can be avoided.

In an embodiment, the cross-section of the microdroplet container 60 is rectangular. The microdroplet container 60 has a square or rectangular shape. The shape of the microdroplet container 60 is consistent with the shape of the camera lens, which improves the space utilization of the microdroplet container and facilitates the splicing of the formed fluorescent images to realize a real-time tracking.

In an embodiment, the surrounding member 640 is a square frame.

By performing an oleophobic treatment to the surface of the container bottom plate 610, the adhesion between the bottom plate 610 and the microdroplet is reduced, the surface tension is reduced, and the frictional force is reduced, and the microdroplets are easy to slip, so that the microdroplets can automatically spread to prevent the accumulation of the plurality of microdroplets. Moreover, the plurality of microdroplets can spread more quickly, which is beneficial to the spreading of the plurality of microdroplets on the bottom plate 610 of the microdroplet container. When the surface tension of the container bottom plate is smaller than the surface tension of the second liquid (the oil) 699, the resistance force between the microdroplets and the bottom plate becomes smaller, and the microdroplets can automatically diffuse toward the bottom of the microdroplet reacting unit to achieve a flat spreading.

An oleophobic film is also called the oleophobic layer, which is a composite coating material and is a functional material coating often having an oleophobic function. The oleophobic layer is a coating on the surface formed by using a spray-coating technique with nano-silica ($SiO_2$) as a raw material. The oleophobic layer has good light transmittance, hydrophobicity, and oleophobicity. When the plurality of microdroplets are in contact with the reacting unit, the contact angle of the microdroplets can reach 90 degrees, and the microdroplets can automatically settle without leaving traces, so that the plurality of microdroplets can be spread on the microdroplet container bottom plate 610.

In an embodiment, a height of the first surrounding side plate 620 or the second surrounding side plate 650 is 5 mm to 15 mm. By having the height of the first surrounding side plate 620 or the second surrounding side plate 650 in such range, the microdroplets can be prevented from being thrown out from the microdroplet generating device 10 during the generation of the plurality of microdroplets. Moreover, the shadow caused by the excitation light irradiated from the side can be eliminated, so that the camera can acquire fluorescence information of all microdroplets, and the sensitivity of the fluorescence detecting device can be improved.

In an embodiment, a material of the container bottom plate 610 is glass, quartz, stainless steel, or the like.

In an embodiment, the material of the container bottom plate 610 is glass, which is cheap to lower the cost of consumables.

If a large number of microdroplets are to be detected, the glass made microdroplet container 60, which is cheap with low cost of consumables, can be discarded after one use, preventing cross-contamination, saving the time, and improving the detection efficiency of the digital PCR detection apparatus 1.

In an embodiment, a material of the surrounding ridge 613 is the same as that of the bottom plate 610 of the microdroplet container. Using this technique, a plurality of reacting units 612 can be formed on the microdroplet container bottom plate 610. The plurality of reacting units 612 are arranged on the bottom plate 610 of the microdroplet container as an array to form a plurality of nucleic acid amplification units.

In an embodiment, a shape and size of the container bottom plate 610 are consistent with the shape and size of a 24-well plate or a 96-well plate, so that the microdroplet container 60 can be conveniently used in other models of instruments, and be more practical and compatible.

In an embodiment, a material of the first surrounding side plate 620 or the second surrounding side plate 650 is a non-fluorescent black silicone rubber with high-temperature resistance, low-temperature resistance, and oil resistance. The black silicone rubber has the characteristics of being odorless, non-toxic, high temperature tolerance, and being resistant to severe cold. Moreover, the black silicone rubber has advantages such as good electrical insulation, oxygen aging resistance, light aging resistance, mildew resistance, and chemical stability, and has received attention from the field of modem medicine.

The microdroplet container 60 made of glass or stainless steel can reduce the detection cost. Moreover, the plurality of reaction units 612 on the container bottom plate 610 can accommodate a large number of microdroplets, increasing the storage capacity of the microdroplet container, which can realize a detection for more than 20,000 microdroplets, and can detect different types of nucleic acids, and is cost effective.

When the excitation light is obliquely irradiated on the microdroplet container 60 to irradiate the multiple microdroplets, the oblique light path formed from the excitation light source can effectively reduce the excitation light scattering background. Moreover, decreasing the height of the first surrounding side plate 620 or the second surrounding side plate 650 of the microdroplet container 60 is beneficial to eliminate the shadow caused by the excitation light irradiated from the side, so that the camera of the fluorescence signal detecting device 30 can acquire fluorescence information of all microdroplets, and the sensitivity of the fluorescence detecting device 30 is improved.

Figure 38:
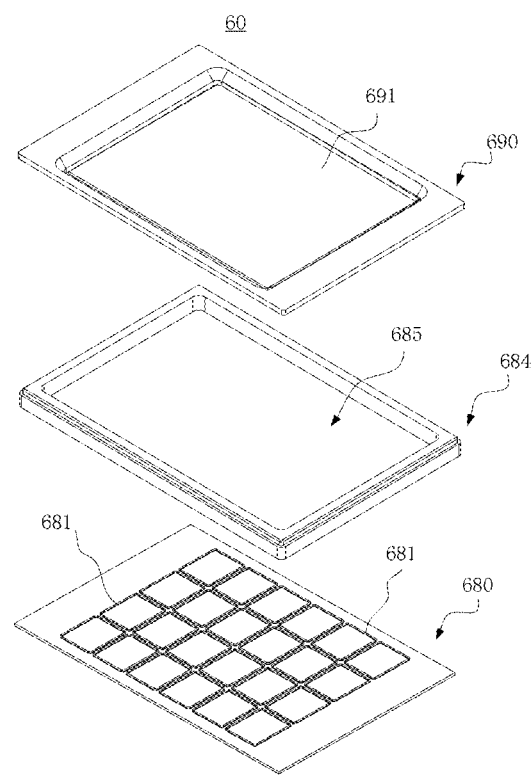
FIG. 38 is an overall schematic structural view of a microdroplet container of the present application.
Figure 39:
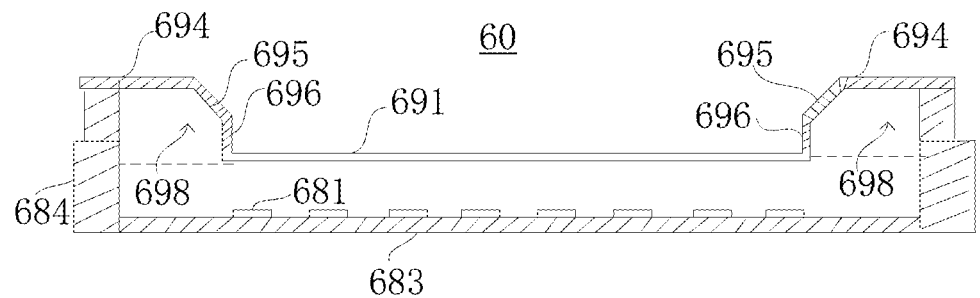
FIG. 39 is a schematic structural cross-sectional view of a microdroplet container of the present application.

Referring to FIGS. 38 to 39, in an embodiment, the present application provides a microdroplet container 60 including a first container bottom plate 680, a polygonal frame 684, and a container lid 690. The first container bottom plate 680 includes a plurality of polygonal ridges 681. The polygonal frame 684 surrounds and defines a first receiving space 685. The polygonal frame 684 is connected to the first container bottom plate 680, and the plurality polygonal ridges 681 are disposed in the first receiving space 685. The container lid 690 is disposed on the surface of the polygonal frame 684, the surface is away from the first container bottom plate 680. The container lid 690 is detachably connected to the polygonal frame 684. The container lid 690 and the polygonal frame 684 surround and define an oil reservoir 698.

Two sides of the polygonal frame 684 are respectively connected to the first container bottom plate 680 and the container lid 690. The container lid 690 is detachably connected to the polygonal frame 684 to seal the microdroplet container 60. The shape of the plurality of polygonal ridges 681 can be polygonal such as square, rectangle, and pentagonal. The container lid 690 and the polygonal frame 684 surround and define the oil reservoir 698. When the microdroplet container 60 is sealed by the container lid 690, excess oil in the microdroplet container 60 can be squeezed into the oil reservoir 698, so that the affecting of the oil above the microdroplets on the detection process can be avoided as much as possible, and the fluorescent background caused by the oil can be avoided. Moreover, by squeezing the excess oil from the microdroplet container 60 into the oil reservoir 698, the amount of the oil remained in the microdroplet container 60 around the microdroplets is reduced, so as to prevent the water-unsaturated oil absorbing water from the microdroplets, and to avoid the water diminishing of the microdroplets.

Air may be mixed and bubbles may be generated in the oil liquid accommodated by the microdroplet container 60, which may affect the fluorescence signal detecting device 30 taking images of the fluorescence variations of the plurality of microdroplets in in real time. Therefore, by sealing the microdroplet container 60, when the microdroplet container 60 is oblique at an angle of 3 degrees to 5 degrees, the liquid in the microdroplet container 60 can be prevented from flowing out, and the bubbles in the microdroplet container 60 can also be discharged to avoid the bubbles affecting the images in the imaging and detection.

Figure 40:
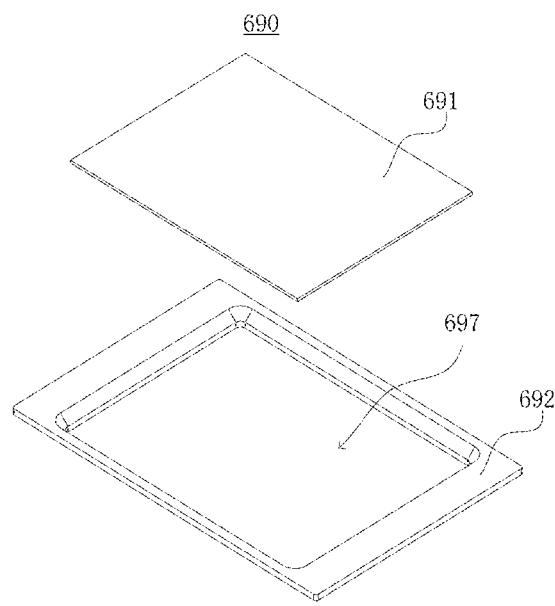
FIG. 40 is a schematic structural view of a container lid of a microdroplet container of the present application.
Figure 41:
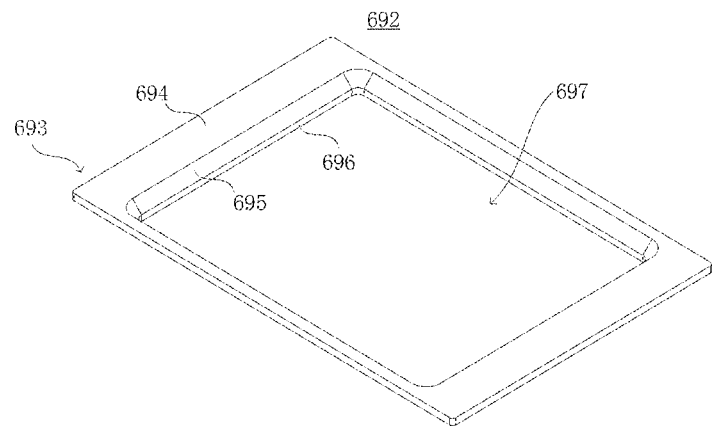
FIG. 41 is a schematic structural view of a polygonal lid frame of a microdroplet container of the present application.
Figure 42:
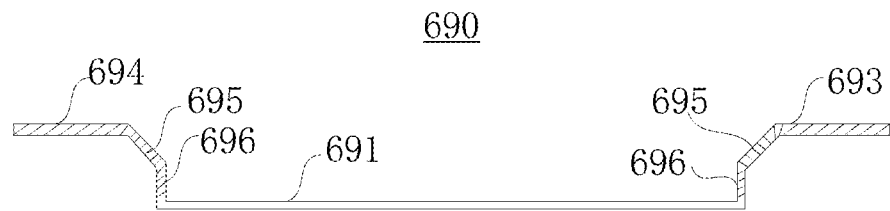
FIG. 42 is a schematic structural cross-sectional view of a container lid of a microdroplet container of the present application.

Referring to FIGS. 40 to 42, in an embodiment, the container lid 690 includes a flat board 691 and a polygonal lid frame 692. The flat board 691 is transparent. The polygonal lid frame 692 surrounds and defines a mounting space 697 for mounting the flat board 691.

In an embodiment, the flat board 691 is a glass board. The flat board 691 and the polygonal lid frame 692 can be fixed together by glue that is water-resistant, high-temperature resistant, non-fluorescent, non-toxic, and has no inhibitory effect on the PCR reaction. The flat board 691 is a glass plate, which is cheap with low cost of consumables. If a large number of microdroplets are to be detected, the glass made microdroplet container 60, which is cheap with low cost of consumables, can be discarded after one use, preventing cross-contamination, saving the time, and improving the detection efficiency of the digital PCR detection apparatus.

In an embodiment, the polygonal lid frame 692 includes a main body 693 of the polygonal lid frame, a plurality of extending members 695, and a plurality of flat board mounting frame members 696. The main body 693 of the polygonal lid frame includes a plurality of peripheral frame members 694. The plurality of peripheral frame members 694 are fixedly connected to one another. The extending members 695 are one-to-one fixedly connected to the peripheral frame members 694, and extend obliquely toward the mounting space 697. The flat board mounting frame members 696 are one-to-one fixedly connected to the extending members 695 and extend toward the first receiving space 685 defined by the polygonal frame 684.

In an embodiment, the plurality of peripheral frame members 694 are fixedly connected to form the main body 693 of the polygonal lid frame. The angle formed by the surface of the peripheral frame member 694 and the surface of the extending member 695 is greater than 90 degrees, so that the oil reservoir 698 is formed when the container lid 690 is mounted on the polygonal frame 684. By squeezing the excess oil in the microdroplet container 60 into the oil reservoir 698, the affecting on the detection process by the oil above the microdroplets can be avoided as much as possible, and the fluorescent background caused by the oil can be avoided.

In an embodiment, the plurality of extending members 695 are fixedly connected in sequence to form an annular frame, and fixedly connected to the main body 693 of the polygonal lid frame. The plurality of flat board mounting frame members 696 are fixedly connected in sequence to form an annular frame, and are fixedly connected to the annular frame formed by the plurality of extending members 695. The polygonal lid frame 692 is one piece.

In an embodiment, the angle between the surface of the extending member 695 and the surface of the flat board mounting frame member 696 is greater than 90 degrees. The angle between the surface of the flat board mounting frame member 696 and the surface of the peripheral frame member 694 is 90 degrees. That is to say, the flat board mounting frame member 696 is perpendicular to the liquid surface of the oil liquid in the microdroplet container 60. In this way, a rectangular interface having the same shape as the camera lens can be formed by mounting the flat board 691, and the liquid surface in the microdroplet container 60 can be flat, avoiding the overall curved liquid surface in the microdroplet container 60. Therefore, the microdroplet container 60 does not affect the observation of the microdroplets adjacent to the edge of the first container bottom plate 680, which facilitates the camera to take images and improves the detection efficiency of the plurality of microdroplets. In addition, the utilization rate of the microdroplet container 60 is increased by the microdroplet container 60 to accommodate a larger number of microdroplets.

When the microdroplet container 60 is sealed by the container lid 690, excess oil in the microdroplet container 60 can be squeezed into the oil reservoir 698, so that the effect of the oil above the microdroplets on the detection process can be avoided as much as possible.

Figure 43:
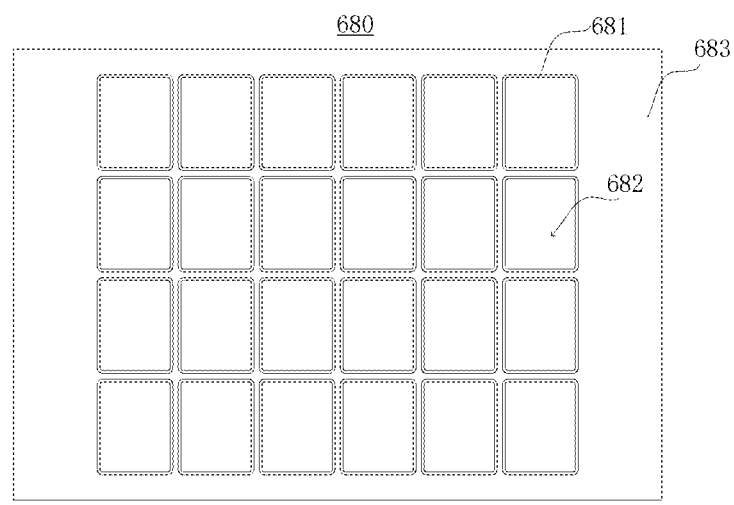
FIG. 43 is a schematic structural view of a first container bottom plate of a microdroplet container of the present application.
Figure 44:
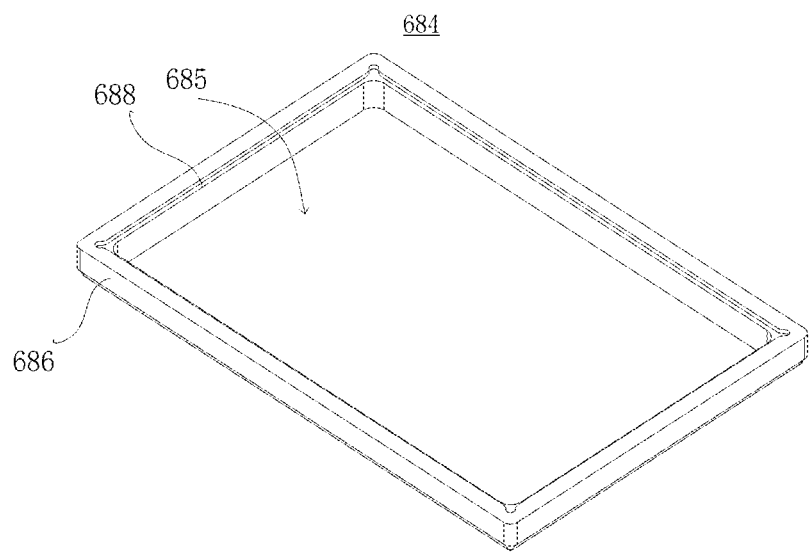
FIG. 44 is a schematic structural view of support members of a polygonal frame of a microdroplet container of the present application.
Figure 45:
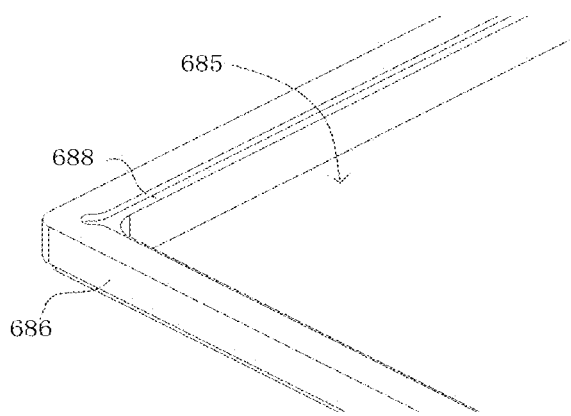
FIG. 45 is a schematic structural enlarged local view of support members of a polygonal frame of a microdroplet container of the present application.
Figure 46:
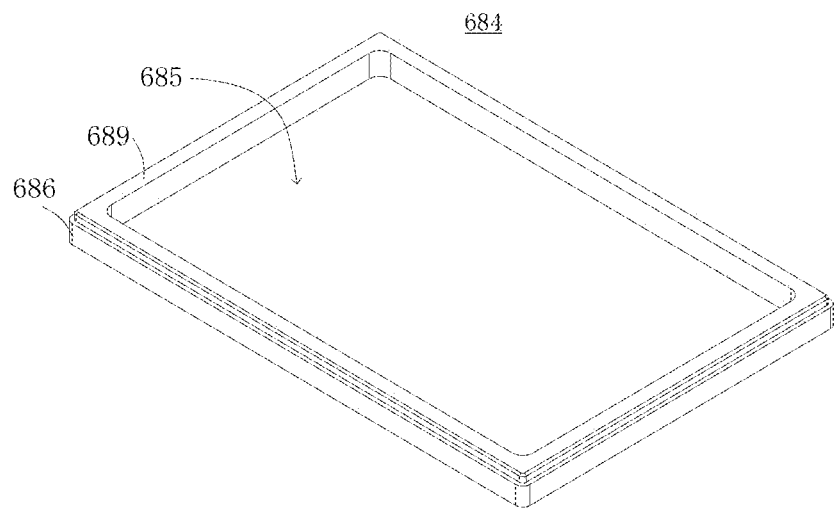
FIG. 46 is a schematic structural view of second support strips of a polygonal frame of a microdroplet container of the present application.
Figure 47:
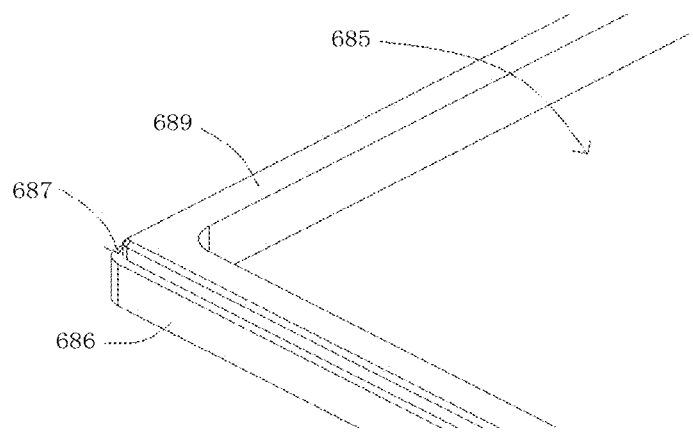
FIG. 47 is a schematic structural enlarged local view of second support strips of a polygonal frame of a microdroplet container of the present application.

Referring to FIG. 43, in an embodiment, the first container bottom plate 680 further includes a substrate 683. The plurality of polygonal ridges 681 are arranged as an array on the first surface of the substrate 683 adjacent to the polygonal frame 684. Each polygonal ridge 681 and the surface of the substrate 683 surround and define one first microdroplet reservoir 682, the surface being adjacent to the polygonal frame 684.

In an embodiment, the plurality of the reacting units 681 are rectangular in shape. The microdroplet container 60 has a square or rectangular shape. Since most of the film or digital photosensitive elements (CCD or CMOS) are square in shape, the square shaped microdroplet container 60 can improve the space utilization of the microdroplet container, and the formed fluorescence images are easy to be spliced to achieve a real-time tracking.

The plurality of polygonal ridges 681 are arranged as an array on the surface of the substrate 683, the surface is adjacent to the peripheral frame member 684. Each of the polygonal ridges 681 and the substrate 683 surround and define one first microdroplet reservoir 682. The first microdroplet reservoir 682 is configured to store the generated plurality of microdroplets, and the plurality of microdroplets are spread on the first container bottom plate 680 through a method for spreading microdroplets to form a single layer of microdroplets or multilayers of microdroplets for imaging and observation. Moreover, the space between the plurality of polygonal ridges 681 can be set according to the distance between the parallel syringes of the microdroplet generating device 10, so that a plurality of first microdroplet can be formed in the plurality of microdroplet reservoirs 682 at the same time, increasing the accommodating capacity of the microdroplet container 60, which can also be used to detect different types of nucleic acids.

In an embodiment, a height of each polygonal ridge 681 is 0.2 mm to 0.8 mm.

The height of each polygonal ridge 681 is 0.2 mm to 0.8 mm, and the optimal height can be 0.3 mm to 0.5 mm. In the detection process, considering that the plurality of microdroplets need to be placed in the first microdroplet reservoir 682 and no microdroplet can be out of the reservoir, the height of each polygonal ridge 681 cannot be too small. Therefore, the height of the polygonal ridge 681 is at least equal to or larger than the diameter of one microdroplet. In the capturing of the microdroplet image by using the fluorescence detecting device 30, two or more layers of microdroplets can be formed in the first microdroplet reservoir 682 of the microdroplet container 60, which can expand the detection range of the digital PCR detection apparatus, and is conducive to handling large quantities of microdroplets. The nucleic acid amplification reaction liquid is dropletized by the microdroplet generating device 10 to form the plurality of microdroplets, and the diameter of each microdroplet is generally between 0.1 mm and 0.2 mm. For the reason that multiple layers of microdroplets or microdroplet stack can occur in the detection, the height of the polygonal ridge 681 is usually equal to or larger than two times of the diameter of one microdroplet, in order to avoid the microdroplet generating device 10 throwing the microdroplets out in the process of generating the microdroplets. Moreover, the shadow caused by the excitation light irradiated from the side can be eliminated, so that the fluorescence signal detecting device 30 can acquire fluorescence information of all microdroplets, and the sensitivity of the fluorescence signal detecting device 30 is improved.

Moreover, the height of each polygonal ridge 681 will not affect the image capture when the fluorescence detection device 30 is adopted to capture images of the microdroplets, which can be beneficial to eliminate the shadow caused by the excitation light irradiated from the side, so that the camera can acquire fluorescence information of all microdroplets, and the sensitivity of the fluorescence signal detecting device 30 is improved.

In an embodiment, the inner surface of the first microdroplet reservoir 682 formed by the plurality of polygonal ridges 681 is provided with an oleophobic layer. In other words, the oleophobic layer is disposed on the surfaces of the plurality of polygonal ridges 681, the surfaces are adjacent to the first microdroplet reservoir 682.

By performing an oleophobic treatment to the surface of the substrate 683, the adhesion between the substrate 683 and the microdroplet is reduced, the surface tension is reduced, and the frictional force is reduced, and the microdroplets are easy to slip, so that the microdroplets can automatically spread to prevent the accumulation of the plurality of microdroplets. Moreover, the plurality of microdroplets can spread more quickly, which is beneficial to the spreading of the plurality of microdroplets on the substrate 683. When the surface tension of the substrate 683 is smaller than the surface tension of the oil, the resistance force between the microdroplets and the bottom plate becomes smaller, and the microdroplets can automatically diffuse toward the bottom of the first microdroplet reservoir 682 to achieve the flat spreading.

The oleophobic film is also called the oleophobic layer, which is a composite coating material and is a functional material coating often having an oleophobic function. The oleophobic layer is a coating on the surface formed by using a spray-coating technique with nano-silica ($SiO_2$) as a raw material. The oleophobic layer has good light transmittance, hydrophobicity, and oleophobicity. When the plurality of microdroplets are in contact with the reacting unit, the contact angle of the microdroplets can reach 90 degrees, and the microdroplets can automatically settle without leaving traces, so that the plurality of microdroplets can be spread on the substrate 683.

In an embodiment, a shape and size of the substrate 683 are consistent with the shape and size of a 24-well plate or a 96-well plate, so that the microdroplet container 60 can be conveniently used in other models of instruments, and be more practical and compatible.

The plurality of first microdroplet reservoirs 682 formed by the polygonal ridges 681 can accommodate a plurality of microdroplets, so that the microdroplet container 60 can accommodate a large number of microdroplets, which can far exceed 20,000 in an actual detection. The number of the microdroplets is not limited.

When the container lid 690 seals the microdroplet container 60, the distance between the flat board 691 and the microdroplets in the first microdroplet reservoir 682 cannot be too large, and the distance is generally in a range from 1 mm to 2 mm, so that the effect on the image of the microdroplets caused by the oil above the microdroplets can be avoided, and the fluorescent background caused by the oil can be avoided, and the spreading of the plurality of microdroplets on the substrate 683 is benefitted. Moreover, the excess oil in the microdroplet container 60 is squeezed into the oil reservoir 698, the amount of the oil remained in the microdroplet container 60 around the microdroplets is reduced, so as to prevent the water-unsaturated oil absorbing water from the microdroplets, and to avoid the water diminishing of the microdroplets.

Referring to FIGS. 44 to 47, in an embodiment, the polygonal frame 684 includes a plurality of first support strips 686, a plurality of support members 688, and a plurality of second support strips 689. The first support strips 686 are connected as an annulus. The support members 688 are one-to-one fixedly disposed on the inner walls of the first support strips 686 and extend toward the first receiving space 685. The plurality of support members 688 are connected as an annulus to support the first container bottom plate 680. The second support strips 689 are fixedly disposed one-to-one on the first support strip surfaces 687 of the first support strips 686, the first support strip surface 687 being away from the first container bottom plate 680. The plurality of second support strips 689 are connected as an annulus. The plurality of second support strips 689 and the plurality of first support strips 686 together surround and define the first receiving space 685. The plurality of second support strips 689 and the plurality of the peripheral frame members 694 of the main body 693 of the polygonal lid frame are detachably connected.

The support members 688 are one-to-one fixedly disposed on the inner walls of the first support strips 686 and extend toward the first receiving space 685. The plurality of support members 688 are connected as an annulus to support the first container bottom plate 680. The first container bottom plate 680 is mounted on the annular support frame formed by the plurality of support members 688, having the plurality of polygonal ridges 681 disposed in the first receiving space 685.

Referring to FIG. 48, the polygonal frame 684 and the container lid 690 are adhered by a double-side tape 699. That is to say, the double-side tape 699 is adhered on the surface of the polygonal frame formed by the plurality of annularly connected second support strips 689. The double-side tape 699 facilitates the connection with the first surface of the peripheral frame member 694, the first surface being adjacent to the polygonal frame 684, so that the polygonal frame 684 is seal-connected to the container lid 690.

In an embodiment, the substrate 683 and the flat board 691 of the microdroplet container 60 are both glass boards, which solves the consumables problem of the sample container in the detection using the digital PCR detection apparatus and saves costs. Moreover, due to the height setting of each member of the microdroplet container 60, the overall thickness of the microdroplet container 60 is relatively small, and the availability of a large number of microdroplets is increased. The temperature of the microdroplet container 60 can be rapidly cycled between high and low temperatures, and is convenient for observation and detection.

In an embodiment, the width of each second support strip 689 is smaller than the width of each first support strip 686 to form a gap away from the first receiving space 685 to facilitate disassembling.

The polygonal frame 684 is integrally formed. The side surface of the second support strip 689 and the side surface of the first support strip 686 are not on the same plane, which can prevent excess glue from being squeezed out when adhering the container lid 690 to the polygonal frame 684, avoiding sticking to hands or other places. The width of each second support strip 689 is smaller than the width of each first support strip 686 to form a gap away from the first receiving space 685 to facilitate disassembling.

In an embodiment, a method for manufacturing microdroplet container includes:
S510, providing a substrate 683;
S5520, forming the plurality of polygonal ridges 681 on a surface of the substrate 683, thereby forming a first container bottom plate 680;
S530, providing a polygonal frame 684, and connecting the first container bottom plate 680 to the polygonal frame 684;
S540, providing a container lid 690, and adhering the container lid 690 on the surface, away from the first container bottom plate 680, of the polygonal frame 684 for sealing, thereby forming the microdroplet container.

In an embodiment, the substrate 683 without having the polygonal ridges 681 formed thereon can be firstly joined to the polygonal frame 684 by adhesive. Then, the oil liquid is filled into the container formed by the substrate 683 and the polygonal frame 684 adhered with each other. Next, the plurality of polygonal ridges 681 are formed by dropping and applying a fluid on the surface, adjacent to the polygonal frame 684, of the substrate 683 by an adhesive dispenser, which can realize a three-dimensional path or a four-dimensional path adhesive dispensing, precise positioning, precise controlling, no wire drawing, no leakage, and no dripping.

Next, a large number of microdroplets are generated in the polygonal ridges 681 by the microdroplet generating device 10 of the digital PCR detection apparatus. Finally, the polygonal frame 684 and the container lid 690 are connected, such as adhered by a double-sided adhesive. The double-sided adhesive can be set into a polygonal shape, so that the polygonal frame 684 and the container lid 690 can be fully adhered.

In an embodiment, the plurality of polygonal ridges 681 can be firstly formed on the surface of the substrate 683, the surface being adjacent to the polygonal frame 684. When forming the polygonal ridges 681, the polygonal ridges 681 can be formed on the surface, adjacent to the polygonal frame 684, of the substrate 683 by using a dispenser, though printing, though screen printing, etc., and the polygonal ridges 681 are arranged as an array, thereby forming the first container bottom plate 680. Then, the first container bottom plate 680 and the polygonal frame 684 are adhesively connected. Next, the oil liquid is filled into the container formed by the first container bottom plate 680 and the polygonal frame 684 adhered with each other. Next, a large number of microdroplets are generated in the polygonal ridges 681 by the microdroplet generating device 10 of the digital PCR detection apparatus. Finally, the polygonal frame 684 and the container lid 690 are connected, such as adhered by a double-sided adhesive. The double-sided adhesive can be set into a polygonal shape, so that the polygonal frame 684 and the container lid 690 can be fully adhered.

In an embodiment, in step S520, the polygonal ridges 681 can be formed by the method such as dispensing, spray printing, screen printing, and hot-pressing molding.

In an embodiment, the material of the polygonal ridge 681 is a polymer that is resistant to high temperatures, low temperatures, and oils, and has no fluorescence, in order to avoid affecting the high-low temperature cycling and fluorescent imaging of the microdroplets by the polygonal ridges 681.

In an embodiment, the polygonal ridges 681 can be made of a black silicone rubber or a silicone sealant.

The plurality of polygonal ridge 681 are made of a black silicone rubber that is resistant to high and low temperatures, oils, and has no fluorescence, so that when the microdroplet is fluorescently imaged, the fluorescent influence caused by the polygonal ridges 681 can be avoided. The black silicone rubber has the characteristics of being odorless, non-toxic, high temperature tolerance, and being resistant to severe cold. Moreover, the black silicone rubber has advantages such as good electrical insulation, oxygen aging resistance, light aging resistance, mildew resistance, and chemical stability, and has received attention from the field of modem medicine. The plurality of polygonal ridges 681 are formed by dropping and applying the fluid on the surface, adjacent to the polygonal frame 684, of the substrate 683 by the adhesive dispenser, which can realize a three-dimensional path or a four-dimensional path adhesive dispensing, precise positioning, precise controlling, no wire drawing, no leakage, and no dripping.

The silicone sealant has the characteristics of weather resistance, vibration resistance, moisture resistance, odor resistance, large adaptability to cold and heat changes, and being antiseepage and leakproof.

In an embodiment, in step S520, the polygonal ridges 681 can be formed by injection molding or hot-pressing molding.

In an embodiment, an analysis method using the digital PCR detection apparatus includes the following steps: S10, preparing a nucleic acid amplification reaction liquid to be tested; S20, microdropletizing the nucleic acid amplification reaction liquid to be tested into the plurality of microdroplets; S30, amplifying nucleic acids in the plurality of microdroplets and acquiring fluorescence information of the plurality of microdroplets in real time; S40, performing quantitative analysis on the plurality of microdroplets according to the fluorescence information of the plurality of microdroplets.

In an embodiment, in the step 520, two microdroplet generating methods can be used to microdropletize the nucleic acid amplification reaction liquid to be tested to form the plurality of microdroplets: the microdroplet generating method with the instantaneous accelerated speed and the microdroplet generating method with the periodically changed speed. The step S30 includes: S310, spreading the plurality of microdroplets in the microdroplet container; S320, amplifying the nucleic acids in the spread microdroplets; S330, imaging and detecting the plurality of microdroplets in real time during the nucleic acid amplification.

It is not conducive to observation on the condition that the plurality of microdroplets generated by the microdroplet generating device 10 are aggregated and gathered together in the middle of the microdroplet container 60 during the downward settlement process. A microdroplet spreading method is provided to address the problem of the microdroplets gathering at the bottom of the microdroplet container.

Referring to FIG. 49, in an embodiment, the step S30 includes: S310, spreading the plurality of microdroplets in the microdroplet container; S320, amplifying the nucleic acids in the spread microdroplets; S330, imaging and detecting the plurality of microdroplets in real time during the nucleic acid amplification.

In an embodiment, the step S310 includes a method for spreading the microdroplets including: S311, providing the microdroplet container 60, the microdroplet container 60 having the opening 631, and the microdroplet container 60 containing the second liquid 699; S312, providing the first liquid 190, wherein the density of the first liquid 190 is greater than the density of the second liquid 699, and the first liquid 190 is not miscible with the second liquid 699; and stacking the plurality of microdroplets generated from the first liquid 190 on the microdroplet container bottom plate 610; and S313, temperature cycling the plurality of microdroplets between high and low temperatures until the plurality of microdroplets are spread on the container bottom plate 610.

The plurality of microdroplets are generated in the microdroplet container 60, settled onto the container bottom plate 610 of the microdroplet container 60, and are disorderly stacked together. The large number of microdroplets settled on the container bottom plate 610 form multiple layers of microdroplets on the container bottom plate 610. Moreover, during the downward settlement process, the plurality of microdroplets generated by microdroplet generating device are aggregated in the middle of the microdroplet container and gathered together, which is not conducive to observation.

In an embodiment, the second liquid 699 is the oil phase composition.

In an embodiment, the components of the oil phase composition include mineral oil and surfactant. The volume percentage of the mineral oil in the oil phase composition is 88% to 98.5%. The surfactant includes a silicon-oxygen chain non-ionic surfactant containing a long-chain alkyl group. The volume percentage of the silicon-oxygen chain non-ionic surfactant containing the long-chain alkyl group in the oil phase composition is 1.5% to 12%.

In an embodiment, the first liquid is the nucleic acid amplification reaction liquid to be tested.

In an embodiment, the step S312 includes: S3122, providing the liquid discharging nozzle 110 having the outlet end 112, the first liquid 190 is stored in the liquid discharging nozzle 110; S3124, inserting the outlet end 112 of the liquid discharging nozzle 110 below the liquid surface of the second liquid 699, and moving the outlet end 112 at a periodically changed speed, and in the first half of the period and the second half of the period of the speed change, the speeds of the outlet end 112 of the liquid discharging nozzle 110 change monotonously; and S3126, discharging the first liquid from the outlet end 112 of the liquid discharging nozzle 110 according to the periodical moving of the outlet end 112 of the liquid discharging nozzle 110 to form the plurality of microdroplets below the liquid surface of the second liquid 699 and stacked on the bottom plate 610 of the microdroplet container.

In an embodiment, in step S3124, the speed of the outlet end 112 of the liquid discharging nozzle 110 below the liquid surface of the second liquid 699 changes in the form of a cosine curve.

In an embodiment, in step S3124, the moving trajectory of the outlet end 112 of the liquid discharging nozzle 110 below the liquid surface of the second liquid 699 includes one or a combination of various trajectories such as a straight line segment, an arc-shaped line segment, or a polygon.

In an embodiment, the step S312 includes:
S3121, providing the liquid discharging nozzle 110 having the outlet end 112, wherein the first liquid 190 is stored in the liquid discharging nozzle 110;
S3123, inserting the outlet end 112 of the liquid discharging nozzle 110 below the liquid surface of the second liquid 699 to have an instantaneous accelerated motion; and
S3125, discharging the first liquid 190 from the outlet end 112 of the liquid discharging nozzle 110 according to the instantaneous accelerated motion of the outlet end 112 of the liquid discharging nozzle 110 to form the plurality of microdroplets below the liquid surface of the second liquid 699 and stacked on the bottom plate 610 of the microdroplet container.

In an embodiment, in step S3123, the speeds of the outlet end 112 of the liquid discharging nozzle 110 in the first half and in the second half of the period of the instantaneous accelerated periodic motion of the outlet end 112 of the liquid discharging nozzle 110 have the same magnitude but opposite directions. In an embodiment, in step S3123, the moving trajectory of the instantaneous accelerated periodic motion includes one or a combination of various trajectories such as a straight line segment, an arc-shaped line segment, or a polygon.

In an embodiment, the step S313 includes: S3131, increasing the temperature of the plurality of microdroplets; S3133, decreasing the temperature of the plurality of microdroplets; S3135, cycling the temperature of the plurality of microdroplets between the high and low temperatures for a plurality of times until the plurality of microdroplets are spread on the bottom plate of the microdroplet container.

In an embodiment, the second liquid 699 is firstly placed in the microdroplet container 60 before generating the plurality of microdroplets by the microdroplet generating device 10. When the liquid surface of the second liquid 699 is at the same level of the horizontal surface of the surrounding surface 641, the adding of the second liquid 699 is stopped. At this time, the liquid surface of the second liquid 699 and the surface of the surrounding surface 641 are at the same horizontal plane, which can ensure that the liquid surface of the second liquid 699 in the microdroplet container 60 is flat, and conveniently ensure that the top surface of the oil phase above the bottom surface of the container is a horizontal flat surface to facilitate the imaging.

The nucleic acid amplification reaction liquid to be tested is microdropletized by the microdroplet generating device 10 in the second liquid 699 to form a large number of microdroplets. The plurality of microdroplets are settled into the plurality reacting units 612 of the microdroplet container bottom plate 610. The surrounding surface 641 is parallel to the container bottom plate 610 to ensure that the second liquid 699 in the microdroplet container has the horizontal surface. Each reacting unit 612 can accommodate a plurality of microdroplets, so that the microdroplet container 60 can accommodate more than 20,000 microdroplets.

In an embodiment, in step S3125, the plurality of microdroplets are spread on the bottom plate 610 of the microdroplet container due to the moving trajectory of the instantaneous accelerated motion of the outlet end 112 of the liquid discharging nozzle 110. The trajectory of the instantaneous accelerated motion of the outlet end 112 of the liquid discharging nozzle 110 can make the plurality of microdroplets separated from each other when falling in the microdroplet container 60, so that the plurality microdroplets during the falling in the microdroplet container 60 are not stacked with each other. Therefore, the plurality of microdroplets are spread in the microdroplet container 60, being conducive to imaging and observation.

In an embodiment, the bottom plate 610 of the microdroplet container is coated with an oleophobic layer. The oleophobic layer is also called oleophobic coating, which is a composite coating material and is a functional material coating often having an oleophobic function. The oleophobic layer is a coating on the surface formed by using a spray-coating technique with nano-silica ($SiO_2$) as a raw material. The oleophobic layer has good light transmittance, hydrophobicity, and oleophobicity.

In an embodiment, the temperature controlling device 20 is used in the microdroplet spreading method in the above embodiments. The temperature controlling device 20 includes a flexible circuit board 220, a heating substrate 240 disposed at an interval from the flexible circuit board 220, and a plurality of semiconductor electric couples 230 disposed between the flexible circuit board 220 and the heating substrate 240.

Through the high-low temperature cycling, the spreading adopts the principle of thermal expansion and thermal contraction. The kinetic energy of the molecule increases and the mean free path of the molecule increases when the temperature of a substance increases, occurring the thermal expansion. Similarly, the kinetic energy of the molecule decreases and the mean free path of the molecule decreases when the temperature of the substance decreases, occurring the thermal contraction. As the temperature changes, the viscosity of the sample droplet decreases and the volume of the sample droplet decreases when the temperature increases. Moreover, the higher the temperature, the lower the viscosity. When the temperature is around 60° C., the shape of the sample droplet is the softest, and the shape of the sample droplet is roughly hexagonal. However, at other temperatures, the shapes of the sample droplets have less variability, and they are not easy to be spread in the droplet container.

Referring to FIG. 50, the plurality of microdroplets are dropped into the microdroplet container 60, and the plurality of microdroplets are stacked on the microdroplet container bottom plate 610; that is, the plurality of microdroplets form multilayers of microdroplets on the microdroplet container bottom plate 610. During the detection of the fluorescent signal, when imaging the plurality of microdroplets, the plurality of layers affect with each other, which affects the imaging and detection of the plurality of microdroplets. Therefore, the microdroplet container 60 containing the plurality of microdroplets is subjected to the high-low temperature cycling. The plurality of microdroplets are subjected to high-low temperature cycling multiple times until the plurality of microdroplets are spread on the bottom plate 610 of the microdroplet container, so that the large number of the microdroplets are spread in the reacting unit 612, being conducive to a large-scale and parallel observation of a tremendous number of microdroplets. The plurality of microdroplets need to be spread in the microdroplet container 60 in order to obtain more accurate information about the nucleic acid amplification reaction of the plurality of microdroplets. By spreading the plurality of microdroplets in the microdroplet container 60 to form a monolayer, the mutual influence between multilayers of microdroplets is avoided, so that the fluorescence signal detecting device 30 obtains more accurate fluorescence information through imaging and detection, facilitating the quantitative analysis.

In an embodiment, the step S312, at which the microdroplets are generated by using the microdroplet generating method including step S201, step S202, and step S203 in the above-described embodiments, includes: S3121, providing the liquid discharging nozzle having the outlet end, wherein the first liquid is stored in the liquid discharging nozzle; S3123, inserting the outlet end of the liquid discharging nozzle below the liquid surface of the second liquid to have an instantaneous accelerated motion; and S3125, discharging the first liquid from the outlet end of the liquid discharging nozzle according to the instantaneous accelerated motion of the outlet end of the liquid discharging nozzle to form the plurality of microdroplets in the second liquid and stacked on the bottom plate of the microdroplet container.

In an embodiment, in step S3123, the speeds of the outlet end of the liquid discharging nozzle in the first half and in the second half of the period of instantaneous accelerated motion of the outlet end of the liquid discharging nozzle have the same magnitude but opposite directions. In an embodiment, in step S3123, the moving trajectory of the instantaneous accelerated motion includes one or a combination of various trajectories such as a straight line segment, an arc-shaped line segment, or a polygon.

In an embodiment, the step S312, at which the microdroplets are generated by using the microdroplet generating method including step S211, step S212, and step S213 in the above-described embodiments, includes: S3122, providing the liquid discharging nozzle having the outlet end, the first liquid is stored in the liquid discharging nozzle; S3124, inserting the outlet end of the liquid discharging nozzle below the liquid surface of the second liquid, and moving the outlet end at a periodically changed speed, and in the first half of the period and the second half of the period of the speed change, the speeds of the outlet end of the liquid discharging nozzle change monotonously; and S3126, discharging the first liquid from the outlet end of the liquid discharging nozzle according to the periodical moving of the outlet end of the liquid discharging nozzle to form the plurality of microdroplets below the liquid surface of the second liquid and stacked on the bottom plate of the microdroplet container.

In an embodiment, in step S3124, the speed of the outlet end of the liquid discharging nozzle below the liquid surface of the second liquid changes in the form of a cosine curve.

In an embodiment, in step S3124, the moving trajectory of the outlet end of the liquid discharging nozzle below the liquid surface of the second liquid includes one or a combination of various trajectories such as a straight line segment, an arc-shaped line segment, or a polygon.

In an embodiment, the steps of high-low temperature cycling through the temperature controlling device 20 are as follows: first, the plurality of microdroplets are heated to 90° C. to 95° C. and heated for 5 min to 10 min; then, the plurality of microdroplets are cooled to 40° C. to 60° C., and annealed and extended for 30 s to 60 s; finally, the microdroplets are cycled multiple times, and the temperature is reduced to 0° C. to 10° C. to store the plurality of microdroplets.

In an embodiment, the steps of high-low temperature cycling through the temperature controlling device 20 includes: first, the plurality of microdroplets are heated to 95° C. and heated for 10 min to hot start the enzymes in the plurality of microdroplets; then, the plurality of microdroplets are denatured for 30 s after the enzymes are hot started in the plurality of microdroplets; next, the plurality of microdroplets are cooled to 55° C. after the plurality of microdroplets are denaturated, and annealed and extended for 45 s, the plurality of microdroplets are photographed and cycled 45 times; finally, the temperature is reduced to 4° C. to store the plurality of microdroplets after the 45 cycles for a long time.

The nucleic acid amplification reaction liquid to be tested is microdropletized into a plurality of microdroplets through the microdroplet generating device 10 for detection. It is not conducive to observation on the condition that the plurality of microdroplets generated by the microdroplet generating device 10 are aggregated and gathered together in the middle of the microdroplet container 60 during the downward settlement process. Therefore, the microdroplets need to be spread in the microdroplet container in order to obtain more accurate information about the nucleic acid amplification reaction of the microdroplets. By spreading the plurality of microdroplets in the microdroplet container to form a monolayer, the mutual influence between multilayers of microdroplets is avoided, so that the fluorescence signal detecting device 30 obtains more accurate fluorescence information through imaging and detection, facilitating the quantitative analysis.

In an embodiment, the step S320 of performing the nucleic acid amplification on the spread microdroplets is as follows: first, the microdroplet container 60 is placed on the heating substrate 240 of the temperature controlling device 20; then, the plurality of microdroplets are heated to 95° C. and heated for 10 min which is to hot start the enzymes in the plurality of microdroplets; next, the plurality of microdroplets are denatured for 30 s after the enzymes are hot started in the plurality of microdroplets; next, the plurality of microdroplets are cooled to 55° C. after the plurality of microdroplets are denaturated, and annealed and extended for 45 s, the plurality of microdroplets are cycled 45 times; finally, the temperature is reduced to 4° C. to store the plurality of microdroplets after the 45 cycles for a long time.

The temperature controlling device 20 adopts the flexible circuit board 220 and the heat conduction enhancing layer 250 to uniformly distribute the temperature of the microdroplet container 60, and accelerate the heat conducting performance of the semiconductor cooler. The temperature sensor 260 disposed at the surface of the heat conduction enhancing layer 250 is connected to the second controller 210 to detect the real-time temperature of the microdroplet container 60 when the nucleic acids in the microdroplets are amplified at different temperature ranges. And the temperature sensor 260 can further feed the temperature information to the second controller 210 to control the heating temperature of the microdroplets in real time. The temperature ranges can be rapidly switched within a few seconds. The temperature controlling device 20 can achieve instantaneous temperature increase and temperature decrease to shorten the process of temperature increase and temperature decrease, thereby realizing the cycling between the high and low temperatures, reducing the detection time of the digital PCR detection apparatus 1 and improving the detection efficiency.

The technical features of the above-mentioned embodiments can be combined arbitrarily. To simplify the description, not all possible combinations of the technical features in the above-mentioned embodiments are described. However, as long as there is no contradiction in the combination of these technical features, the combinations all should be considered within the scope of this description.

The above-mentioned embodiments only express several implementation manners of the present application, and their descriptions are relatively specific and detailed, but they should not be construed as limiting the patent scope of the present application. It should be noted that, for a person of ordinary skill in the art, without departing from the concept of the present application, a number of modifications and improvements can be made, which all fall within the protection scope of the present application. Therefore, the protection scope of the patent of this application shall be subject to the appended claims.

Finally, it should also be noted that in this application, relational terms such as "first" and "second" are used only to distinguish one entity or operation from another entity or operation, and do not necessarily require or imply any actual relationship or order between these entities or operations. Moreover, the terms "include", "comprise" and any other variant thereof are intended to cover non-exclusive inclusion, so that a process, method, article, or device including a series of elements includes not only those elements, but also the elements that are not explicitly listed or the elements that are inherent to this process, method, article, or equipment. Without more restrictions, the element defined by the phrase "include a . . . " does not exclude that there are other identical elements in the process, method, article or equipment that includes the element.

The embodiments in this specification are described in a progressive manner. Each embodiment focuses on the differences from other embodiments, and the same or similar parts between the embodiments can refer to each other.

The descriptions of the provided embodiments enable those skilled in the art to implement or use this application. Various modifications to these embodiments will be apparent to those skilled in the art. The general principles defined herein can be implemented in other embodiments without departing from the spirit or scope of the present application. Therefore, the present application will not be limited to the embodiments shown in this application, but should conform to the widest scope consistent with the principles and novel features provided herein.

What is claimed is:

1. A temperature controlling device for temperature cycling a microdroplet, comprising:
   a flexible circuit board, which is deformed during heating and cooling processes;
   a heating substrate spaced from the flexible circuit board, the heating substrate comprising a first surface and a second surface opposite to each other;
   a plurality of semiconductor electric couples disposed between the flexible circuit board and the first surface, and the plurality of semiconductor electric couples being connected to each other in series, in parallel, or in combination thereof; and
   a microdroplet container containing a plurality of the microdroplet, the microdroplet container being disposed on the heating substrate and away from the plurality of semiconductor electric couples; wherein
   each of the plurality of semiconductor electric couples comprises a P-type couple component and a N-type couple component spaced from the P-type couple component;
   the first surface comprises a plurality of first electrode plates spaced from each other, one first electrode plate corresponds to one semiconductor electric couple, the P-type couple components and the N-type couple components of the semiconductor electric couples are connected in series through the first electrode plates;
   the flexible circuit board comprises a plurality of second electrode plates spaced from each other and connected in series, two adjacent semiconductor electric couples are connected in series by one second electrode plate; and
   the heating substrate is configured to increase and decrease a temperature of the microdroplet container.

2. The temperature controlling device of claim 1, further comprising a thermal conduction enhancing layer disposed on the second surface.

3. The temperature controlling device of claim 2, wherein a material of the thermal conduction enhancing layer comprises graphene.

4. The temperature controlling device of claim 1, characterized by further comprising a second controller electrically connected to the plurality of semiconductor electric couples for controlling a magnitude of an electric current.

5. The temperature controlling device of claim 4, characterized by further comprising a temperature sensor, disposed on the second surface and electrically connected to the second controller to detect the temperature of the second surface and transmit the temperature to the second controller.

6. The temperature controlling device of claim 5, wherein the second controller comprises:
   a temperature controlling unit connected to the temperature sensor to detect the temperature of the second surface in real time;
   a controlling circuit connected to the flexible circuit board to regulate the temperature variation of the plurality of semiconductor electric couples.

7. The temperature controlling device of claim 6, wherein the flexible circuit board is provided with a first electrode and a second electrode, and the plurality of second electrode plates connected in series are further connected to the first electrode and the second electrode in series, and the first electrode and the second electrode are respectively connected to the controlling circuit.

8. The temperature controlling device of claim 1, wherein the temperature controlling device further comprises a heat dissipating device, and the heat dissipating device comprises a substrate and a heat dissipating sheets connected to the substrate, and the flexible circuit board is disposed on a surface of the substrate.

9. The temperature controlling device of claim 8, wherein the temperature controlling device further comprises a fan disposed around the heat dissipating sheets.

10. A method for spreading microdroplets, comprising:
    providing a microdroplet container and the temperature controlling device of claim 1, the microdroplet container having an opening, and the microdroplet container containing a second liquid;
    providing a first liquid, a density of the first liquid being greater than a density of the second liquid, and the first liquid being not miscible with the second liquid; and stacking the plurality of microdroplets generated from the first liquid on a bottom plate of the microdroplet container;
    temperature cycling the plurality of microdroplets by the temperature controlling device between high and low temperatures till the plurality of microdroplets are spread on the bottom plate.

11. The method of claim 10, wherein the step of providing the first liquid and stacking the plurality of microdroplets comprises:
    providing a liquid discharging nozzle having an outlet end, the first liquid is stored in the liquid discharging nozzle;
    inserting the outlet end of the liquid discharging nozzle below a liquid surface of the second liquid, and moving the outlet end at a periodically changed speed, wherein in a first half of a period and a second half of a period of a speed change, speeds of the outlet end of the liquid discharging nozzle change monotonously;
    discharging the first liquid from the outlet end of the liquid discharging nozzle according to the periodical moving of the outlet end of the liquid discharging nozzle to form the plurality of microdroplets below the liquid surface of the second liquid and stacked on the bottom plate of the microdroplet container.

12. The method of claim 11, wherein in the step of inserting and moving the outlet end of the liquid discharging nozzle, the speed of the outlet end of the liquid discharging nozzle below the liquid surface of the second liquid changes in the form of a cosine curve.

13. The method of claim 12, wherein in the step of inserting and moving the outlet end of the liquid discharging nozzle, a moving trajectory of the outlet end of the liquid discharging nozzle below the liquid surface of the second liquid comprises one or a combination of a straight line segment, an arc-shaped line segment, or a polygon.

14. The method of claim 10, wherein the step of providing the first liquid and stacking the plurality of microdroplets comprises:
    providing a liquid discharging nozzle having an outlet end, the first liquid being stored in the liquid discharging nozzle;
    inserting the outlet end of the liquid discharging nozzle below a liquid surface of the second liquid to have an instantaneous accelerated motion;
    discharging the first liquid from the outlet end of the liquid discharging nozzle according to the instantaneous accelerated periodic motion of the outlet end of the liquid discharging nozzle to form the plurality of microdroplets below the liquid surface of the second liquid and stacked on the bottom plate of the microdroplet container.

15. The method of claim 14, wherein in the step of inserting the outlet end of the liquid discharging nozzle below the liquid surface of the second liquid to have the instantaneous accelerated motion, speeds of the outlet end of the liquid discharging nozzle in a first half and in a second half of a period of the instantaneous accelerated periodic motion of the outlet end of the liquid discharging nozzle have the same magnitude but opposite directions.

16. The method of claim 15, wherein in the step of inserting the outlet end of the liquid discharging nozzle below the liquid surface of the second liquid to have the instantaneous accelerated motion, a moving trajectory of the instantaneous accelerated periodic motion comprises one or a combination of a straight line segment, an arc-shaped line segment, or a polygon.

17. The method of claim 10, wherein the step of temperature cycling the plurality of microdroplets by the temperature controlling device between high and low temperatures till the plurality of microdroplets are spread on the bottom plate comprises:
   increasing a temperature of the plurality of microdroplets;
   decreasing the temperature of the plurality of microdroplets;
   temperature cycling the plurality of microdroplets between the high and low temperatures for a plurality of times till the plurality of microdroplets are spread on the bottom plate of the microdroplet container.

* * * * *